US009663549B2

(12) United States Patent
Eloranta et al.

(10) Patent No.: US 9,663,549 B2
(45) Date of Patent: May 30, 2017

(54) THERAPEUTICALLY ACTIVE 17-NITROGEN SUBSTITUTED ESTRATREINTHIAZOLE DERIVATIVES AS INHIBITORS OF 17β-HYDROXYSTEROID DEHYDROGENASE

(71) Applicant: FORENDO PHARMA LTD, Turku (FI)

(72) Inventors: Maire Eloranta, Oulu (FI); Leena Hirvelä, Oulu (FI); Lauri Kangas, Lieto (FI); Pasi Koskimies, Turku (FI); Risto Lammintausta, Turku (FI); Mikko Unkila, Piikkiö (FI)

(73) Assignee: FORENDO PHARMA LTD., Turku (FI)

(*) Notice: Subject to any disclaimer, the term of this patent is extended or adjusted under 35 U.S.C. 154(b) by 0 days.

(21) Appl. No.: 14/392,291

(22) PCT Filed: Jun. 25, 2014

(86) PCT No.: PCT/FI2014/050518
§ 371 (c)(1),
(2) Date: Dec. 23, 2015

(87) PCT Pub. No.: WO2014/207310
PCT Pub. Date: Dec. 31, 2014

(65) Prior Publication Data
US 2017/0081357 A1 Mar. 23, 2017

(30) Foreign Application Priority Data
Jun. 25, 2013 (FI) .................................. 20135694

(51) Int. Cl.
C07J 43/00 (2006.01)
A61K 31/58 (2006.01)
(52) U.S. Cl.
CPC ............ *C07J 43/003* (2013.01); *A61K 31/58* (2013.01)
(58) Field of Classification Search
None
See application file for complete search history.

(56) References Cited

U.S. PATENT DOCUMENTS 8,030,298 B2 * 10/2011 Messinger ............... C07J 43/00
514/176
2006/0281710 A1 12/2006 Messinger et al.
2008/0255075 A1 10/2008 Messinger et al.

FOREIGN PATENT DOCUMENTS

| WO | WO 99/46279 | 9/1999 |
|---|---|---|
| WO | WO 00/07996 | 2/2000 |
| WO | WO 01/42181 | 6/2001 |
| WO | WO 03/022835 | 3/2003 |
| WO | WO 03/033487 | 4/2003 |
| WO | WO 2004/046111 | 6/2004 |
| WO | WO 2004/060488 | 7/2004 |
| WO | WO 2004/085345 | 10/2004 |
| WO | WO 2004/085457 | 10/2004 |
| WO | WO 2004/110459 | 12/2004 |
| WO | WO 2005/032527 | 4/2005 |
| WO | WO 2005/047303 | 5/2005 |
| WO | WO 2005/084295 | 9/2005 |
| WO | WO 2006/003012 | 1/2006 |
| WO | WO 2006/003013 | 1/2006 |
| WO | WO 2006/027347 | 3/2006 |
| WO | WO 2006/125800 | 11/2006 |
| WO | WO 2008/034796 | 3/2008 |
| WO | WO 2008/065100 | 6/2008 |

OTHER PUBLICATIONS

Allan et al., "Modification of Estrone at the 6, 16, and 17 Positions: Novel Potent Inhibitors of 17β-Hydroxysteroid Dehydrogenase Type 1", *J. Med. Chem.*, vol. 49, No. 4., pp. 1325-1345, Jan. 2006.
International Search Report and Written Opinion for International Application No. PCT/FI2014/050518 (Aug. 18, 2014).
Koffman et al., "Evidence for Involvement of Tyrosine in Estradiol Binding by Rat Uterus Estrogen Receptor", *J. Steroid Biochem. Molec. Biol.*, vol. 38, No. 2, pp. 135-139, 1991.
Messinger et al., "Estrone C15 derivatives—A new class of 17β-hydroxysteroid dehydrogenase type 1 inhibitors", *Molecular and Cellular Endocrinology*, vol. 301, pp. 216-224, (2009).
Möller et al., "Species Used for Drug Testing Reveal Different Inhibition Susceptibility for 17 beta-Hydroxysteroid Dehydrogenase Type 1", *PLoS One*, vol. 5, Issue 6, pp. 1 -11; (Jun. 2010).
Poirier, Donald, "Inhibitors of 17β-Hydroxysteroid Dehydrogenases", *Current Medicinal Chemistry*, vol. 10, No. 6; pp. 453-477; (2003).
Poirier, Donald, "17β-Hydroxysteroid dehydrogenase inhibitors: a patent review", *Expert Opin. Ther. Patents,* 20(9), pp. 1123-1145; (2010).

(Continued)

*Primary Examiner* — Kamal Saeed
(74) *Attorney, Agent, or Firm* — Brinks Gilson & Lione

(57) ABSTRACT

The invention relates to compounds of formula (I) and pharmaceutically acceptable salts thereof wherein R2 to R7 are as defined in the claims. The invention further relates to their use as inhibitors of 17β-HSD and in treatment or prevention of steroid hormone de-pendent diseases or disorders, such as steroid hormone dependent diseases or disorders requiring the inhibition of the 17β-HSD1 enzyme and/or requiring the lowering of the endogenous estradiol concentration. The present invention also relates to the preparation of the aforementioned compounds and to pharmaceutical compositions comprising as an active ingredient (s) one or more of the afore-mentioned compounds or pharmaceutically acceptable salts thereof.

24 Claims, No Drawings

(56) References Cited

OTHER PUBLICATIONS

Puranen et al., "Site-directed mutagenesis of the putative active site of human 17β-hydroxysteroid dehydrogenase type 1", *Biochem. J.*, 304; pp. 289-293; (1994).
Search Report for Finnish Patent Application No. 20135694 (Feb. 12, 2014).

* cited by examiner

THERAPEUTICALLY ACTIVE 17-NITROGEN SUBSTITUTED ESTRATREINTHIAZOLE DERIVATIVES AS INHIBITORS OF 17β-HYDROXYSTEROID DEHYDROGENASE

FIELD OF THE INVENTION

The present invention relates to novel estrone C-17 ketimine C-15 thiazole derivatives, to their pharmaceutically acceptable salts, and their use in therapy. The invention further relates to pharmaceutical compositions comprising these compounds as active ingredients and to methods for their preparation.

BACKGROUND OF THE INVENTION

17β-hydroxysteroid dehydrogenases (17β-HSDs), also known as 17-ketosteroid reductases (17-KSR) are NAD(H)- and/or NAPD(H)-dependent alcohol oxidoreductase enzymes which catalyse the last and key step in formation of all estrogens and androgens. More specifically 17β-HSDs catalyse the dehydrogenation (oxidation) of 17-hydroxysteroids into corresponding 17-ketosteroids or hydrogenation (reduction) of inactive 17-ketosteroids into corresponding active 17-hydroxysteroids.

As both estrogens and androgens have the highest affinity for their receptors in the 17β-hydroxy form, the 17β-HSD/KSRs regulate the biological activity of the sex hormones. At present, 15 human members of 17β-HSDs have been described (type 1-15). Different types of 17β-HSD/KSRs differ in their substrate and cofactor specificities. The 17KSR activities convert low-activity precursors to more potent forms while 17β-HSD activities decrease the potency of estrogens and androgens and consequently may protect tissues from excessive hormone action.

Each type of 17β-HSD has a selective substrate affinity and a distinctive, although in some cases overlapping, tissue distribution.

Type 1 17β-hydroxysteroid dehydrogenase (17β-HSD1) is most abundantly expressed in the ovarian granulosa cells of the developing follicles in ovaries and in human placenta, both being estrogen biosynthetic tissues. In addition, 17β-HSD1 is expressed in estrogen target tissues, including breast, endometrium and bone. The human 17β-HSD1 is specific to estrogenic substrates and in vivo catalyzes the reduction of estrone to estradiol.

Type 2 17β-hydroxysteroid dehydrogenase (17β-HSD2) on the other hand converts estradiol, testosterone and 5a-dihydrotestrosterone to their less active forms estrone, androstenedione and 5a-androstanedione, respectively. Due to its wide and abundant expression in number of various estrogen and androgen target tissues, such as uterus, placenta, liver and the gastrointestinal and urinary tracts, it has been suggested that type 2 enzyme protects tissues from excessive steroid actions.

Estradiol (E2) is about 10 times as potent as estrone (E1) and about 80 times as potent as estratriol (E3) in its estrogenic effect. In contrast to certain other estrogens, estradiol binds well to both estrogen receptors ERα and ERβ, and thus regulates the expression of a variety of genes.

Although both 17β-HSD1 and 17β-HSD2 are present in healthy premenopausal humans, increased ratio of 17β-HSD1 to 17-HSD2 in the tumors of postmenopausal patients with hormone-dependent breast cancer has been shown in several studies. 17HSD1 gene amplification and loss of heterozygosity of 17HSD2 allele are potential mechanisms involved to increased reductive estrogen synthesis pathway in breast tumors. Increased ratio of type 1 enzyme to type 2 enzyme results in an increased level of estradiol that then promotes the proliferation of the cancerous tissue via the estrogen receptors (ER). High levels of estrogen thus support certain cancers such as breast cancer and cancer of the uterine lining i.e. endometrial cancer and uterine cancer.

Similarly it has been suggested that 17β-HSD2 is downregulated in endometriosis while both aromatase and 17β-HSD1 are expressed or upregulated in comparison with normal endometrium. This again results in the presence of high concentration of estradiol (E2) which drives the proliferation of the tissue. Similar mechanism has been elucidated in uterine leiomyoma (uterine fibroids) and endometrial hyperplasia.

Reduction of the endogenous estradiol concentration in affected tissues will result in reduced or impaired proliferation of 17β-estradiol cells in said tissues and may thus be utilized in prevention and treatment of malign and benign estradiol dependent pathologies. Due to the proposed involvement of 17β-estradiol in a number of malign and benign pathologies, inhibitors of 17β-hydroxysteroid dehydrogenases, that can be used to impair endogenous production of estradiol from estrone, can have therapeutic value in the prevention or the treatment of such disorders or diseases are in great demand.

Some small-molecule inhibitors of 17β-HSD1 enzyme have been identified and reviewed in Poirier D. (2003) Curr Med Chem 10: 453-77 and Poirier D. (2010) Expert Opin. Ther. Patents 20(9): 1123-1145. Further, small molecule inhibitors of 173-HSD's have been disclosed in WO 2001/42181, WO 2003/022835, WO 2003/033487, WO 2004/046111, WO 2004/060488, WO 2004/110459, WO 2005/032527, and WO 2005/084295.

WO2004/085457 discloses steroidal compounds capable of inhibiting 17β-hydroxysteroid dehydrogenase. WO2006/003012 discloses 2-substituted D-homo-estriene derivatives suitable for the treatment of estrogen-dependent diseases that can be influenced by the inhibition of the 17β-hydroxysteroid dehydrogenase type 1. Similarly WO2006/003013 presents 2-substituted estratrienones usable for preventing and treating estrogen-dependent diseases influenced by inhibiting 17β-hydroxysteroid dehydrogenase type 1.

15-substituted estradiol analogues acting as locally active estrogens are presented in WO2004/085345. WO2006/027347 discloses 15b-substituted estradiol derivatives having selective estrogenic activity for the treatment or prevention of estrogen receptor-related diseases and physiological conditions. Further, WO2005/047303 discloses 3, 15 substituted estrone derivatives capable of inhibiting the 17β-hydroxysteroid dehydrogenase type 1.

International application WO2008/034796 relates to estratrien triazoles suitable for use in treatment and prevention of steroid hormone dependent diseases or disorders requiring the inhibition of a 17β-hydroxysteroid dehydrogenases such as 17β-HSD type 1, type 2 or type 3 enzyme. Inhibitors of 17β-HSD type 3 enzyme have been disclosed in WO99/46279.

BRIEF DESCRIPTION OF THE INVENTION

An object of the present invention is to provide compounds useful in treating disorders and diseases associated with increased level of estradiol and/or treatable by inhibition of 17β-HSD1 enzyme. It is further an object of the present invention to provide compounds that show little or no inhibitory effect on 17β-HSD2 enzyme.

One of the problems associated with the known 17β-HSD1 inhibitors is the disposition, in particular the metabolic stability, of the compounds. It is therefore yet a further object of the present invention to provide compounds with improved metabolic stability.

The present invention provides a novel compound of formula (I)

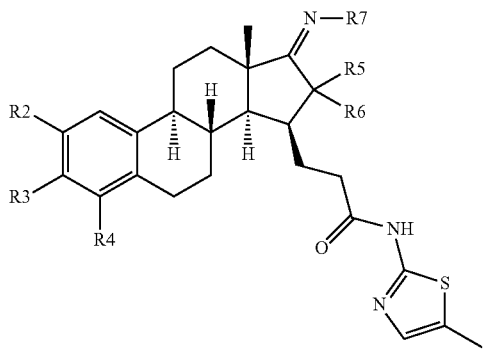

(I)

wherein (i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_nN(R')_2$, OR', $(CH_2)_nOR'$, $CO_2R'$, CONHR', NHCOR'', C(=NH)R'', C(=N—OH)R'' and COR'';

R3 is selected from the group consisting of H, $C_{1-6}$-alkyl, $C_{1-3}$-haloalkyl, $C_{1-3}$-perhaloalkyl, $NR'_2$, $N_3$, and $OR_3'$, wherein $R_3'$ is selected from the group consisting of R', benzyl, succinyl, optionally acylated glucuronyl, $(CH_2)_nOH$, $SO_2OH$, $SO_2R''$, tosyl, $SO_2N(R')_2$, $PO(OR')_2$, COOR''', $C(O)N(R')_2$, $C(O)(CH_2)_nN(R')_2$, $C(O)CH_2NHC(O)R'$, $C(O)CH_2NHC(O)OR''$ and $C(O)R'''$;

wherein

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R'' is $C_{1-6}$-alkyl, $C_{1-3}$-haloalkyl, or $C_{1-3}$-perhaloalkyl;

R''' is $C_{1-18}$-alkyl, $C_{2-18}$-alkenyl, $—(CH_2)_n—C_{3-6}$-cycloalkyl, or optionally substituted phenyl; and n is 1 or 2; or (i-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(ii-a) R5 and R6 are each H or R5 and R6 form together =CH—OH; and

R7 is selected from the group consisting of ureido, $R'O—C_{1-3}$-alkylenyl, $R'S—C_{1-3}$-alkylenyl, $R'_2N—C_{1-3}$-alkylenyl, and OR7', wherein R7' is selected from the group consisting of H, $C_{1-6}$-alkyl, $C_{3-6}$-alkenyl, and carboxy-$C_{1-3}$-alkylenyl; or (ii-b) R5 and R6 and =NR7 form together with the carbons they are attached to a structure

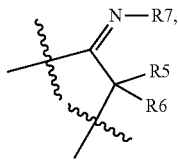

which is selected from

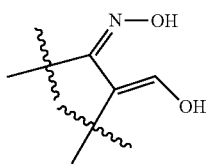 and , wherein X is O or NH;

or a pharmaceutically acceptable salt thereof.

Compounds of the present invention may be useful in therapy, especially in the treatment or prevention of steroid hormone dependent diseases or disorders requiring the lowering of the endogenous estradiol concentration or the inhibition of 17β-HSD enzymes, in animals, in particular mammals, and humans. In particular, compounds of formula (I) represent inhibitors of the 17β-HSD1 enzyme, possessing pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome or lower urinary tract syndrome. Further estrogen-dependent diseases which may be treated and/or prevented with an effective amount of a compound of the invention include multiple sclerosis, obesity, rheumatoid arthritis, colon cancer, tissue wounds, skin wrinkles and cataracts. The compounds of the present invention typically have an inhibitory activity at the 17-β-HSD1 enzyme in the IC50 range of 0.1 nM to 1 µM. The inhibitory activity can be measured as explained in context of the experimental examples.

The invention also relates to pharmaceutical compositions comprising an effective amount of one or more compound(s) of formula (I).

Further the invention relates to a compound of formula (I) or a pharmaceutically acceptable salt thereof for use as a medicament.

The invention also relates to a compound of formula (I) or a pharmaceutically acceptable salt thereof for use in the treatment of estradiol dependent malign or benign diseases and disorders.

Finally the invention provides a method for the preparation of compounds of formula (I).

DETAILED DESCRIPTION OF THE INVENTION

Compounds of the invention contain steroidal core structure having a defined stereochemistry that is the natural configuration of estrogens.

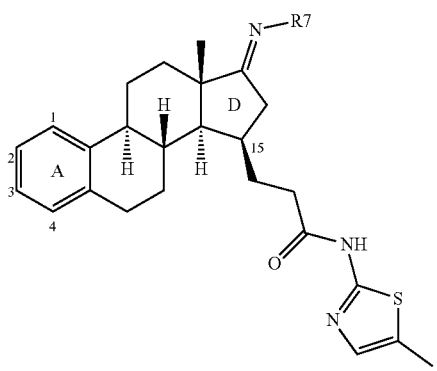

Compounds of the invention bear a methyl thiazolyl side chain at C15 in β-configuration which, together with the specific substitution pattern of the A and/or D ring(s), provides the inventive properties of the compounds of the present invention. Also, the C-17 carbonyl group of the native estrone core is masked as a C-17 ketimine to further enhance the metabolic and/or inhibitory properties of the compounds of the present invention.

The term "halogen" as used herein and hereafter by itself or as part of other groups refers to the Group VIIa elements and includes F, Cl, Br and I groups.

The term "alkyl" as used herein and hereafter as such or as part of haloalkyl, perhaloalkyl or alkoxy group is an aliphatic linear, branched or cyclic, especially linear or branched, hydrocarbon group having the indicated number of carbon atoms, for example $C_{1-6}$-alkyl has 1 to 6 carbon atoms in the alkyl moiety and thus, for example, $C_{1-4}$-alkyl includes methyl, ethyl, n-propyl, isopropyl, n-butyl, sec-butyl, isobutyl, tert-butyl and $C_{1-6}$-alkyl additionally includes branched and straight chain pentyl and hexyl.

The term "haloalkyl" as used herein and hereafter refers to any of the above alkyl groups where one or more hydrogen atoms are replaced by halogen(s): in particular I, Br, F or Cl. Examples of haloalkyl groups include without limitation chloromethyl, fluoromethyl and —$CH_2CF_3$. The term "perhaloalkyl" is understood to refer to an alkyl group, in which all the hydrogen atoms are replaced by halogen atoms. Preferred examples include trifluoromethyl (—$CF_3$) and trichloromethyl (—$CCl_3$).

The term "$C_{3-6}$-cycloalkyl" as used herein and hereafter refers to cycloalkyl groups having 3 to 6 carbon atoms and thus includes cyclopropyl, cyclobutyl, cyclopentyl, and cyclohexyl.

The term "alkylenyl" as used herein and hereafter, is a divalent group derived from a straight or branched chain hydrocarbon of having suitably 1 to 6 carbon atoms. Representative examples of alkylenyl include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkenyl" as used herein and hereafter is an unsaturated linear or branched hydrocarbon group having at least one olefinic double bond between any two carbon atoms and having the indicated number of carbon atoms, for example $C_{2-6}$-alkenyl has 2 to 6 carbon atoms in the alkenyl moiety, such as ethenyl, propenyl, butenyl, pentenyl, and hexenyl. Examples of preferred alkenyls groups include, but are not limited to, linear alkenyl groups having a terminal double bond such as vinyl and allyl groups.

The term "$C_{2-6}$-alkynyl" as used herein is an unsaturated linear or branched hydrocarbon group having at least one olefinic triple bond between any two carbon atoms, such as ethynyl, propynyl, butynyl, pentynyl, and hexynyl. Examples of preferred alkynyl groups include, but are not limited to, linear alkynyls groups having a terminal triple bond.

The term "$C_{1-6}$-alkoxy" as used herein and hereafter refers to a —O—($C_{1-6}$-alkyl) group where the "$C_{1-6}$-alkyl" has the above-defined meaning. Examples of preferred alkoxy groups include, but are not limited to, methoxy, ethoxy, and iso-propyloxy.

The term "an 5 to 6 membered aliphatic or aromatic heterocyclic ring" refers to a monocyclic ring, which may be aliphatic or aromatic and comprises 1 or 2 heteroatoms each independently selected from N and O while the remaining ring atoms are carbon atoms. Representing groups include pyrrolidinyl, piperidinyl, morpholinyl, and piperazinyl, especially morpholinyl.

The term "an unsaturated or aromatic 5-membered heterocyclic ring" refers to a monocyclic ring which may be aromatic or unsaturated and comprises 1 or 2 heteroatoms each independently selected from N and O, while the remaining ring atoms are carbon atoms. The ring may be optionally substituted one or more times, in particular one time, with methyl at any suitable ring atom, including N, or with oxo at any suitable ring carbon atom. Preferred groups include, but are not limited to, oxazolone or and 1,3-oxazole, optionally substituted with methyl.

The term "optionally substituted" as used herein and hereafter in context of a phenyl group denotes phenyl that is either unsubstituted or substituted independently with one or more, in particular 1, 2, or 3, substituent(s) attached at any available atom to produce a stable compound, e.g. phenyl may be substituted once with a denoted substituent attached to o-, p- or m-position of the phenyl ring. In general "substituted" refers to a substituent group as defined herein in which one or more bonds to a hydrogen atom contained therein are replaced by a bond to a non-hydrogen atom unless otherwise denoted. The substituent groups are each independently selected from the group consisting of halogen, $C_{1-4}$-alkyl, in particular methyl; OH; $C_{1-4}$-alkoxy, in particular methoxy; CN; $NO_2$; and acetoxy. Preferably said phenyl is optionally substituted with acetoxy.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The expression "acid addition salt" includes any non-toxic organic and inorganic acid addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term "acid addition salt" as used herein also comprises solvates which the compounds and salts thereof are able to form, such as, for example, hydrates, alcoholates, and the like. These salts also include salts useful for the chiral resolution of racemates.

The expression "base addition salt" includes any non-toxic base addition salts that the compound of formula (I) can form. Suitable base salts include, but are not limited to, those derived from inorganic bases such as aluminum, ammonium, calcium, copper, iron, lithium, magnesium, manganese, potassium, sodium, and zinc salts, in particular sodium and ammonium salts. Further examples of organic base addition salt include salts of trialkylamines, such as triethyl amine and trimethyl amine, and choline salts.

The present invention relates to estrone C-17 ketimine C-15 thiazole compound having a formula (I)

(I)

[Structure of formula (I) showing steroid with N—R7, R5, R6 substituents, R2, R3, R4 on aromatic ring, and thiazole amide side chain]

wherein (i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_nN(R')_2$, OR', $(CH_2)_nOR'$, $CO_2R'$, CONHR', NHCOR'', C(=NH)R'', C(=N—OH)R'' and COR'';

R3 is selected from the group consisting of H, $C_{1-6}$-alkyl, $C_{1-3}$-haloalkyl, $C_{1-3}$-perhaloalkyl, $NR'_2$, $N_3$, and $OR_3'$, wherein $R_3'$ is selected from the group consisting of R', benzyl, succinyl, optionally acylated glucuronyl, $(CH_2)_nOH$, $SO_2OH$, $SO_2R''$, tosyl, $SO_2N(R')_2$, $PO(OR')_2$, COOR''', $C(O)N(R')_2$, $C(O)(CH_2)_nN(R')_2$, $C(O)CH_2NHC(O)R'$, $C(O)CH_2NHC(O)OR''$ and $C(O)R'''$;

wherein

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R'' is $C_{1-6}$-alkyl, $C_{1-3}$-haloalkyl, or $C_{1-3}$-perhaloalkyl;

R''' is $C_{1-18}$-alkyl, $C_{2-18}$-alkenyl, $—(CH_2)_n-C_{3-6}$-cycloalkyl, or optionally substituted phenyl; and n is 1 or 2; or (i-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(ii-a) R5 and R6 are each H or R5 and R6 form together =CH—OH; and

R7 is selected from the group consisting of ureido or OR7', wherein R7' is selected from the group consisting of H, $C_{1-6}$-alkyl, $C_{3-6}$-alkenyl, R'O—$C_{1-3}$-alkylenyl, R'S—$C_{1-3}$-alkylenyl, $R'_2N$—$C_{1-3}$-alkylenyl, and carboxy- $C_{1-3}$-alkylenyl; or (ii-b) R5 and R6 and =NR7 form together with the carbons they are attached to a structure

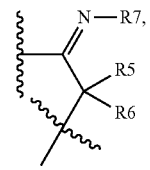

which is selected from

[Structures showing N—OH with OH group and N—X isoxazole/isoxazoline]

wherein X is O or NH;

or a pharmaceutically acceptable salt thereof.

In an aspect of the invention R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_n(R')_2$, C(=N—OH)R'', and C(=N—OMe)R'', wherein R'' is as defined above, in particular $C_{1-4}$-alkyl. In an another aspect of the invention R2 is selected from the group consisting of H, halogen, branched $C_{3-6}$-alkyl, especially tert-butyl, $C_{1-3}$-haloalkyl, especially —$CH_2CF_3$, $C_{1-3}$-perhaloalkyl, especially $CF_3$, CN, $NO_2$, $N_3$, $N(R')_2$, especially $NH_2$, $(CH_2)N(R')_2$, C(=N—OH)Me, and, C(=N—OMe)Me; particularly both R's together with the nitrogen they are attached to may form an 5 to 6 membered aliphatic or aromatic heterocyclic ring comprising 1 or 2 heteroatoms each independently selected from N and O, especially morpholinyl. In yet another aspect of the invention R4 is selected from the group consisting of H, halogen, CN, $NO_2$, and $NH_2$.

In a further aspect of the invention R3 is selected from a group consisting of H, $C_{1-6}$-alkyl, $C_{1-3}$-perhaloalkyl, $N(R')_2$, $N_3$, and OR', especially OH or alkoxy. In an other further aspect of the invention R3 is selected from H, OH and alkoxy, especially methoxy, in particular R3 is OH or methoxy, more particularly OH.

In a particular embodiment of the present invention R7 is selected from the group consisting of R'O—$C_{1-3}$-alkylenyl, R'S—$C_{1-3}$-alkylenyl, and $R'_2N$—$C_{1-3}$-alkylenyl.

In an embodiment of the present invention, the invention relates to a compound of formula (I) wherein R7 is OR7' and which compound has the formula (Ia)

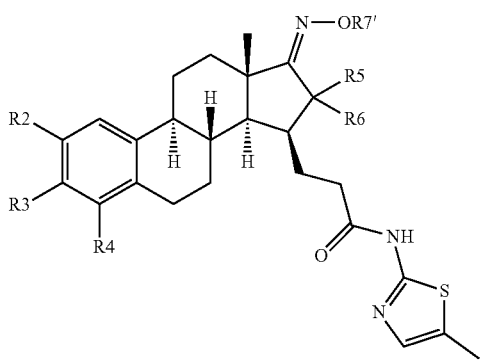

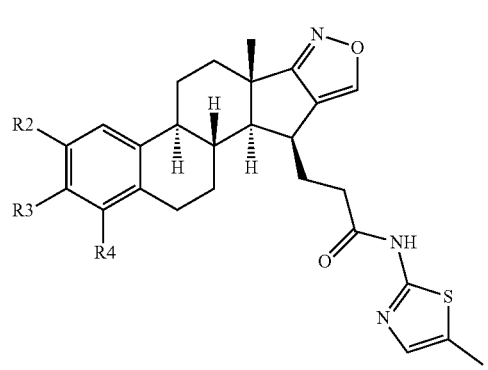

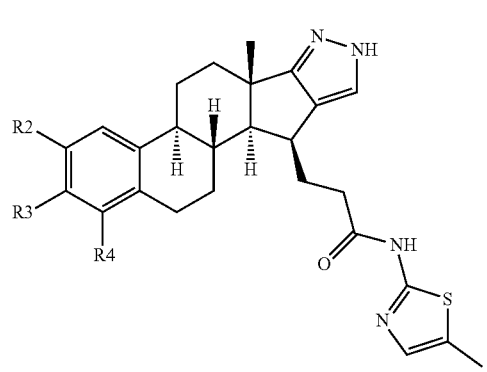

wherein R2, R3, R4, R5 and R6 are as defined above.

In an aspect of this embodiment R7' is selected from the group consisting of H, methyl, ethyl, allyl, and carboxymethylenyl; in particular R7' is H or methyl. In a further aspect of this embodiment R5 and R6 are both H.

In another aspect of this embodiment (i-a) R2 and R4 are each independently selected from the group consisting of H, halogen, branched $C_{3-6}$-alkyl, $C_{1-3}$-haloalkyl, especially —$CH_2CF_3$, $C_{1-3}$-perhaloalkyl, especially $CF_3$, ON, $NO_2$, $N_3$, $N(R')_2$, especially $NH_2$, $(CH_2)_nN(R')_2$, in particular R2 and R4 are each independently selected from the group consisting H, halogen, branched $C_{3-6}$-alkyl, CN, $NO_2$, $NH_2$, $(CH_2)_nN(R')_2$. In a further aspect of this embodiment R3 is H or OR', preferably OR'.

In an alternative aspect of this embodiment (i-b) R2 and R3 or R3 and R4, together with the ring carbon atoms to which they are attached, form an oxazolone or 1,3-oxazole ring, optionally substituted with methyl, and R4 or R2, respectively, is selected from the group consisting of H, F, Cl, Br, and I. In yet a further aspect of this embodiment R5 and R6 are each H or form together a group =CH—OH.

In an another embodiment of the present invention, the invention relates to a compound of formula (I) which compound has the formula (Ib)

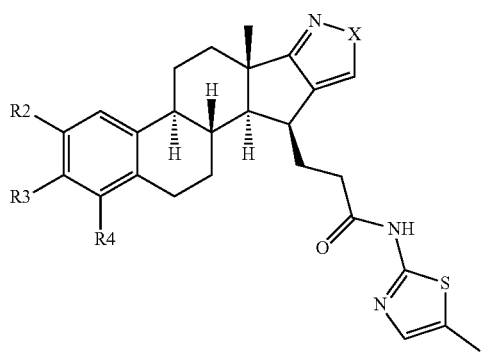

wherein
X is NH or O, and R2, R3 and R4 are as defined above.

A subgroup of this embodiment relates to a compound of formula (Ic) or (Id)

wherein R2, R3 and R4 are as defined above.

In an aspect of this embodiment (i-a) R2 and R4 are each independently selected from the group consisting of H, halogen, branched $C_{3-6}$-alkyl, CN, $NO_2$, $NH_2$, $(CH_2)_nN(R')_2$. In a further aspect of this embodiment R3 is OR', wherein R' and n are as defined above, in particular H or methyl, most particularly H.

In an alternative aspect of this embodiment (i-b) R2 and R3 or R3 and R4, together with the ring carbon atoms to which they are attached, form an oxazolone or 1,3-oxazole ring, optionally substituted with methyl, and R4 or R2, respectively, is selected from the group consisting of H, F, Cl, Br, and I.

In an alternative embodiment of the present invention, the invention relates to a compound of formula (I) or a pharmaceutically acceptable salt thereof, wherein R2 and R3 or R3 and R4, together with the ring carbon atoms to which they are attached, form an unsaturated 5-membered heterocyclic ring; and which compound in particular has the formula (Ie) or (If)

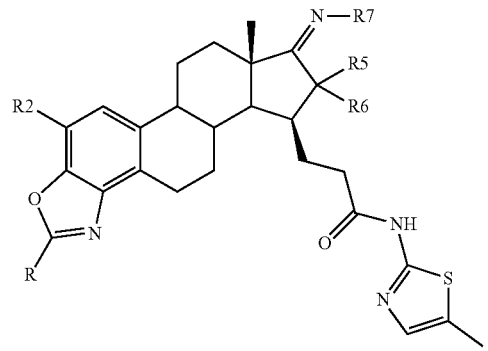

-continued (If)

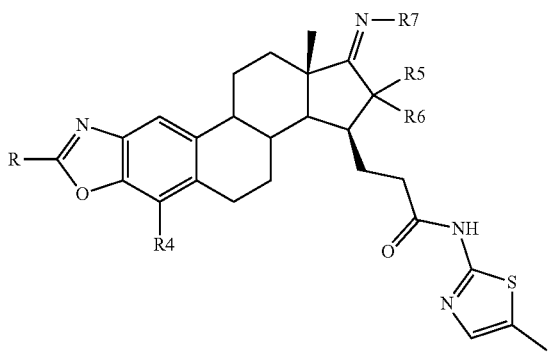

wherein R2 and R4 are as defined above, preferably selected from the group consisting of H, F, Cl, Br, and I, and R is H or methyl. R5 to R7 are as defined above.

In an aspect of the present invention relates to a compound of formula (I) selected from the group consisting of:

Compound 50 3-((6aS,10S)-2-Methoxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 51 3-((6aS,10S)-2-Hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 52 3-((6aS,10S)-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 53 3-((6aS,10S)-3-tert-Butyl-2-hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 54 3-((6aS,10S)-1,3-dibromo-2-hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 55 3-((6aS,10S)-2-Hydroxy-6a-methyl-2-nitro-4b,5,6,6a,8,10,10a,10b,11,12-decehydro-7,8-diaza-pentaleno[2,1-1]phenanthren-10-yl}-N-(5-methylthiazol-2-yl)propanamide;

Compound 56 3-((6aS,10S)-2-Hydroxy-6a-methyl-4-nitro-4b,5,6,6a,8,10,10a,10b,11,12-decehydro-7,8-diaza-pentaleno[2,1-1]phenanthren-10-yl}-N-(5-methylthiazol-2-yl)propanamide;

Compound 57 3-{(13S,15R)-3-Hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 58 3-{(13S,15R)-2-tert-Butyl-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 59 3-{(13S,15R)-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 60 3-{(13S,15R)-3-Hydroxy-2-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 61 3-{(13S,15R)-3-Hydroxy-4-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 62 3-{(13S,15R)-2-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 63 3-{(13S,15R)-4-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 64 3-{(13S,15R)-2,4-Dibromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 65 3-{(13S,15R)-2-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 66 3-{(13S,15R)-4-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 67 3-{(13S,15R)-2,4-Dichloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 68 3-{(13S,15R)-2-Fluoro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 69 3-{(13S,15S)-3-Hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 70 3-{(13S,15S)-2,4-Dibromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 71 3-{(13S,15S)-4-Bromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 72 3-{(13S,15R)-17-[(E)-hydroxyimino]-2-{1-[(E)-hydroxyimino]-ethyl}]-3-methoxy-13-methyl-7,8,9,11,12,13,14,15,16,17-decahydro-6H-cyclopenta[a]phenanthren-15-yl}-N-(5-methylthiazol-2-yl)propanamide;

Compound 73 3-{(13S,15R)-3-Hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 74 3-{(13S,15R)-3-Methoxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 75 3-{(13S,15R)-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 76 3-{(13S,15R)-2-tert-Butyl-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 77 3-{(13S,15R)-3-Hydroxy-17-[(E)-methoxyimino]-13-methyl-2-nitro-7,8,9,11,12,13,14,15,16,17-decahydro-6H-cyclopenta[a]phenanthren-15-yl}-N-(5-methylthiazol-2-yl)propanamide;

Compound 78 3-{(13S,15R)-2-Amino-3-hydroxy-17-[(E)-methoxyimino]-13-methyl-7,8,9,11,12,13,14,15,16,17- decahydro-6H-cyclopenta[a]phenanthren-15-yl}-N-(5-methylthiazol-2-yl)propanamide;

Compound 79 3-{(13S,15R)-3-Hydroxy-17-[(E)-methoxyimino]-13-methyl-4-nitro-7,8,9,11,12,13,14,15,16,17-decahydro-6H-cyclopenta[a]phenanthren-15-yl}-N-(5-methylthiazol-2-yl)propanamide;

Compound 80 3-{(13S,15R)-4-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 81 3-{(13S,15R)-3-Hydroxy-2-iodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 82 3-{(13S,15R)-3-Hydroxy-4-iodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 83 3-{(13S,15R)-3-Hydroxy-2,4-diiodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 84 3-{(13S,15R)-2-iodo-3-methoxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 85 3-{(13S,15R)-2-Bromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 86 3-{(13S,15R)-4-Bromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 87 3-{(13S,15R)-2,4-Dibromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 88 3-{(13S,15R)-2-Chloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 89 3-{(13S,15R)-4-Chloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 90 3-{(13S,15R)-2,4-Dichloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 91 3-{(13S,15R)-2-Fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 92 3-{(13S,15R)-4-Fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 93 3-{(13S,15R)-2-Bromo-4-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 94 3-{(13S,15R)-4-Bromo-2-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 95 3-{(13S,15R)-3-hydroxy-17-[(E)-methoxyimino]-13-methyl-2-nitrile-7,8,9,11,12,13,14,15,16,17-decahydro-6H-cyclopenta[a]phenanthren-15-yl}-N-(5-methylthiazol-2-yl)propanamide;

Compound 96 3-{(13S,15R)-3-hydroxy-17-[(E)-methoxyimino]-13-methyl-4-nitrile-7,8,9,11,12,13,14,15,16,17-decahydro-6H-cyclopenta[a]phenanthren-15-yl}-N-(5-methylthiazol-2-yl)propanamide;

Compound 97 3-{(13S,15R)-3-Methoxy-17-[(E)-methoxyimino]-2-{1-[(E)-methoxyimino]-ethyl}-13-methyl-7,8,9,11,12,13,14,15,16,17-decahydro-6H-cyclopenta[a]phenanthren-15-yl}-N-(5-methylthiazol-2-yl)propanamide;

Compound 98 3-{(13S,15R)-3-Hydroxy-17-[(E)-methoxyimino]-13-methyl-2-morpholin-4-ylmethyl-7,8,9,11,12,13,14,15,16,17-decahydro-6H-cyclopenta[a]phenanthren-15-yl}-N-(5-methylthiazol-2-yl)propanamide;

Compound 99 3-{(13S,15R)-3-Hydroxy-17-[(E)-methoxyimino]-13-methyl-2-morpholin-4-ylmethyl-4-nitro-7,8,9,11,12,13,14,15,16,17-decahydro-6H-cyclopenta[a]phenanthren-15-yl}-N-(5-methylthiazol-2-yl)propanamide;

Compound 100 Acetic acid (13S,15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 101 Dimethylamino-acetic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 102 Sulphamic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 103 Dimethyl-sulfamic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 104 Methanesulphonic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 105 3-{(13S,15R)-17-[(E)-Ethoxyimino]-3-hydroxy-13-methyl-7,8,9,11,12,13,14,15,16,17-decahydro-6H-cyclopenta[a]phenanthren-15-yl}-N-(5-methylthiazol-2-yl)propanamide;

Compound 106 3-{(13S,15R)-2-tert-Butyl-17-[(E)-ethoxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide;

Compound 107 3-{(13S,15R)-17-[(E)-Allyloxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide;

Compound 108 3-{(13S,15R)-17-[(E)-Allyloxyimino]-3-hydroxyl-13-methyl-2-nitro-7,8,9,11,12,13,14,15,16,17-decahydro-6H-cyclopenta[a]phenanthren-15-yl}-N-(5-methylthiazol-2-yl)propanamide;

Compound 109 [(13S,15R)-3-Hydroxy-13-methyl-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid;

Compound 110 [(13S,15R)-2-tert-Butyl-3-hydroxy-13-methyl-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid;

Compound 111 [(13S,15R)-3-Hydroxy-13-methyl-2-nitro-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid;

Compound 112 3-{(13S,15R)-3-Hydroxy-17-[(E)-N-urea-imino]-13-methyl-7,8,9,11,12,13,14,15,16,17-decahydro-6H-cyclopenta[a]phenanthren-15-yl}-N-(5-methylthiazol-2-yl)propanamide;

Compound 113 3-{(13S,15R)-2,4-Dibromo-3-hydroxy-17-[(E)-N-urea-imino]-13-methyl-7,8,9,11,12,13,14,15,16,17-decahydro-6H-cyclopenta[a]phenanthren-15-yl}-N-(5-methylthiazol-2-yl)propanamide;

Compound 114 3-{(7aS,10OR)-8-[(E)-Hydroxyimino]-7a-methyl-6,7,7a,8,9,10,10a,10b,11,12-decahydro-5bH-3-oxa-1-aza-dicyclopenta[a,i]phenathren-10-yl}-N-(5-methylthiazol-2-yl)propanamide;

Compound 115 3-{(7aS,10OR)-8-[(E)-Methoxyimino]-7a-methyl-6,7,7a,8,9,10,10a,10b,11,12-decahydro-5bH-3-oxa-1-aza-dicyclopenta[a,i]phenanthren-10-yl}-N-(5-methylthiazol-2-yl)propanamide;

Compound 116 3-{(3R,12aS)-1-[(E)-Methoxyimino]-1a-methyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide;

Compound 117 3-{(3R,12aS)-6-Chloro-1-[(E)-methoxyimino]-12a-methyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide;

Compound 118 3-{(3R,12aS)-1-[(E)-Methoxyimino]-8,12a-dimethyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide;

Compound 119 3-((6aS,10S)-1,3-Dibromo-2-hydroxy-6a-methyl-4-nitro-4b,6,6a,10,10a,10b,11,12-octahydro-5H-8-oxa-7-aza-pentaleno[2,1-a]phenanthren-10-yl}-N-(5-methylthiazol-2-yl)propanamide; and Compound 120 Methanesulphonic acid (6aS,10S)-6a-methyl-10-[2-(5-methylthiazol-2-ylcarbamoyl)-ethyl]-4b,6,6a,10,10a,10b,11,12-octahydro-5H-8-oxa-7-aza-pentaleno[2,1-a]phenanthren-2-yl ester;

or a pharmaceutically acceptable salt thereof.

In an further aspect of the present invention the present invention relates to a compound of formula (I) selected from the group consisting of:

Compound 58 3-{(13S,15R)-2-tert-Butyl-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 59 3-{(13S,15R)-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 63 3-{(13S,15R)-4-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 64 3-{(13S,15R)-2,4-Dibromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 65 3-{(13S,15R)-2-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 66 3-{(13S,15R)-4-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 68 3-{(13S,15R)-2-Fluoro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 70 3-{(13S,15S)-2,4-Dibromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 73 3-{(13S,15R)-3-Hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 76 3-{(13S,15R)-2-tert-Butyl-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 91 3-{(13S,15R)-2-Fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)-propanamide; and Compound 92 3-{(13S,15R)-4-Fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)-propanamide;

or a pharmaceutically acceptable salt thereof.

EXAMPLES OF THE INVENTION

Representative examples of compounds of formula (I) are shown in Table 1.

TABLE 1

| # | Compound | NMR |
|---|----------|-----|
| 50 | 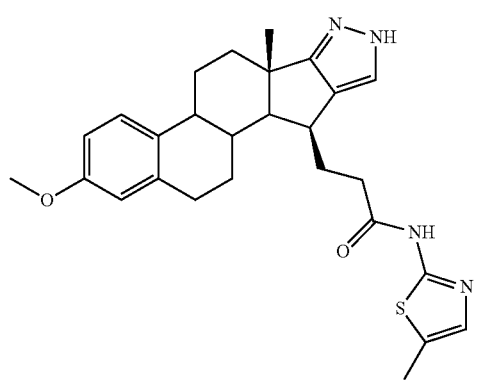 [SMILES: COc1ccc2c(c1)CCC1C2CC[C@]2(C)c3n[nH]cc3[C@@H](CCC(=O)Nc3ncc(C)s3)C12] | $^1$H-NMR (DMSO-d$_6$ + CDCl$_3$): 1.11 (t, 3H), 1.25-2.40 (m, 16H), 2.86 (m, 3H), 3.70 (s, 3H), 6.60 (s, 1H), 6.62 (d, 1 H), 7.02 (s, 1H), 7.11 (d, 1H), 7.30 (s, 1H), 11.86 (s, 1H), 12.00 (br s, 1H). |

TABLE 1-continued

| # | Compound | NMR |
|---|---|---|
| 51 | | ¹H-NMR (DMSO-d₆): 1.08 (s, 3H), 1.22-2.32 (m, 16H), 2.65-2.90 (m, 3H), 6.47-6.52 (m, 2H), 7.03-7.10 (m, 2H), 7.35 (s, 1H), 9.05 (s, 1H), 11.94 (s, 1H), 12.12 (s, 1H). |
| 52 | | ¹H-NMR (CDCl₃): 1.11 (s, 3H), 1.30-3.10 (m, 19H), 5.74 (s, 1H), 6.56 (s, 1H), 7.0-7.30 (m, 5H), 12.39 (br s, 1H). |
| 53 | | ¹H-NMR (CDCl₃ + MeOH-d₄): 1.20 (s, 3H), 1.32-3.15 (m, 28H), 6.48 (s, 1H), 6.98 (s, 1H), 7.18 (s, 1H), 7.22 (s, 1H). |
| 54 | | ¹H-NMR (DMSO-d₆): 1.08 (s, 3H), 1.10-2.40 (m, 19H), 2.65-2.90 (m, 3H), 7.12 (s, 1H), 7.37 (s, 1H), 7.41 (s, 1H), 9.54 (s, 1H), 11.95 (br s, 1H), 12.15 (br s, 1H). |

TABLE 1-continued
| # | Compound | NMR |
|---|---|---|
| 55 | 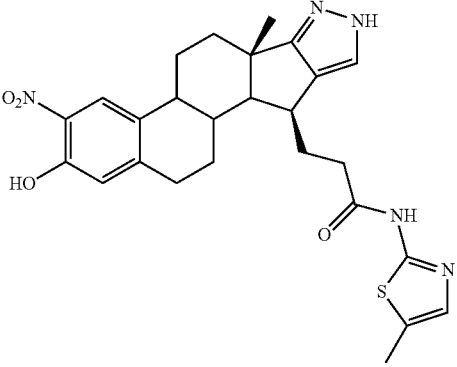 [SMILES: Cc1cnc(NC(=O)CC[C@@H]2c3c[nH]nc3[C@@]3(C)CCC4c5cc([N+](=O)[O-])c(O)cc5CCC4C23)s1] | $^1$H-NMR (CDCl$_3$ + MeOH-d$_4$): 1.24 (s, 3H), 1.45-2.70 (m, 16H), 2.90-3.10 (m, 3H), 6.91 (s, 1H), 7.04 (s, 1H), 7.36 (s, 1 H), 8.00 (s, 1H). |
| 56 | 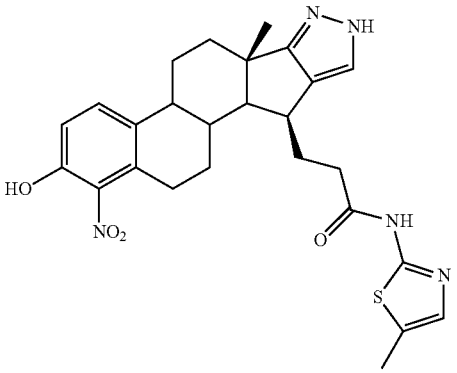 [SMILES: Cc1cnc(NC(=O)CC[C@@H]2c3c[nH]nc3[C@@]3(C)CCC4c5ccc(O)c([N+](=O)[O-])c5CCC4C23)s1] | $^1$H-NMR (CDCl$_3$ + MeOH-d$_4$): 1.22 (s, 3H), 1.40-3.10 (m, 19H), 6.86 (d, 1H), 7.02 (s, 1H), 7.25-7.40 (m, 2H). |
| 57 | 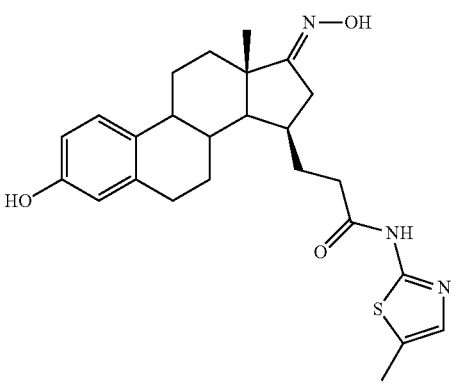 [SMILES: Cc1cnc(NC(=O)CC[C@@H]2C/C(=N\O)[C@@]3(C)CCC4c5ccc(O)cc5CCC4C23)s1] | $^1$H-NMR (DMSO-d$_6$): 1.02 (s, 3H), 1.2-2.9 (m, 21H), 6.46 (s, 1H), 6.50 (d, 3H), 7.04 (d, 1H), 7.12 (s, 1H), 9.02 (s, 1H ), 10.18 (s, 1H), 11.92(s, 1H). |
| 58 | 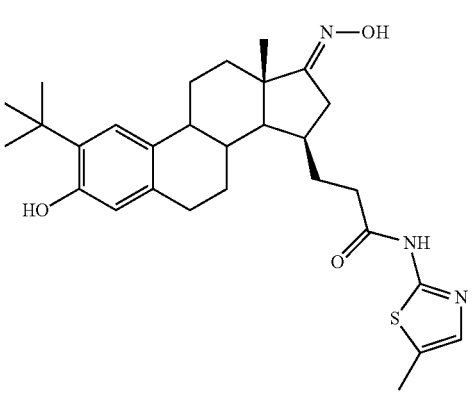 [SMILES: Cc1cnc(NC(=O)CC[C@@H]2C/C(=N\O)[C@@]3(C)CCC4c5cc(C(C)(C)C)c(O)cc5CCC4C23)s1] | $^1$H-NMR (CDCl$_3$ + MeOH-d$_4$): 1.11 (s, 3H), 1.3-3.1 (m, 34H), 6.46 (s, 1H), 7.05 (s, 1H,), 7.15 (s, 1H). |

US 9,663,549 B2
TABLE 1-continued
| # | Compound | NMR |
|---|----------|-----|
| 59 | 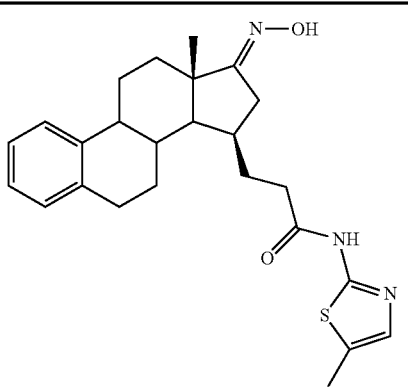 | ¹H-NMR (CDCl₃): 1.14 (s, 3H), 1.35-2.75 (m, 18H), 2.80-3.05 (m, 3H), 7.05-7.40 (m, 5H), 8.35 (s, 1H ), 11.48 (s, 1H). |
| 60 | 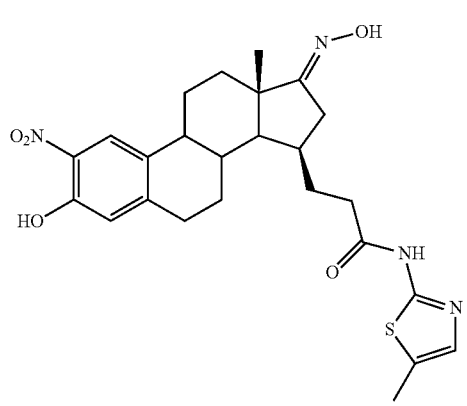 [SMILES: Cc1cnc(NC(=O)CC[C@@H]2C/C(=N\O)[C@@]3(C)CCC4c5cc([N+](=O)[O-])c(O)cc5CCC4C23)s1] | ¹H-NMR (CDCl₃): 1.15 (s, 3H), 1.30-2.75 (m, 18H), 2.85-3.05 (m, 3H), 6.87 (s, 1H), 7.06 (s, 1H) , 7.97 (s, 1H) 8.50 (br s, 1H), 10.55 (br s, 1H). |
| 61 | 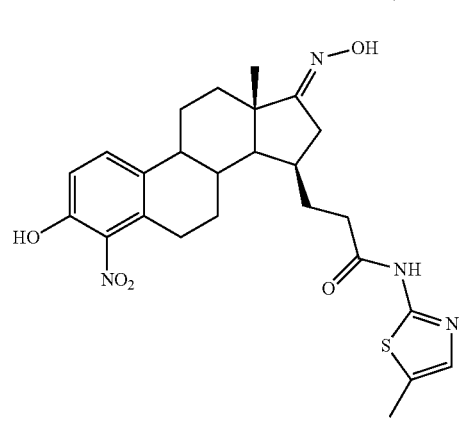 [SMILES: Cc1cnc(NC(=O)CC[C@@H]2C/C(=N\O)[C@@]3(C)CCC4c5ccc(O)c([N+](=O)[O-])c5CCC4C23)s1] | 1H-NMR (CDCl₃ + MeOH-d₄): 1.11 (s, 3H), 1.2-3.0 (m, 18H), 2.40 (s, 3H), 6.69 (s, 1H), 7.04 (s, 1H), 7.32 (d, 1H). |
| 62 | 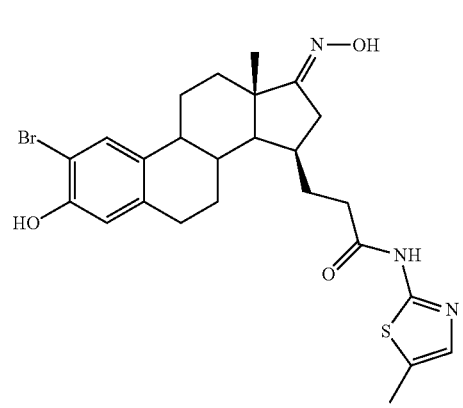 [SMILES: Cc1cnc(NC(=O)CC[C@@H]2C/C(=N\O)[C@@]3(C)CCC4c5cc(Br)c(O)cc5CCC4C23)s1] | 1H-NMR (CDCl₃ + MeOH-d₄): 1.11 (s, 3H), 1.2-3.0 (m, 18H), 2.41 (s, 3H), 6.82 (d, 1H), 7.06 (s, 1H), 7.14 (d, 1H). |

TABLE 1-continued
| # | Compound | NMR |
|---|----------|-----|
| 63 | 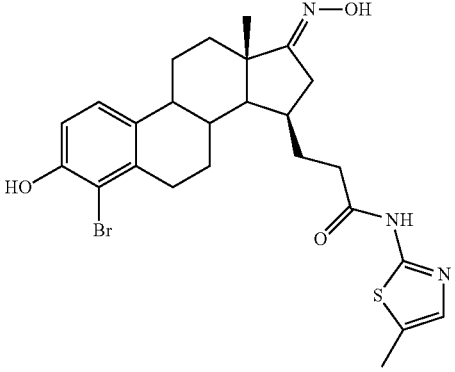 [SMILES: Cc1cnc(NC(=O)CC[C@@H]2C/C(=N\O)[C@@]3(C)CCC4c5ccc(O)c(Br)c5CCC4C23)s1] | 1H-NMR (CDCl₃ + MeOH-d₄): 1.11 (s, 3H), 1.2-3.0 (m, 18H), 2.41 (s, 3H), 6.82 (d, 1H), 7.06 (s, 1H), 7.14 (d, 1H). |
| 64 | 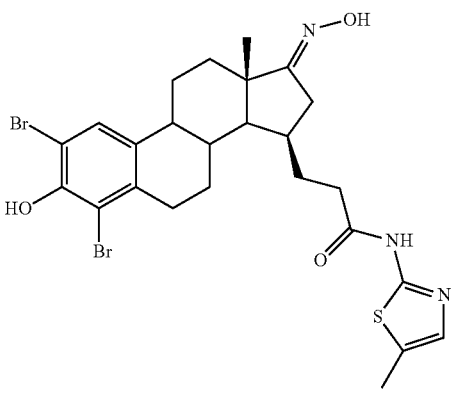 [SMILES: Cc1cnc(NC(=O)CC[C@@H]2C/C(=N\O)[C@@]3(C)CCC4c5cc(Br)c(O)c(Br)c5CCC4C23)s1] | ¹H-NMR (DMSO-d₆): 1.00 (s, 3H), 1.25-2.95 (m, 21H), 7.11 (s, 1H) 7.40 (s, 1H), 9.54 (s, 1H), 10.20 (s, 1H), 11.93 (s, 1H). |
| 65 | 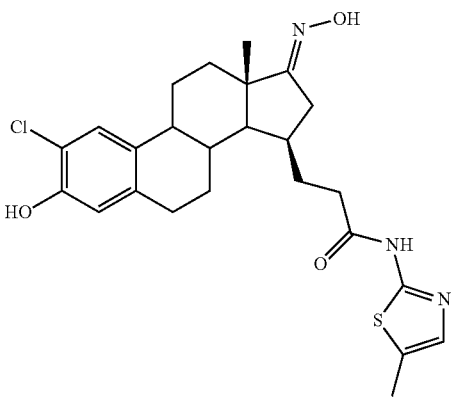 [SMILES: Cc1cnc(NC(=O)CC[C@@H]2C/C(=N\O)[C@@]3(C)CCC4c5cc(Cl)c(O)cc5CCC4C23)s1] | ¹H-NMR (CDCl₃): 1.10 (s, 3H), 1.30-3.0 (m, 21H), 6.69 (s, 1H), 7.04 (s, 1H), 7.17 (s, 1H). |
| 66 | 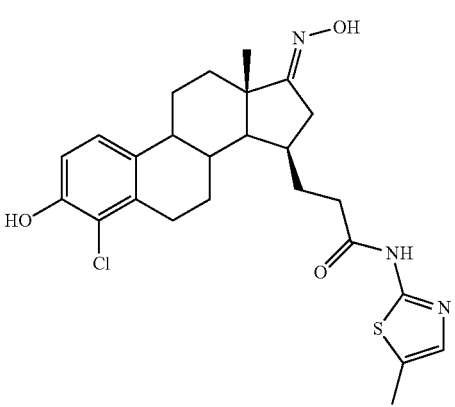 [SMILES: Cc1cnc(NC(=O)CC[C@@H]2C/C(=N\O)[C@@]3(C)CCC4c5ccc(O)c(Cl)c5CCC4C23)s1] | ¹H-NMR (CDCl₃): 1.10 (s, 3H), 1.30-3.05 (m, 21H), 6.80 (d, 1H), 7.05 (s, 1H), 7.08 (d, 1H). |

TABLE 1-continued
| # | Compound | NMR |
|---|---|---|
| 67 | 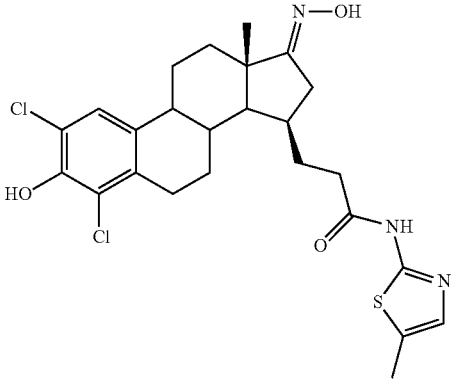 [SMILES: Cc1cnc(NC(=O)CC[C@@H]2C/C(=N\O)[C@@]3(C)CCC4c5cc(Cl)c(O)c(Cl)c5CCC4C23)s1] | 1H-NMR (CDCl$_3$ + MeOH-d$_4$): 1.11 (s, 3H), 1.4-3.0 (m, 18H), 2.39 (s, 3H), 7.03 (s, 1H), 7.19 (s, 1H). |
| 68 | 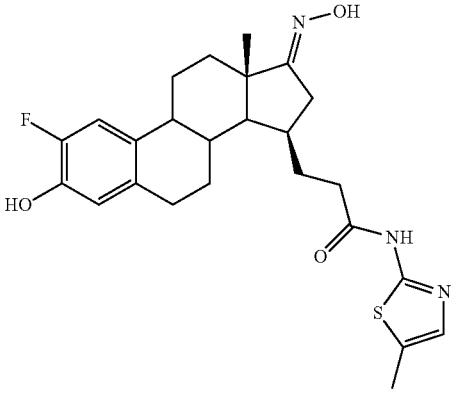 [SMILES: Cc1cnc(NC(=O)CC[C@@H]2C/C(=N\O)[C@@]3(C)CCC4c5cc(F)c(O)cc5CCC4C23)s1] | $^1$H-NMR (CDCl$_3$ + MeOH-d$_4$): 1.10 (s, 3H), 1.25-3.0 (m, 21H), 6.66 (d, J = 10 Hz, 1H), 6.92 (d, J = 12 Hz, 1H), 7.04 (br s, 1H). |
| 69 | 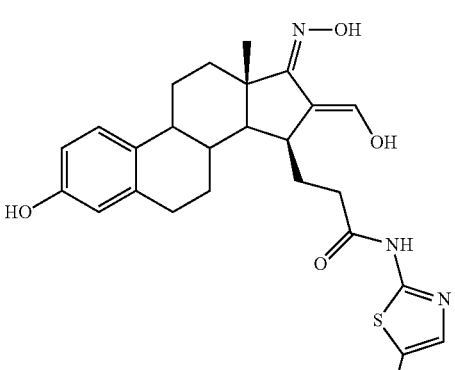 | $^1$H-NMR (DMSO-d$_6$): 1.01 (s, 3H), 1.05-2.80 (m, 21H), 6.44 (s, 1H), 6.49 (d, 1H) 6.70 (s, 1H), 7.03 (d, 1H), 7.12 (s, 1H) 7.28 (s, 1H), 9.01 (s, 1H ), 11.98 (s, 1H). |
| 70 | 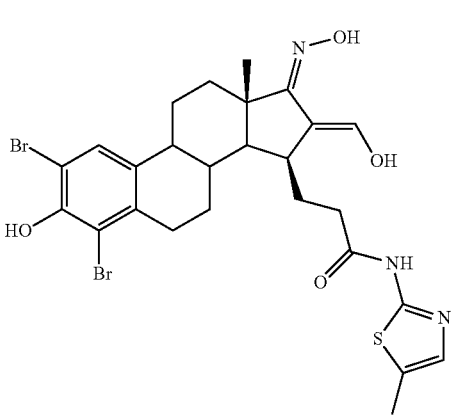 [SMILES: Cc1cnc(NC(=O)CC[C@@H]2C(=C\O)/C(=N\O)[C@@]3(C)CCC4c5cc(Br)c(O)c(Br)c5CCC4C23)s1] | $^1$H-NMR (DMSO-d$_6$): 1.01 (s, 3H), 1.0-2.8 (m, 19H), 6.72 (s, 1H) 7.13 (s, 1H) 7.29 (s, 1H) 7.40 (s, 1H), 9.53 (s, 1H ), 11.98 (br s, 1H). |

| # | Compound | NMR |
|---|---|---|
| 71 | 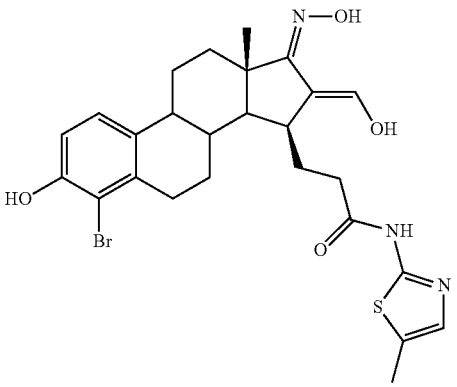 [SMILES: Cc1cnc(NC(=O)CC[C@@H]2C(=C\O)/C(=N\O)[C@@]3(C)CCC4c5ccc(O)c(Br)c5CCC4C23)s1] | 1H-NMR (CDCl$_3$): 1.14 (s, 3H), 1.3-2.9 (m, 16H), 2.41 (s, 3H), 3.25 (s, 1H), 6.85 (d, 1H), 7.05 (s, 1H), 7.15 (d, 1H). |
| 72 | 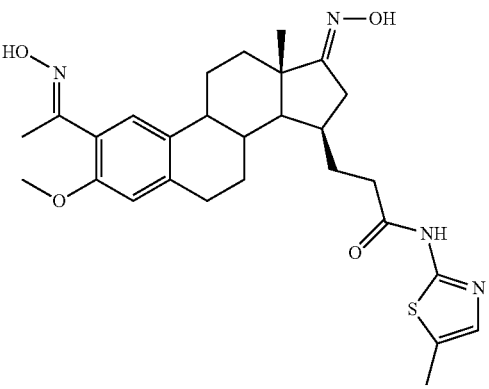 [SMILES: COc1cc2c(cc1/C(C)=N/O)C1CC[C@]3(C)/C(=N/O)C[C@@H](CCC(=O)Nc4ncc(C)s4)C3C1CC2] | $^1$H-NMR (CDCl$_3$): 1.05 (s, 3H), 1.20-3.10 (m, 24H), 3.82 (s, 3H), 6.69 (s, 1H), 7.08 (s, 1H), 7.14 (s, 1H), 11.60 (br, 1H). |
| 73 | 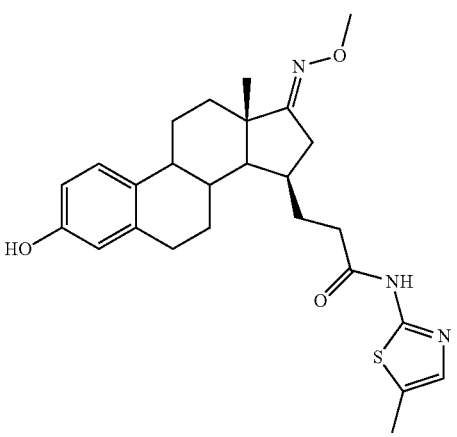 [SMILES: CO/N=C1\C[C@@H](CCC(=O)Nc2ncc(C)s2)C2C3CCc4cc(O)ccc4C3CC[C@]12C] | $^1$H-NMR (CDCl$_3$): 1.09 (s, 3H), 1.15-2.90 (m, 21H), 3.84 (s, 3H), 6.57-6.66 (m, 2H), 7.00-7.15 (m, 2H). |

TABLE 1-continued
| # | Compound | NMR |
|---|----------|-----|
| 74 | 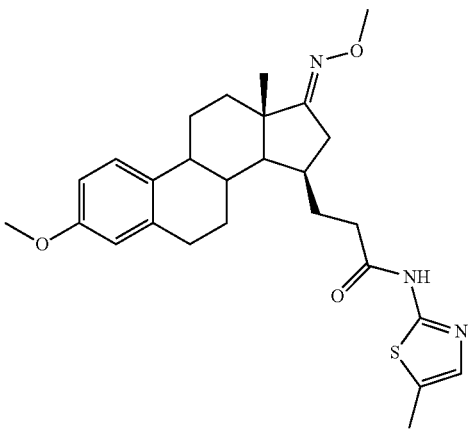 [SMILES: CO/N=C1\C[C@@H](CCC(=O)Nc2ncc(C)s2)C2C3CCc4cc(OC)ccc4C3CC[C@]12C] | ¹H-NMR (CDCl₃): 1.10 (s, 3H), 1.20-3.00 (m, 21H), 3.78 (s, 3H), 3.84 (s, 3H), 6.63-6.74 (m, 2H), 7.07-7.22 (m, 2H). |
| 75 | 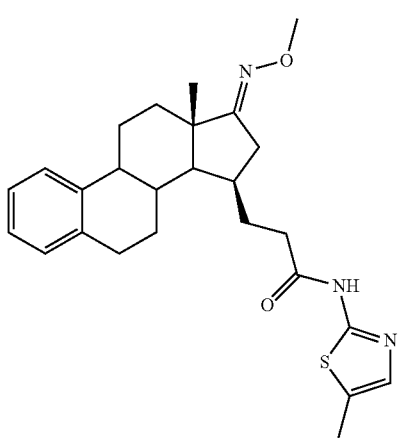 [SMILES: CO/N=C1\C[C@@H](CCC(=O)Nc2ncc(C)s2)C2C3CCc4ccccc4C3CC[C@]12C] | ¹H-NMR (CDCl₃): 1.11 (s, 3H), 1.20-3.00 (m, 21H), 3.85 (s, 3H), 7.0-7.4 (m, 5H), 12.2 (s, 1H). |
| 76 | 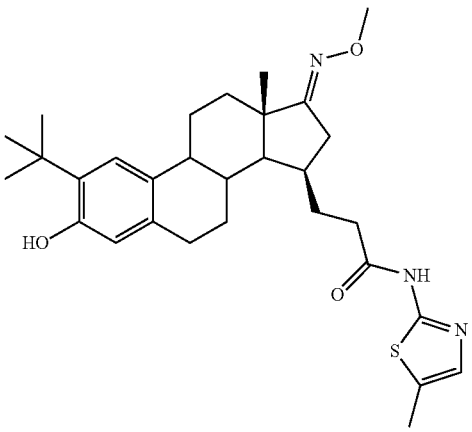 [SMILES: CO/N=C1\C[C@@H](CCC(=O)Nc2ncc(C)s2)C2C3CCc4cc(O)c(C(C)(C)C)cc4C3CC[C@]12C] | ¹H-NMR (CDCl₃ + MeOH-d₄): 1.09 (s, 3H), 1.3-2.9 (m, 33H), 3.85 (s, 3H), 6.43 (s, 1H) 7.07 (s, 1H), 7.17 (s, 1H), 12.34 (br, 1H). |

TABLE 1-continued
| # | Compound | NMR |
|---|---|---|
| 77 | 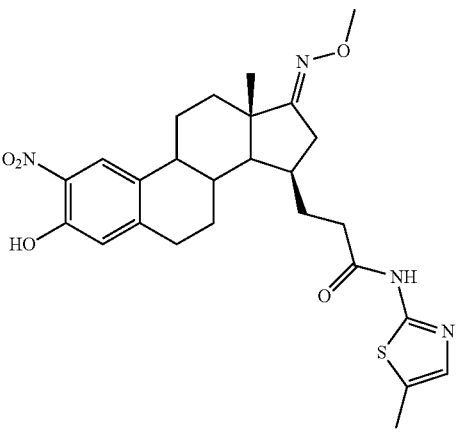 | ¹H-NMR (CDCl$_3$): 1.11 (s, 3H), 1.40-3.05 (m, 21H), 3.85 (s, 3H), 6.87 (s, 1H), 7.07 (s, 1H), 7.98 (s, 1H) 10.57 (br s, 1H), 11.91 (br s, 1H). |
| 78 | 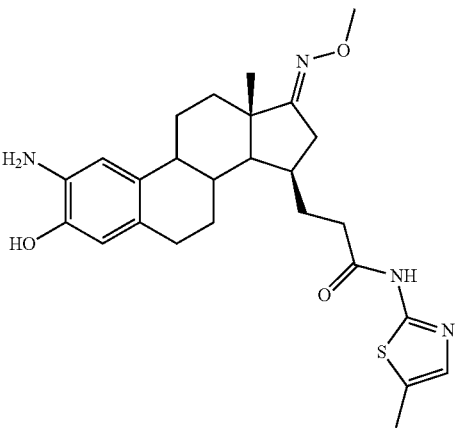 | ¹H-NMR (CDCl$_3$): 1.04 (s, 3H), 1.25-2.90 (m, 21H), 3.84 (s, 3H), 6.47 (s, 1H), 6.68 (s, 1H), 7.05 (s, 1H). |
| 79 | 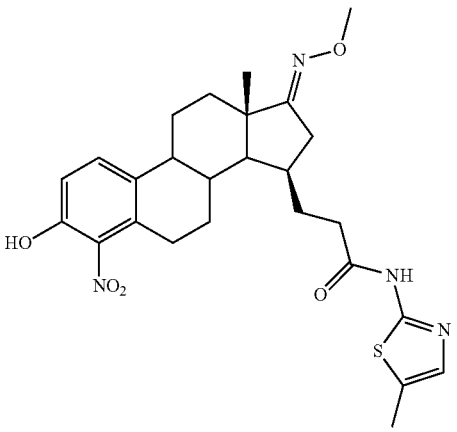 [SMILES: CO/N=C1\C[C@@H](CCC(=O)Nc2ncc(C)s2)C2C3CCc4c(ccc(O)c4[N+](=O)[O-])C3CC[C@]12C] | ¹H-NMR (CDCl$_3$): 1.12 (s, 3H), 1.20-3.35 (m, 21H), 6.96 (d, 1H), 7.07 (s, 1H), 7.48 (d, 1H). |

| # | Compound | NMR |
|---|---|---|
| 80 | 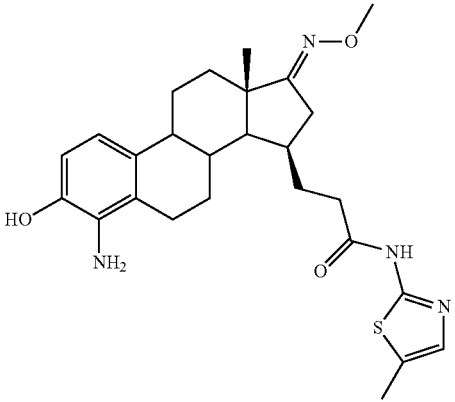 [SMILES: CO/N=C1\C[C@@H](CCC(=O)Nc2ncc(C)s2)C2C3CCc4c(ccc(O)c4N)C3CC[C@]12C] | ¹H-NMR (CDCl₃): 1.04 (s, 3H), 1.20-2.95 (m, 21H), 3.84 (s, 3H), 6.58 (AB, 2H), 7.08 (s, 1H). |
| 81 | 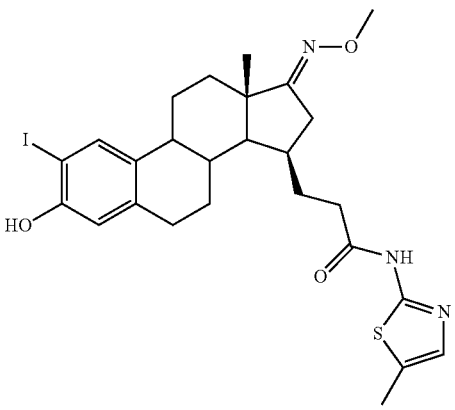 [SMILES: CO/N=C1\C[C@@H](CCC(=O)Nc2ncc(C)s2)C2C3CCc4cc(O)c(I)cc4C3CC[C@]12C] | ¹H-NMR (CDCl₃): 1.09 (s, 3H), 1.20-2.90 (m, 21H), 3.84 (s, 3H), 6.72 (s, 1H), 7.07 (s, 1H), 7.51 (s, 1H). |
| 82 | 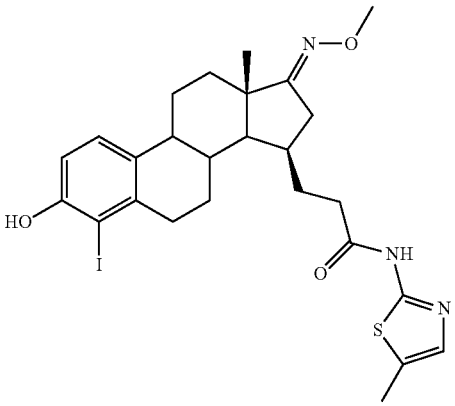 [SMILES: CO/N=C1\C[C@@H](CCC(=O)Nc2ncc(C)s2)C2C3CCc4c(ccc(O)c4I)C3CC[C@]12C] | ¹H-NMR (CDCl₃): 1.09 (s, 3H), 1.30-2.95 (m, 21H), 3.85 3H), 6.83 1H), 7.08 (s, 1H), 7.19 (d, 1H). |

TABLE 1-continued
| # | Compound | NMR |
|---|----------|-----|
| 83 | 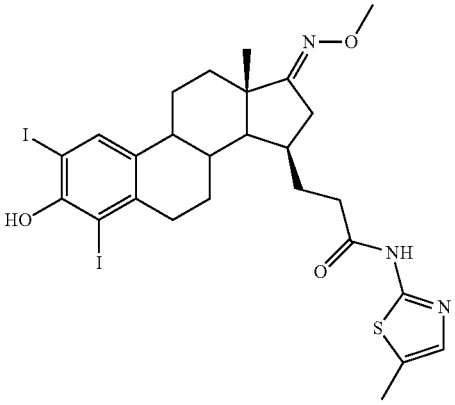 [SMILES: CO/N=C1\C[C@@H](CCC(=O)Nc2ncc(C)s2)C2C3CCc4c(cc(I)c(O)c4I)C3CC[C@]12C] | $^1$H-NMR (CDCl$_3$): 1.09 (s, 3H), 1.23-2.96 (m, 21H), 3.85 (s, 3H), 7.61 (s, 1H), 7.08 (s, 1H). |
| 84 | 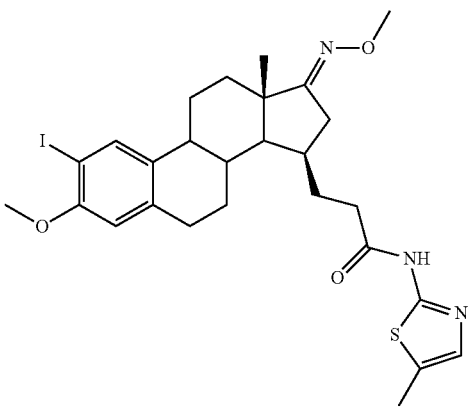 [SMILES: CO/N=C1\C[C@@H](CCC(=O)Nc2ncc(C)s2)C2C3CCc4cc(OC)c(I)cc4C3CC[C@]12C] | $^1$H-NMR (DMSO-d$_6$): 1.03 (s, 3H), 1.10-3.00 (m, 21H), 3.72 (s, 3H), 3.77 (s, 3H), 6.72 (s, 1H), 7.11 (s, 1H), 7.55 (s, 1H), 11.91 (s, 1H). |
| 85 | 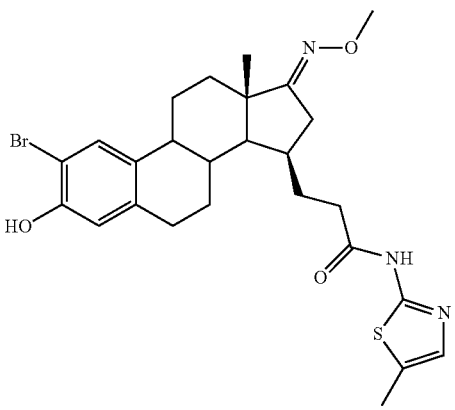 [SMILES: CO/N=C1\C[C@@H](CCC(=O)Nc2ncc(C)s2)C2C3CCc4cc(O)c(Br)cc4C3CC[C@]12C] | $^1$H-NMR (DMSO-d$_6$): 1.03 (s, 3H), 1.2-3.0 (m, 18H), 2.33 (s, 3H), 3.73 (s, 3H), 6.65 (s, 1H), 7.11 (s, 1H), 7.27 (d, 1H), 9.86 (s, 1H), 11.91 (s, 1H). |

TABLE 1-continued
| # | Compound | NMR |
|---|---|---|
| 86 | 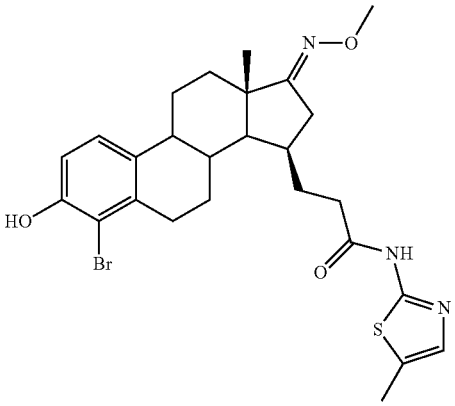 [SMILES: CO/N=C1\C[C@@H](CCC(=O)Nc2ncc(C)s2)C2C3CCc4c(ccc(O)c4Br)C3CC[C@]12C] | $^1$H-NMR (DMSO-d$_6$): 1.02 (s, 3H), 1.2-2.9 (m, 18H), 2.33 (s, 3H), 3.73 (s, 3H), 6.76 (m, 1H), 7.12 (m, 2H), 9.89 (s, 1H), 11.92 (s, 1H). |
| 87 | 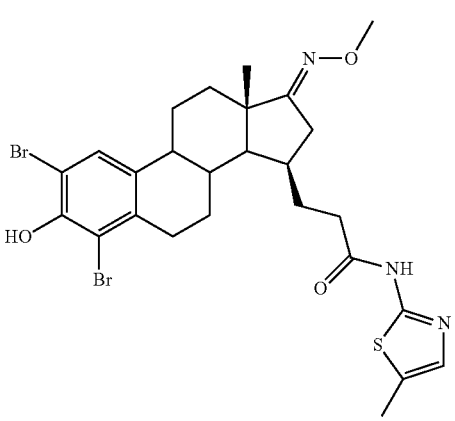 [SMILES: CO/N=C1\C[C@@H](CCC(=O)Nc2ncc(C)s2)C2C3CCc4c(cc(Br)c(O)c4Br)C3CC[C@]12C] | $^1$H-NMR (DMSO-d$_6$): 1.01 (s, 3H), 1.10-2.90 (m, 21H), 3.72 (s, 3H), 7.11 (s, 1H), 7.40 (s, 1H), 9.54 (s, 1H), 11.91 (s, 1H). |
| 88 | 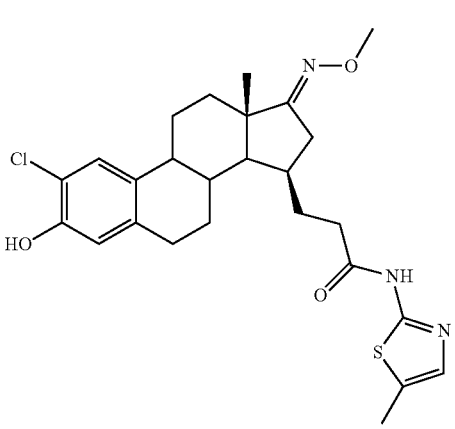 | $^1$H-NMR (CDCl$_3$): 1.09 (s, 3H), 1.25-2.92 (m, 21H), 3.84 (s, 3H), 6.73 (s, 1H), 7.07 (s, 1H), 7.19 (s, 1H). |

TABLE 1-continued
| # | Compound | NMR |
|---|---|---|
| 89 | 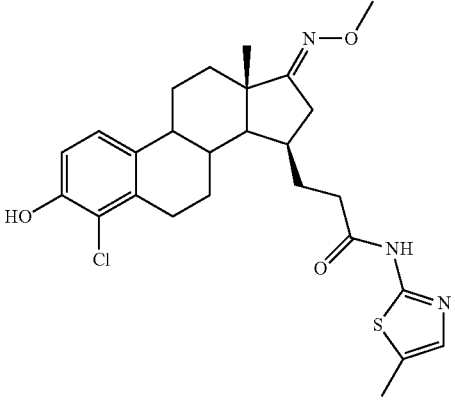 | $^1$H-NMR (CDCl$_3$): 1.09 (s, 3H), 1.25-3.05 (m, 21H), 3.84 (s, 3H) 6.84 (d, 1H), 7.07 (s, 1H), 7.12 (d, 1H). |
| 90 | 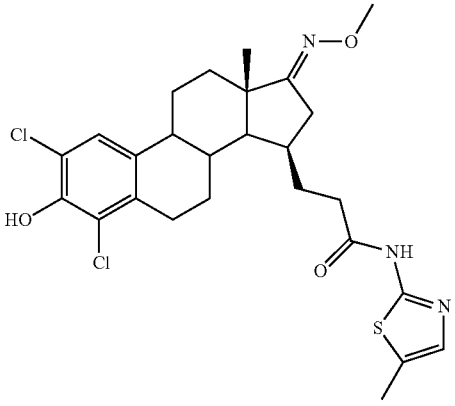 [SMILES: CO/N=C1\C[C@@H](CCC(=O)Nc2ncc(C)s2)C2C3CCc4c(cc(Cl)c(O)c4Cl)C3CC[C@]12C] | $^1$H-NMR (CDCl$_3$): 1.10 (s, 3H), 1.4-3.0 (m, 18H), 2.42 (s, 3H), 3.85 (s, 3H), 7.07 (s, 1H), 7.21 (s, 1H). |
| 91 | 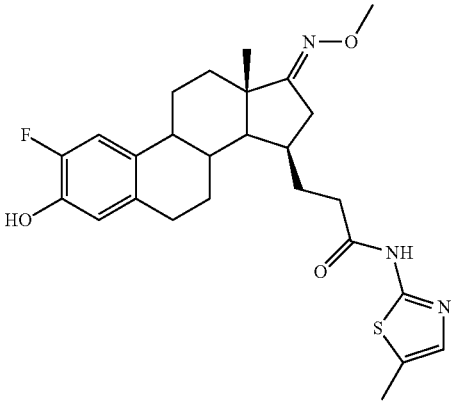 | $^1$H-NMR (CDCl$_3$ + MeOH-d$_4$): 1.10 (s, 3H), 1.25-3.0 (m, 21H), 3.84 (s, 3H), 6.66 (d, J = 10 Hz, 1H), 6.94 (d, J = 12 Hz, 1H), 7.03 (br s, 1H). |

TABLE 1-continued
| # | Compound | NMR |
|---|---|---|
| 92 | 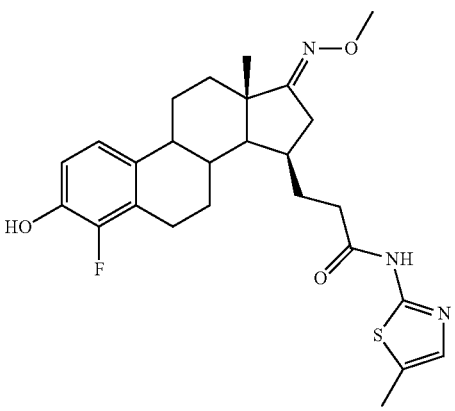 | $^1$H-NMR (CDCl$_3$): 1.09 (s, 3H), 1.30-2.95 (m, 21H), 3.84 (s, 3H), 6.79 (t, J = 4 Hz, 1H), 6.94 (d, J = 4 Hz, 1H), 7.07 (br s, 1H). |
| 93 | 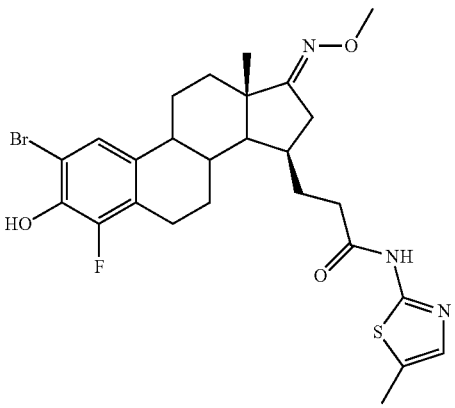 [SMILES: CO/N=C1\C[C@@H](CCC(=O)Nc2ncc(C)s2)C2C3CCc4c(cc(Br)c(O)c4F)C3CC[C@]12C] | $^1$H-NMR (CDCl$_3$): 1.10 (s, 3H), 1.53-2.90 (m, 21H), 3.84 (s, 3H), 7.06 (d, 1H), 7.17 (d, 1H). |
| 94 | 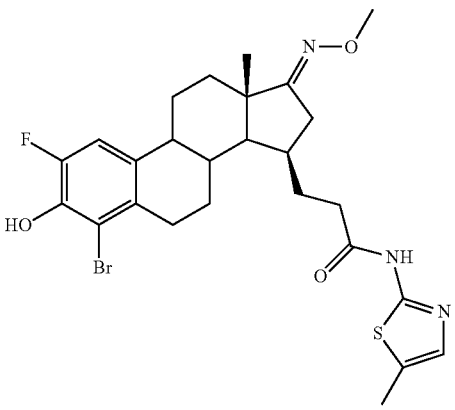 | $^1$H-NMR (CDCl$_3$): 1.09 (s, 3H), 1.25-2.91 (m, 21H), 3.85 (s, 3H), 7.01 (d, 1H), 7.07 (d, 1H). |

TABLE 1-continued
| # | Compound | NMR |
|---|---|---|
| 95 | 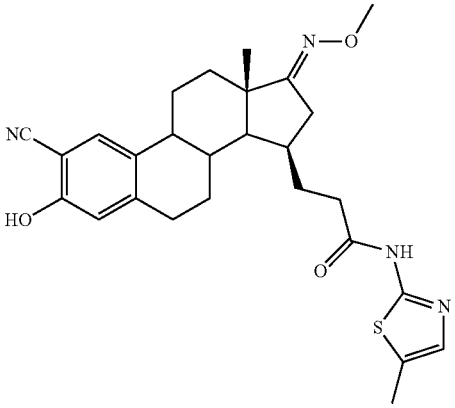 [SMILES: CO/N=C1\C[C@@H](CCC(=O)Nc2ncc(C)s2)C2C3CCc4cc(O)c(C#N)cc4C3CC[C@]12C] | ¹H-NMR (CDCl₃): 1.09 (s, 3H), 1.2-2.43 (m, 19H), 2.87 (m, 2H), 3.85 (s, 3H), 6.70 (s, 1H), 7.37 (s, 1H). |
| 96 | 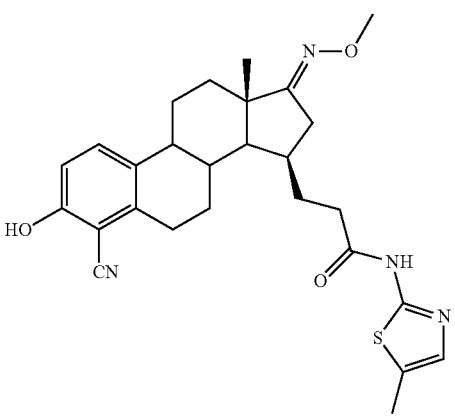 [SMILES: CO/N=C1\C[C@@H](CCC(=O)Nc2ncc(C)s2)C2C3CCc4c(ccc(O)c4C#N)C3CC[C@]12C] | ¹H-NMR (CDCl₃): 1.09 (s, 3H), 1.4-2.6 (m, 19H), 3.03 (m, 2H), 3.84 (s, 3H), 6.79 (d, 1H), 7.38 (d, 1H). |
| 97 | 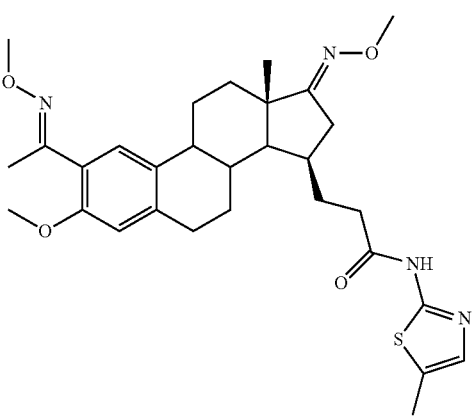 [SMILES: CO/N=C(\C)c1cc2c(cc1OC)CCC1C2CC[C@]2(C)/C(=N/OC)C[C@@H](CCC(=O)Nc3ncc(C)s3)C12] | ¹H-NMR (CDCl₃): 1.10 (s, 3H), H-18), 1.35-3.00 (m, 24H), 3.80 (s, 3H), 3.84 (s, 3H), 3.96 (s, 3H), 6.61 (s, 1H), 7.07 (s, 1H), 7.20 (s, 1H), 12.07 (s, 1H). |

TABLE 1-continued

| # | Compound | NMR |
|---|---|---|
| 98 | | ¹H-NMR (CDCl₃): 1.11 (s, 3H), 1.35-2.95 (m, 21H), 3.55-3.90 (m, 6H), 6.58 (s, 1H), 6.90 (s, 1H), 7.07 (s, 1H), 11.95 (br s, 1H). |
| 99 | | ¹H-NMR (CDCl₃): 1.11 (s, 3H), 1.30-2.95 (m, 21H), 3.65-3.85 (m, 6H), 3.84 (s, 3H), 7.02 (s, 1H), 7.05 (s, 1H), 11.36 (br s, 1H). |
| 100 | | ¹H-NMR (CDCl₃): 1.11 (s, 3H), 1.35-2.97 (m, 24H), 3.85 (s, 3H), 6.76-6.90 (m, 2H), 7.04 (s, 1H), 7.31 (s, 1H). |

TABLE 1-continued
| # | Compound | NMR |
|---|---|---|
| 101 | 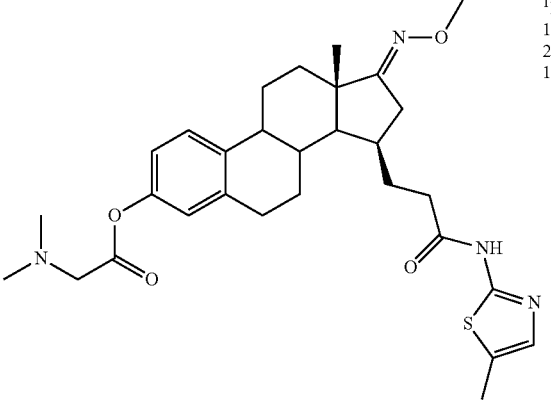 | ¹H-NMR (CDCl₃): 1.10 (s, 3H), 1.5-3.0 (m, 18H), 2.42 (s, 3H), 2.45 (s, 6H), 3.42 (s, 2H), 3.84 (s, 3H), 6.85 (m, 2H), 7.07 (s, 1H), 7.30 (s, 1H). |
| 102 | 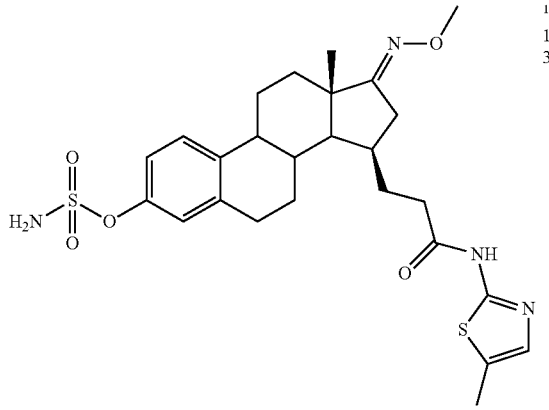 | ¹H-NMR (CDCl₃): 1.10 (s, 3H), 1.3-2.8 (m, 18H), 2.39 (s, 3H), 3.85 (s, 3H), 6.97 (m, 3H), 7.17 (m, 1H). |
| 103 | 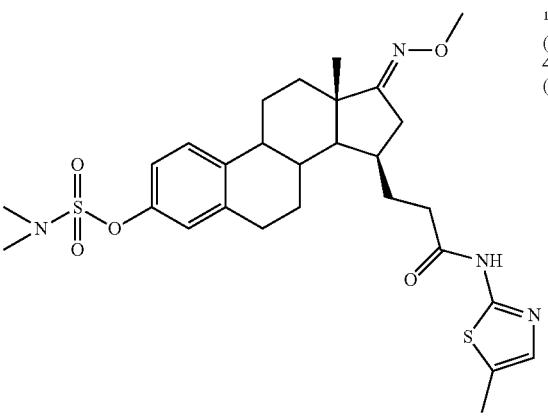 | ¹H-NMR (CDCl₃): 1.11 (s, 3H), 1.3-1.85 (m, 7H), 1.9-2.55 (m, 10H), 2.55-2.91 (m, 4H), 2.98 (s, 6H), 3.84 (s, 3H), 6.95-7.1 (m, 3H), 7.3 (s, 1H), 12.26 (s, 1H). |

TABLE 1-continued

| # | Compound | NMR |
|---|----------|-----|
| 104 | (structure) | ¹H-NMR (CDCl₃): 1.11 (s, 3H), 1.20-3.00 (m, 21H), 3.13 (s, 3H), 3.85 (s, 3H), 7.02-7.07 (m, 2H), 7.26-7.33 (m, 2H). |
| 105 | (structure) | ¹H-NMR (DMSO-d₆): 1.03 (s, 3H), 1.17 (t, 3H), 1.2-2.9 (m, 18H), 2.33 (s, 3H), 3.98 (q, 2H), 6.50 (m, 2H), 7.04 (d, 1H), 7.11 (s, 1H), 9.04 (s, 1H), 11.91 (s, 1H). |
| 106 | (structure) | ¹H-NMR (DMSO-d₆): 1.03 (s, 3H), 1.17 (t, 3H), 1.31 (s, 9H), 1.2-2.8 (m, 18H), 2.33 (s, 3H), 3.99 (q, 2H), 6.46 (s, 1H), 7.00 (s, 1H), 7.11 (s, 1H), 8.97(s, 1H), 11.91 (s, 1H). |

TABLE 1-continued

| # | Compound | NMR |
|---|----------|-----|
| 107 | | ¹H-NMR (CDCl₃): 1.10 (s, 3H), 1.40-3.00 (m, 21H), 4.55 (d, 2H), 5.10-5.35 (m, 2H), 5.90-6.10 (m, 1H), 6.58 (s, 1H), 6.63 (d, 1H), 7.08 (s, 1H), 7.13 (d, 1H). |
| 108 | | ¹H-NMR (CDCl₃): 1.12 (s, 3H), 1.35-3.00 (m, 21H), 4.56 (d, 2H), 5.10-5.35 (m, 2H), 5.90-6.10 (m, 1H), 6.86 (s, 1H), 7.07 (s, 1H), 7.97 (s, 1H). |
| 109 | | ¹H-NMR (DMSO-d₆): 1.03 (s, 3 H), 1.20-3.0 (m, 21H), 4.47 (br s, 2H), 6.47 (m, 2H), 7.04 (d, 1H), 7.11 (s, 1H), 9.04 (s, 1H), 11.93(s, 1H) |

| # | Compound | NMR |
|---|---|---|
| 110 | 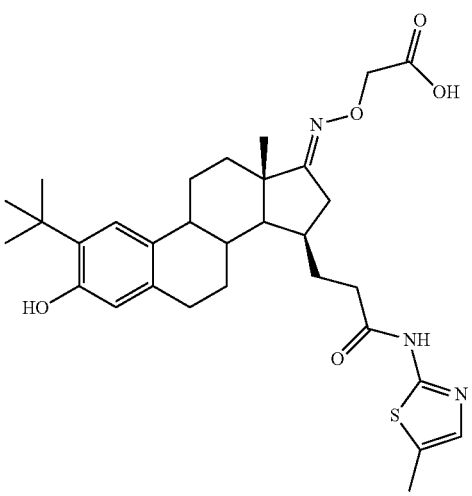 [SMILES: Cc1cnc(NC(=O)CC[C@@H]2C/C(=N\OCC(=O)O)[C@@]3(C)CCC4c5cc(C(C)(C)C)c(O)cc5CCC4C23)s1] | $^1$H-NMR (CDCl$_3$ + MeOH-d$_4$): 1.12 (s, 3H), 1.30-3.15 (m, 30H), 4.66 (s, 2H), 6.44 (s, 1H) 7.01 (s, 1H), 7.15 (s, 1H). |
| 111 | 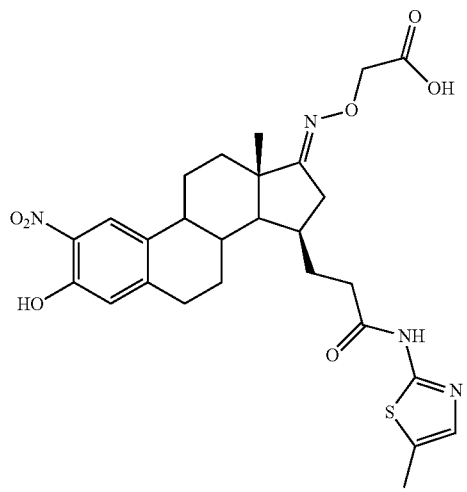 [SMILES: Cc1cnc(NC(=O)CC[C@@H]2C/C(=N\OCC(=O)O)[C@@]3(C)CCC4c5cc([N+](=O)[O-])c(O)cc5CCC4C23)s1] | $^1$H-NMR (CDCl$_3$ + MeOH-d$_4$): 1.09 (s, 3H), 1.35-3.10 (m, 21H), 4.61 (s, 2H), 6.87 (s, 1H), 7.01 (s,1H), 7.94 (s, 1H). |
| 112 | 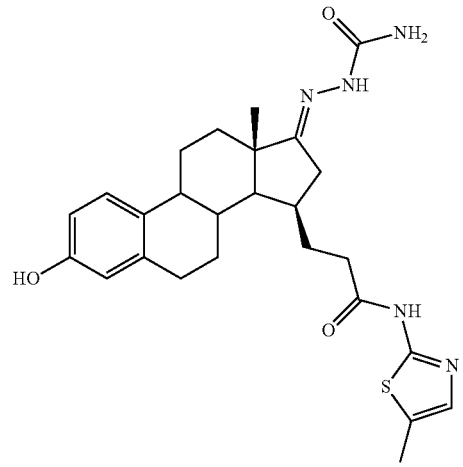 [SMILES: Cc1cnc(NC(=O)CC[C@@H]2C/C(=N\NC(N)=O)[C@@]3(C)CCC4c5ccc(O)cc5CCC4C23)s1] | $^1$H-NMR (DMSO-d$_6$): 0.99 (s, 3H), 1.20-2.90 (m, 21H), 2.33 (s, 3H), 6.15 (br s, 2H), 6.46 (s, 1H), 6.50 (d, 1H), 7.05 (d,1H), 7.11 (s, 1H), 8.73 (s, 1H), 9.02 (s, 1H), 11.94 (br s, 1H). |

TABLE 1-continued
| # | Compound | NMR |
|---|---|---|
| 113 | 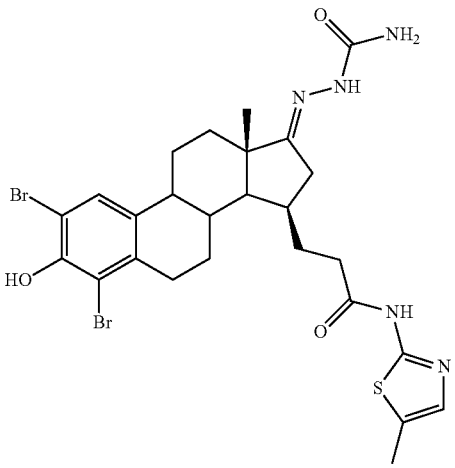 [SMILES: Cc1cnc(NC(=O)CC[C@@H]2C/C(=N\NC(N)=O)[C@@]3(C)CCC4c5cc(Br)c(O)c(Br)c5CCC4C23)s1] | $^1$H-NMR (DMSO-d$_6$): 0.97 (s, 3H), 1.20-2.95 (m, 21H), 2.33 (s, 3H), 6.16 (s, 2H), 7.11 (s, 1H), 7.41 (s, 1H), 8.74 (s, 1H), 9.49 (s, 1H), 11.94 (br s, 1H). |
| 114 | 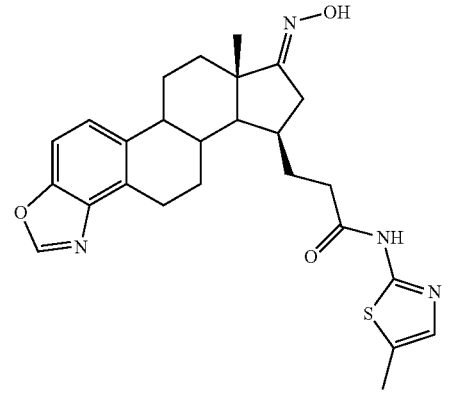 [SMILES: Cc1cnc(NC(=O)CC[C@@H]2C/C(=N\O)[C@@]3(C)CCC4c5ccc6ocnc6c5CCC4C23)s1] | $^1$H-NMR (CDCl$_3$ + MeOH-d$_4$): 1.15 (s, 3H), 1.45-3.35 (m, 21H), 7.03 (s,1H), 7.37(s, 2H), 8.09 (s, 1H). |
| 115 | 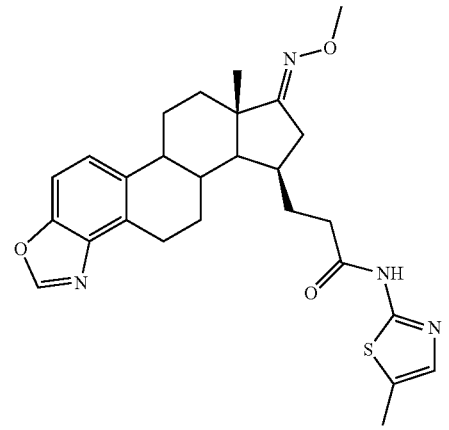 [SMILES: CO/N=C1\C[C@@H](CCC(=O)Nc2ncc(C)s2)C2C3CCc4c(ccc5ocnc45)C3CC[C@]12C] | $^1$H-NMR (CDCl$_3$): 1.13 (s, 3H), 1.40-3.45 (m, 21H), 3.85 (s, 3H), 7.08 (s,1H), 7.36 (s, 2H), 8.05 (s, 1H), 12.26 (br s, 1H). |

TABLE 1-continued
| # | Compound | NMR |
|---|---|---|
| 116 | 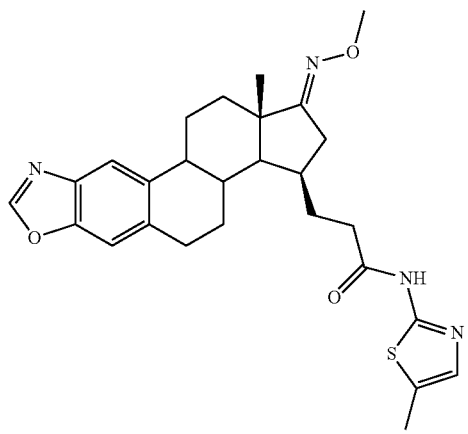 [SMILES: CO/N=C1\C[C@@H](CCC(=O)Nc2ncc(C)s2)C2C3CCc4cc5ocnc5cc4C3CC[C@]12C] | ¹H-NMR (CDCl₃): 1.12 (s, 3H), 1.40-3.10 (m, 21H), 3.85 (s, 3H), 7.06 (s,1H), 7.30 (s, 1H), 7.70 (s, 1H), 8.01 (s, 1H), 12.36 (br s, 1H). |
| 117 | 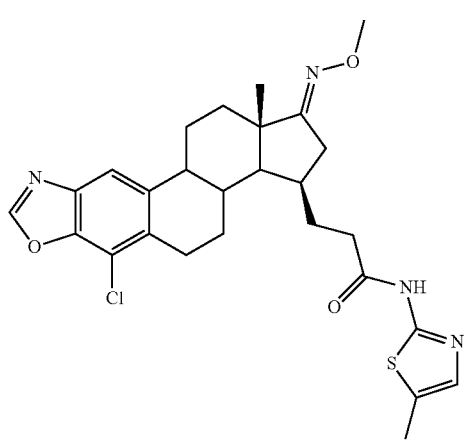 [SMILES: CO/N=C1\C[C@@H](CCC(=O)Nc2ncc(C)s2)C2C3CCc4c(cc5ncoc5c4Cl)C3CC[C@]12C] | ¹H-NMR (CDCl₃): 1.11 (s, 3H), 1.40-3.20 (m, 21H), 3.85 (s, 3H), 7.08 (s, 1H), 7.66 (s,1H), 8.05 (s, 1H), 12.00 (br s, 1H). |
| 118 | 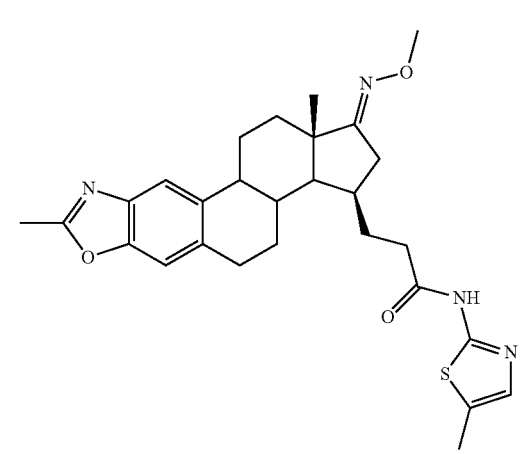 [SMILES: CO/N=C1\C[C@@H](CCC(=O)Nc2ncc(C)s2)C2C3CCc4cc5oc(C)nc5cc4C3CC[C@]12C] | ¹H-NMR (CDCl₃): 1.11 (s, 3H), 1.40-3.10 (m, 21H), 2.60 (s, 3H), 3.85 (s, 3H), 7.07 (s,1H), 7.17 (s, 1H), 7.55 (s, 1H), 12.36 (br s, 1H). |

TABLE 1-continued
| # | Compound | NMR |
|---|---|---|
| 119 | 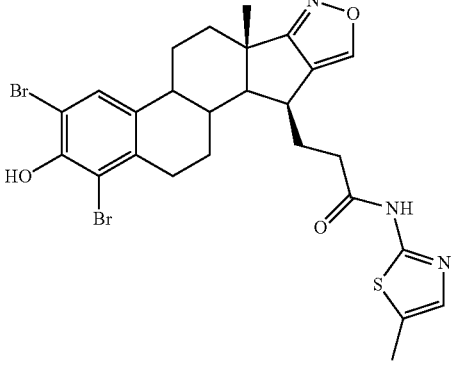 | $^1$H-NMR (CDCl$_3$ + MeOH-d$_4$): 1.27 (s, 3H),1.40-3.05 (m, 19 H), 7.03 (s, 1H), 7.38 (s, 1H), 8.18 (s, 1H). |
| 120 | 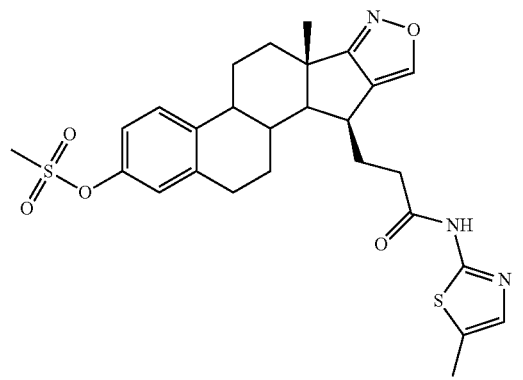 [SMILES: Cc1cnc(NC(=O)CC[C@@H]2c3conc3[C@@]3(C)CCC4c5ccc(OS(C)(=O)=O)cc5CCC4C23)s1] | $^1$H-NMR (CDCl$_3$): 1.26 (s, 3H), 1.40-3.10 (m, 19 H), 3.15 (s, 3H), 7.01 (s, 1H), 7.04 s, 1H) 7.06 (d, 1H), 7.30 (d, 1H), 8.07 (s, 1H). |
| 121 | 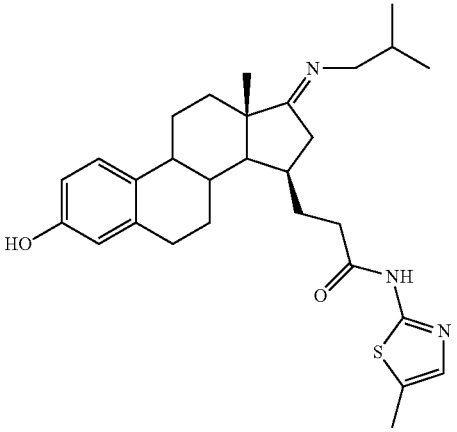 [SMILES: Cc1cnc(NC(=O)CC[C@@H]2C/C(=N\CC(C)C)[C@@]3(C)CCC4c5ccc(O)cc5CCC4C23)s1] | $^1$H NMR (200 MHz, CDCl$_3$) δ ppm 0.77-1.07 (m, 6 H), 1.05 (s, 3H), 1.43 (s, 3H), 1.5-2.9 (m, 21H), 3.07 (d, 2H), 6.54-6.7 (m, 2H), 7.07 (br, 2H) |
| 122 | 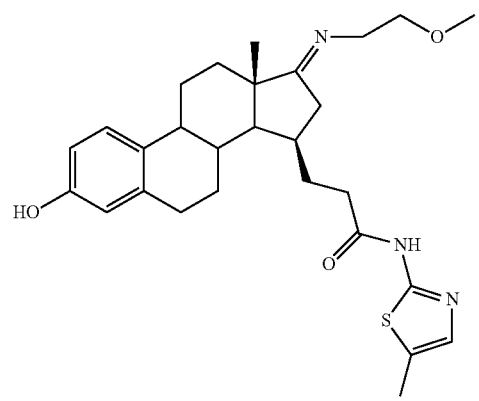 [SMILES: COCC/N=C1\C[C@@H](CCC(=O)Nc2ncc(C)s2)C2C3CCc4cc(O)ccc4C3CC[C@]12C] | $^1$H NMR (200 MHz, CDCl$_3$) δ ppm 0.99 (s, 3H), 1.43-1.69 (m, 6 H), 2.00-2.88 (m, 16H), 3.35 (d, 3H), 3.40 (m, 2H), 3.64 (m, 2H), 6.54-6.61 (m, 2H), 6.98 (m, 1H), 7.07 (br, 1H). |

TABLE 1-continued

| # | Compound | NMR |
|---|---|---|
| 123 | 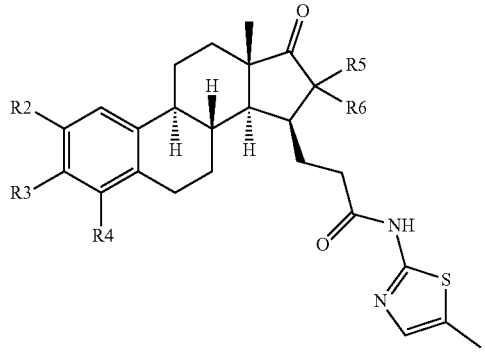 | $^1$H NMR (200 MHz, CDCl$_3$) δ ppm 1.04 (s, 3H), 1.39-1.85 (m, 16 H), 1.89-2.75 (m, 15H), 3.35 (s, 3H), 3.45 (m, 2H), 3.65 (m, 2H), 6.45 (m, 1H), 7.07 (br s, 1H), 7.16 (br s, 1H). |
| 124 | 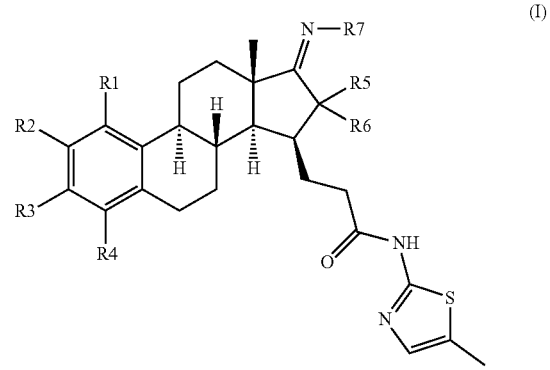 | $^1$H-NMR (DMSO-d$_6$): 1.02 (s, 3H), 1.33 (s, 9H), 1.20-2.80 (m, 21H), 3.73 (s, 3H), 7.11 (s, 1H), 7.14 (s, 1H), 7.97 (s, 1H), 11.90 (br s, 1H). |

Compounds of this invention are also useful in the form of acid or base addition salts, hydrates, or solvates thereof.

The invention further relates to a method for the preparation of a compound of the present invention, comprising the steps of: A) reacting a compound of formula (II)

(II)

wherein R2 to R6 are as defined in any one of claims 1 to 10, with a compound of formula (IIIa)

NH$_2$—OR7' (IIIa)

or hydrogen halide thereof, wherein and R7' is H, C$_{1-6}$-alkyl, C$_{3-6}$-alkenyl, or carboxy-C$_{3-6}$-alkylenyl, in the presence of a base, preferably pyridine, to obtain a compound of formula (I)

(I)

wherein R7 is OR7' as defined above; or

B) reacting a compound of formula (II)

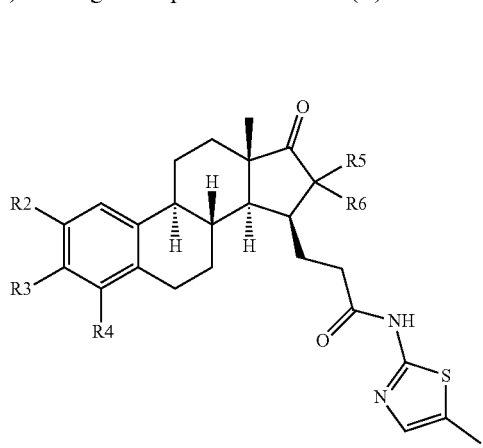

wherein R2 to R6 are as define in any one of claim 1 to 10,
with a compound of formula (IIIe)
NH2-NHR7' (IIIe)
wherein R7' is ureido,
to obtain a compound of formula (I) which compound has formula (Ie)

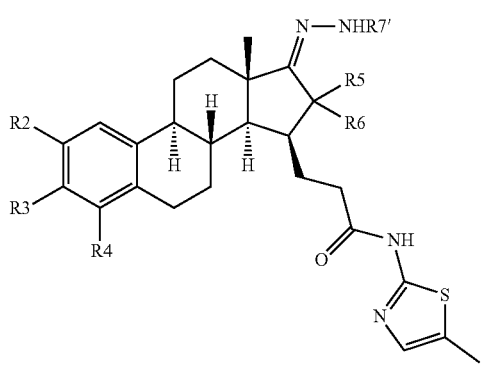

wherein R2 to R6 are as defined above and R7' is ureido; or

C) reacting a compound of formula (II)

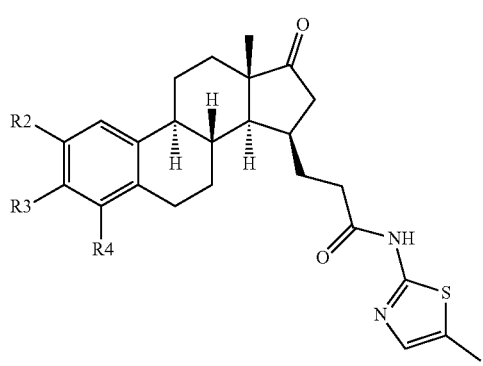

with ethyl formate in the presence of sodium hydride to obtain a compound of formula (III)

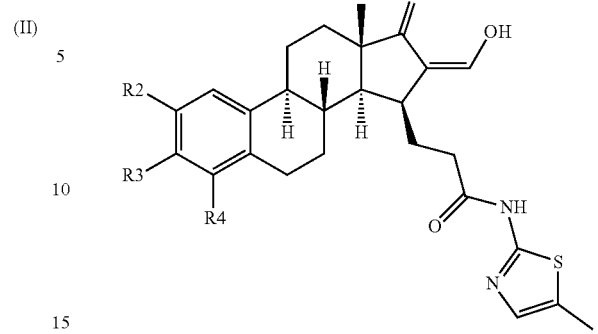

and then reacting the obtained compound of formula (III) with hydrazine hydrate or Eaton's reagent to obtain a compound of formula (Ib)

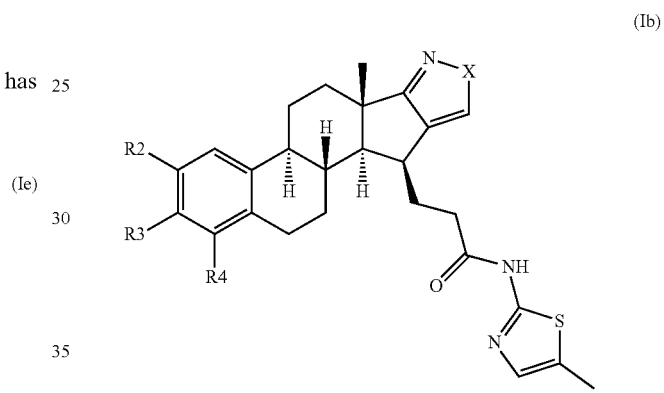

wherein X is NH or O, respectively, and R2, R3 and R4 are as defined above;

and optionally converting the obtained compound of formula (I) to a corresponding pharmaceutically acceptable salt.

Preferably the compound of formula (IIIa) is selected from the group consisting of hydroxyl amine, $C_{1-6}$-alkoxyl amine, O—$C_{2-6}$-alkenyl hydroxyl amine, O-carboxy-$C_{1-3}$-alkyl hydroxyl amine and semicarbazide, or hydrogen halide, preferably hydrochloride, thereof, to obtain a compound of formula (I) wherein R7 is respectively $C_{1-6}$-alkoxyl, O—$C_{2-6}$-alkenyl hydroxyl, O-carboxy-$C_{1-3}$alkylenyl hydroxyl or semicarbazidyl.

General Preparation Methods

Compounds of the present invention may be prepared by methods known in the art.

The following examples illustrate the preparation of compounds of formula (I).

Preparation of Synthesis Starting Materials and Precursors

Compound VII may be synthesized as disclosed in Messinger et al. Mol Cell Endocrinol. 2009 (301) 216-224. The detailed synthesis of compound VII starting from estrone has been described in the Solvay Pharmaceuticals' PCT applications WO2005/047303 and WO2006/125800.

Benzyl-C15-C16-dehydroestrone II was prepared in five steps from estrone according to previously described methods. The compound II was treated with an allylic Grignard reagent in the presence of cuprous iodide and lithium chloride in temperature −78° C. Hydroboration by borane tetrahydrofuran complex at room temperature to compound III and following hydrogen peroxide oxidation in alkaline conditions produced diol IV in over 90% yields. Jones oxidation in acetone-water afforded acid V, which was debenzylated by hydrogenation to compound VI by using Pd/C as a catalyst. The final step was the amide formation affording the β-thiazole VII.

The synthesis of the key precursor i.e. the phenolic thiazole VII from estrone is shown below.

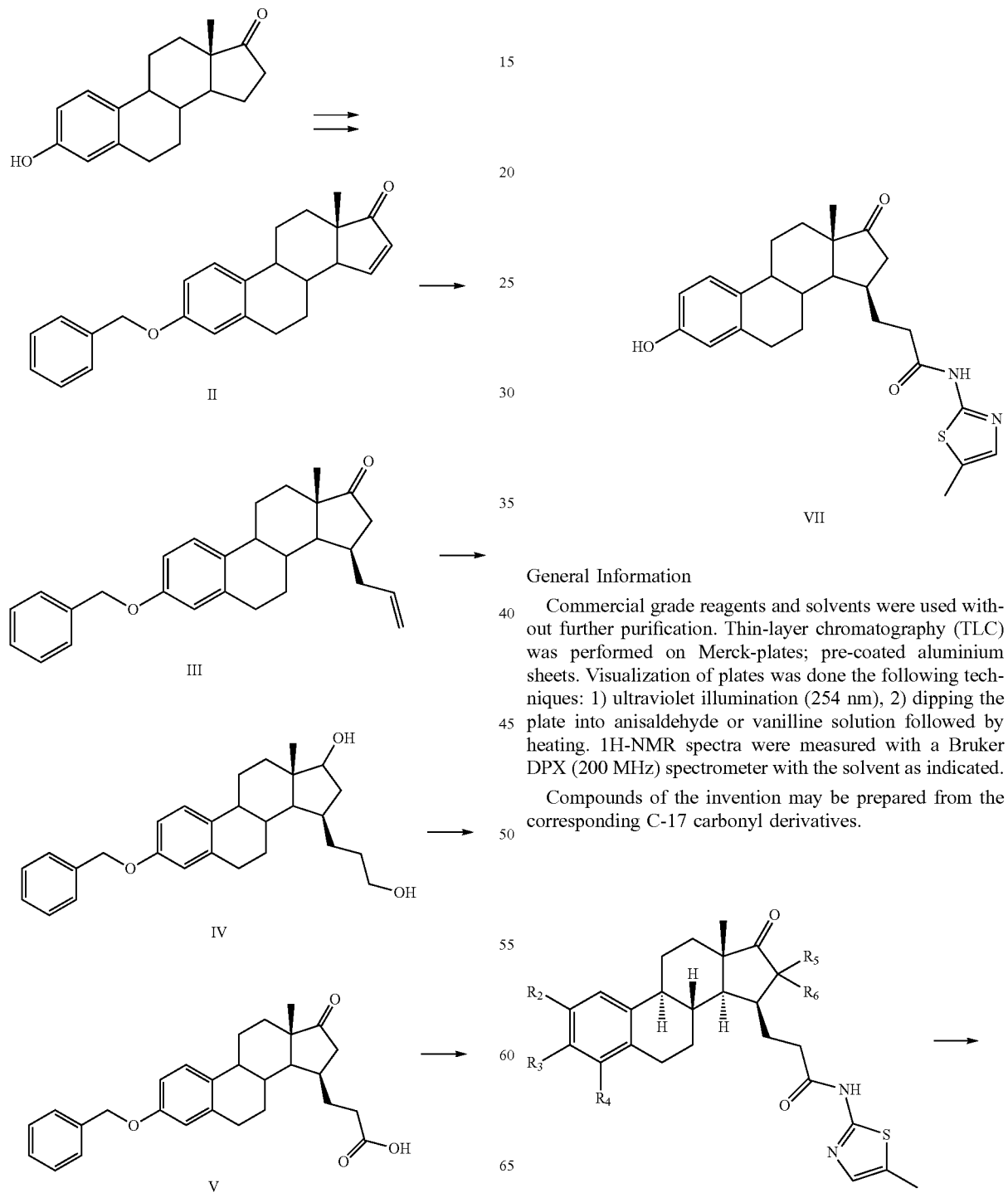

General Information

Commercial grade reagents and solvents were used without further purification. Thin-layer chromatography (TLC) was performed on Merck-plates; pre-coated aluminium sheets. Visualization of plates was done the following techniques: 1) ultraviolet illumination (254 nm), 2) dipping the plate into anisaldehyde or vanilline solution followed by heating. 1H-NMR spectra were measured with a Bruker DPX (200 MHz) spectrometer with the solvent as indicated.

Compounds of the invention may be prepared from the corresponding C-17 carbonyl derivatives.

-continued

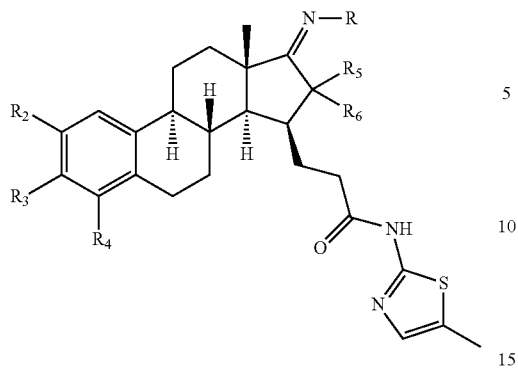

Preparation of C-17 Carbonyl Compounds

Compound 1

3-((13S,15R)-3-methoxy-13-methyl-17-oxo-7,8,9,
11,12,13,14,15,16,17-decahydro-6H-cyclopenta[a]
phenanthren-15-yl)propanoic acid

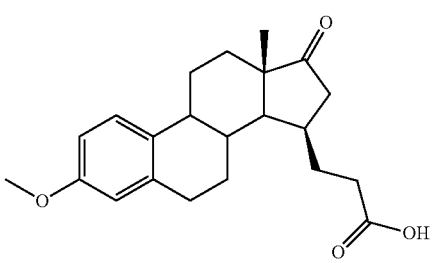 [SMILES: COc1ccc2c(c1)CCC1C2CC[C@]2(C)C(=O)C[C@@H](CCC(=O)O)C12]

The compound VI (2.0 g, 100 mol-%) was dissolved in acetone (40 ml). Potassium carbonate (200 mol-%) and methyl iodide (MeI) (500 mol-%) were added and stirred at room temperature (rt) overnight. Additional amounts of MeI (200 mol-%) and $K_2CO_3$ (100 mol-%) were added and refluxed for 10 hours. The solvent was evaporated. The precipitate was dissolved in methanol (50 ml) and 2M NaOH-solution was added until pH was >12. The reaction mixture was stirred at rt for 4 hours. The reaction mixture was acidified by HCl. The product was extracted with dichloromethane (DCM) (3×30 ml), washed several times with water and finally with brine. The amount of the product 1 was 1.95 g; the yield was 94%.

$^1$H-NMR (CDCl$_3$): 1.05 (s, 3H), 1.45-2.48 (m, 19H), 2.93 (m, 2H), 3.79 (s, 3H), 6.70 (m, 2H), 7.20 (d, 1H).

Compound 2

3-((13S,15R)-3-methoxy-13-methyl-17-oxo-7,8,9,
11,12,13,14,15,16,17-decahydro-6H-cyclopenta[a]
phenanthren-15-yl)-N-(5-methylthiazol-2-yl)pro-
panamide

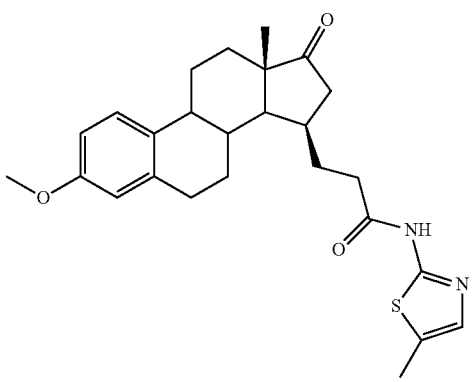 [SMILES: COc1ccc2c(c1)CCC1C2CC[C@]2(C)C(=O)C[C@@H](CCC(=O)Nc3ncc(C)s3)C12]

The compound 1 (2.0 g, 100 mol-%) was dissolved in dry DCM (80 ml). 2-Amino-5-methylthiazol (200 mol-%), N-methylmorpholine (NMM) (300 mol-%) ja 1-hydroxy-1H-benzotriazole (HOBT) (170 mol-%) were added. The reaction mixture was stirred for five minutes, cooled to 0-5° C. and 1-ethyl-3-(3'dimethylaminopropyl)carbodiimide hydrochloride (EDCl) (220 mol-%) was added. The reaction mixture was stirred at rt overnight and then diluted with DCM, washed with 1N HCl-solution and 5% KOH-solution. The organic phase was finally washed with water and brine. The crude product was purified by chromatography affording 1.85 of the product; the yield was 73%.

$^1$H-NMR (CDCl$_3$): 1.06 (s, 3H), 1.37-2.60 (m, 22H), 2.90 (m, 2H), 3.79 (s, 3H), 6.70 (m, 2H), 7.05 (s, 1H), 7.19 (d, 1H), 12.11 (s, 1H).

Compound 3

3-((13S,15R)-2-(tert-butyl)-3-hydroxy-13-methyl-
17-oxo-7,8,9,11,12,13,14,15,16,17-decahydro-6H-
cyclopenta[a]phenanthren-15-yl)-N-(5-methylthi-
azol-2-yl)propanamide

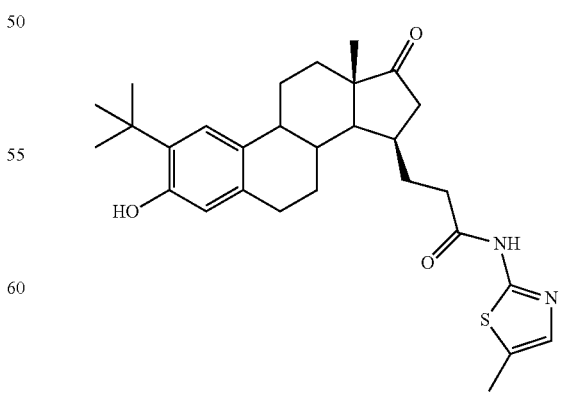

To a stirred suspension of the compound VII (2.0 g, 100 mol-%) in dry dichloromethane, tert-butanol (1.5 ml) and boron trifluoride diethyl etherate (3.2 ml) were added with a syringe at rt and the reaction was followed by TLC. The mixture was stirred overnight at rt and additional amount of boron trifluoride diethyl etherate (1 ml) and tert-butanol (500 µl) were added. The resulting orange solution was stirred for 3 hours before water (40 ml) and DCM (40 ml) were added carefully. The layers were separated and the aqueous layer was extracted with DCM (3×30 ml). The combined organic layers were washed with water (3×30 ml), saturated aqueous NaHCO$_3$ (30 ml) and brine (3×30 ml). The solvents were evaporated and the precipitate was washed with heptane affording 1.8 g of the product 3 (yield 80%).

$^1$H-NMR (DMSO-d$_6$): 0.97 (s, 3H), 1.2-1.45 (m, 12H), 1.5-2.4 (m, 16H), 2.6-2.95 (m, 2H), 6.47 (s, 1H), 7.01 (s, 1H), 7.11 (s, 1H), 8.97 (s, 1H), 11.92 (s, 1H, —NH). MS m/z (TOF ES+): 517 (M+Na)

Compound 4

3-((13S,15R)-2-acetyl-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide

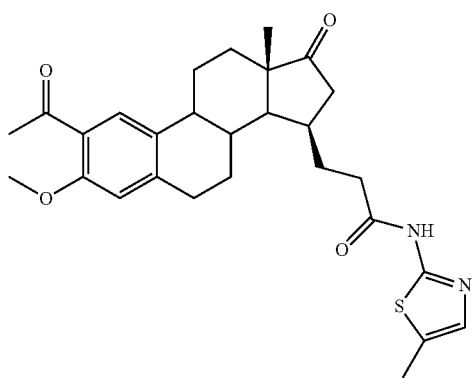 [SMILES: COc1cc2c(cc1C(C)=O)C1CC[C@]3(C)C(=O)C[C@@H](CCC(=O)Nc4ncc(C)s4)C3C1CC2]

Acetyl chloride (34 mg, 195 mol-%) was added dropwise to a cooled (0° C.) suspension of AlCl$_3$ (59 mg, 200 mol-%) in DCM (1 ml). To this was added dropwise a solution of the compound 2 (100 mg, 100 mol-%) in DCM (1 ml). The reaction mixture was stirred 2 h at 0° C. and stirring was continued overnight at rt. The additional suspension of AlCl$_3$ (63 mg, 210 mol-%) and acetyl chloride (32 mg, 190 mol-%) in DCM (1 ml) was added to the reaction. Ice-cold water (5 ml) and DCM (10 ml) were added to the reaction mixture and it was stirred 10 min. The layers were separated and aqueous layer was extracted with DCM (2×10 ml). The combined organic layers were washed with water (15 ml) and brine (15 ml), dried with Na$_2$SO$_4$ and the solvents were evaporated. The crude product was purified by column chromatography. The yield of the product 4 was 75 mg (69%).

$^1$H-NMR (CDCl$_3$): 1.05 (s, 3H), 1.36-2.68 (m, 22H), 2.90-3.03 (m, 2H), 3.89 (s, 3H), 6.69 (s, 1H), 7.05 (s, 1H), 7.69 (s, 1H), 11.76 (br, 1H). MS m/z (TOF ES+): 495 (M+1).

Nitration of the Compound VII

The reaction vessel was charged with the compound VII (1.32 g, 3 mmol) and ethanol (45 ml) under nitrogen atmosphere. Tetrahydrofuran (THF) (30 ml) and ferric nitrate (600 mg, 1.5 mmol) were added. After stirring the reaction mixture for 4 h at 60° C., the solvents were evaporated. HPLC of the crude reaction mixture showed 45% of 2-nitro-isomer 5 and 35% of 4-nitroisomer 6. Purification by flash chromatography gave 358 mg of 5 and 284 mg of 6. In addition, the product mixture contained ca. 5% of 2,4-dinitro derivative 7.

Compound 5

3-((13S,15R)-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

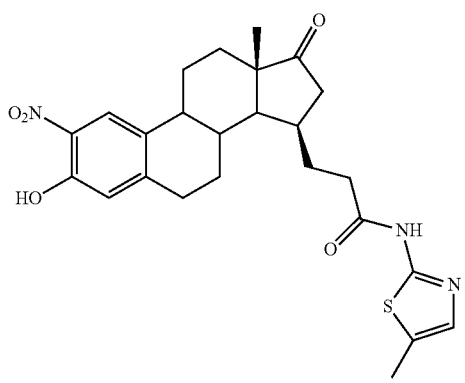 [SMILES: Cc1cnc(NC(=O)CC[C@@H]2CC(=O)[C@@]3(C)CCC4c5cc([N+](=O)[O-])c(O)cc5CCC4C23)s1]

$^1$H-NMR (CDCl$_3$): 1.07 (s, 3H), 1.30-2.75 (m, 19H), 2.9-3.05 (m, 2H), 6.89 (s, 1H), 7.05 (s, 1H), 7.98 (s, 1H). MS m/z (TOF ES$^+$): 506 (M+Na)

Compound 6

3-((13S,15R)-3-hydroxy-13-methyl-4-nitro-17-oxo-7,8,9,11,12,13,14,15,16,17-decahydro-6H-cyclopenta[a]phenanthren-15-yl)-N-(5-methylthiazol-2-yl)propanamide

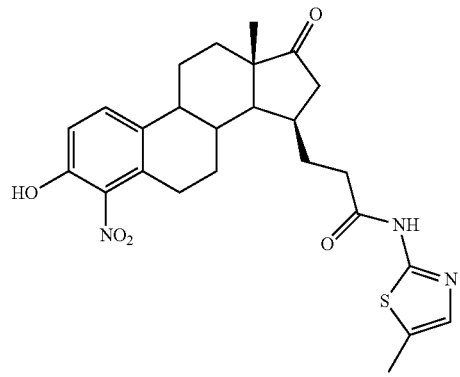 [SMILES: Cc1cnc(NC(=O)CC[C@@H]2CC(=O)[C@@]3(C)CCC4c5ccc(O)c([N+](=O)[O-])c5CCC4C23)s1]

$^1$H-NMR (CDCl$_3$): 1.08 (s, 3H), 1.3-3.4 (m, 21H), 6.96 (d, 1H), 7.05 (s, 1H), 7.45 (d, 1H). MS m/z (TOF ES$^+$): 506 (M+Na)

Compound 7

3-((13S,15R)-3-hydroxy-13-methyl-2,4-dinitro-17-oxo-7,8,9,11,12,13,14,15,16,17-decahydro-6H-cyclopenta[a]phenanthren-15-yl)-N-(5-methylthiazol-2-yl)propanamide

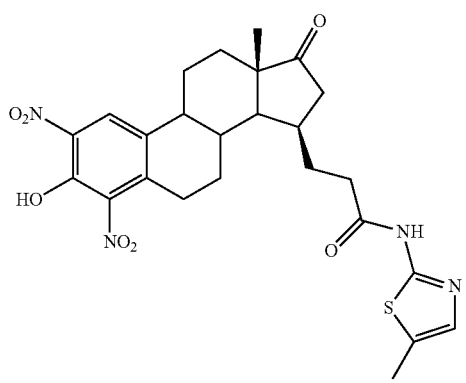 [SMILES: Cc1cnc(NC(=O)CC[C@@H]2CC(=O)[C@@]3(C)CCC4c5cc([N+](=O)[O-])c(O)c([N+](=O)[O-])c5CCC4C23)s1]

$^1$H-NMR (CDCl$_3$): 1.08 (s, 3H), 1.35-3.10 (m, 21H), 7.03 (s, 1H), 8.14 (s, 1H). MS m/z (TOF ES$^+$): 529 (M+H)

Reduction of 2- and 4-Nitrocompounds to Corresponding Aminoderivatives

Compound 8

3-((13S,15R)-2-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

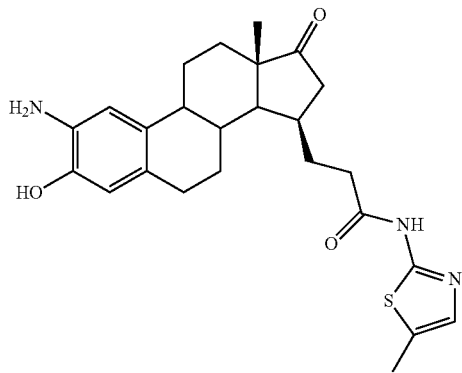

Hydrogenation of the compound 5 was carried out at atmospheric pressure at rt in ethanol/THF 1:1 using 10% Pd/C as catalyst. Catalyst was filtered off, solvents were evaporated and product purified by flash chromatography.

$^1$H-NMR (CDCl$_3$+MeOH-d$_4$): 1.06 (s, 3H), 1.30-2.65 (m, 19H), 2.80-2.95 (m, 2H), 6.50 (s, 1H), 6.69 (s, 1H), 7.03 (s, 1H). MS m/z (TOF ES$^+$): 454 (M+H)

Compound 9

3-((13S,15R)-4-amino-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

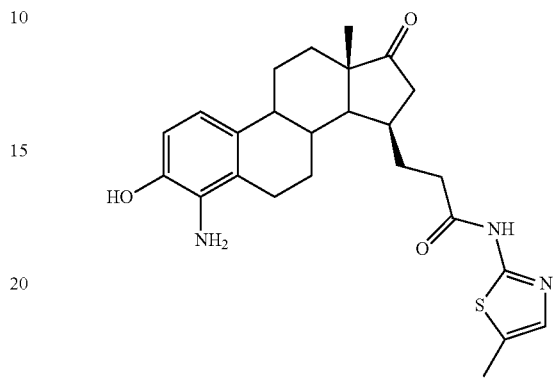

Prepared according to method used for the compound 8 using the compound 6 as a starting material.

$^1$H-NMR (CDCl$_3$+MeOH-d$_4$): 1.03 (s, 3H), 1.35-2.65 (m, 19H), 2.75-3.00 (m, 2H), 6.63 (s, 2H), 7.03 (s, 1H). MS m/z (TOF ES$^+$): 476 (M+Na).

Ring Amino and Aminomethyl Derivatives

General Method for Mannich Reaction (Aminomethylation) of Phenols:

Phenol (0.1-0.2 mmol scale) in ethanol-THF (v/v 3:2) was heated with excess of amine and formalin until TLC showed formation of a new reaction product. New compounds were purified by preparative TLC.

Compound 10

3-((13S,15R)-3-hydroxy-13-methyl-2-(morpholinomethyl)-17-oxo-7,8,9,11,12,13,14,15,16,17-decahydro-6H-cyclopenta[a]phenanthren-15-yl)-N-(5-methylthiazol-2-yl)propanamide

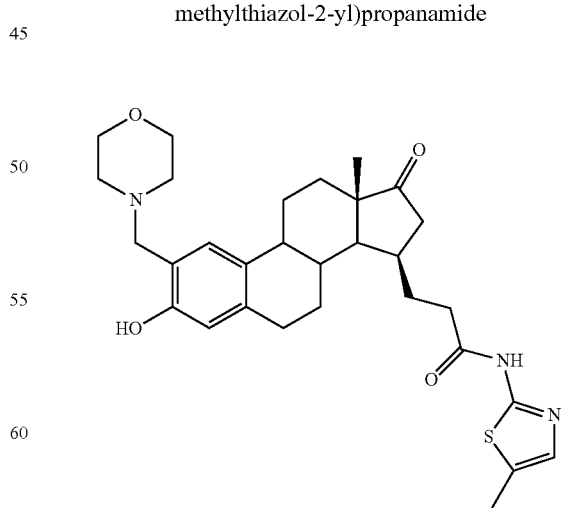

Prepared from the compound VII by the aminomethylation method described above using morpholine as an amine.

¹H-NMR (CDCl₃): 1.05 (s, 3H), 1.30-3.00 (m, 21H), 3.60-3.85 (m, 6H), 6.59 (s, 1H), 6.88 (s, 1H), 7.04 (s, 1H), 11.87 (br s, 1H). MS m/z (TOF ES⁺): 538 (M+H).

Compound 11

3-((13S,15R)-3-hydroxy-13-methyl-2-(morpholinomethyl)-4-nitro-17-oxo-7,8,9,11,12,13,14,15,16,17-decahydro-6H-cyclopenta[a]phenanthren-15-yl)-N-(5-methylthiazol-2-yl)propanamide

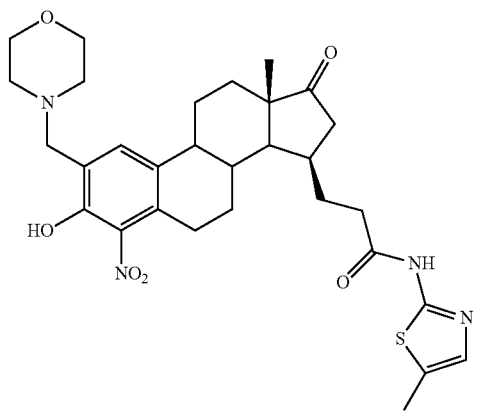 [SMILES: Cc1cnc(NC(=O)CC[C@@H]2CC(=O)[C@@]3(C)CCC4c5cc(CN6CCOCC6)c(O)c([N+](=O)[O-])c5CCC4C23)s1]

Prepared from the compound 6 by the aminomethylation method described above using morpholine as an amine.
¹H-NMR (CDCl₃): 1.06 (s, 3H), 1.30-3.00 (m, 21H), 3.65-3.85 (m, 6H), 7.02 (s, 1H), 7.04 (s, 1H), 11.58 (br s, 1H). MS m/z (TOF ES⁺): 583 (M+H).

Heterocyclic 2,3- and 3,4-Modifications

Compound 12

3-((7aS,10R)-7a-methyl-8-oxo-6,7,7a,8,9,10,10a,10b,11,12-decahydro-5bH-cyclopenta[7,8]phenanthro[1,2-d]oxazol-10-yl)-N-(5-methylthiazol-2-yl)propanamide

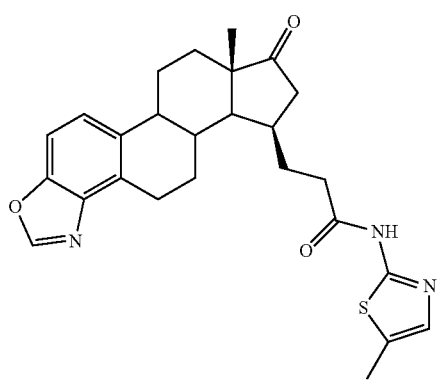 [SMILES: Cc1cnc(NC(=O)CC[C@@H]2CC(=O)[C@@]3(C)CCC4c5ccc6ocnc6c5CCC4C23)s1]

110 mg of the compound 9 was added under nitrogen atmosphere into a mixture of 1.5 ml methylortoformate and 1.5 ml of THF. Catalytic amount of p-toluenesulfonic acid was added and the mixture was stirred at rt until TLC showed starting material having disappeared. The mixture was evaporated and purified with flash chromatography giving 76 mg (68%) of the benzoxazole 12.
¹H-NMR (CDCl₃): 1.09 (s, 3H), 1.40-2.80 (m, 19H), 3.05-3.50 (m, 2H), 7.06 (s, 1H), 7.37 (s, 2H), 8.06 (s, 1H), 12.43 (s, 1H). MS m/z (TOF ES⁺): 486 (M+Na)

Compound 13

3-((3R,12aS)-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

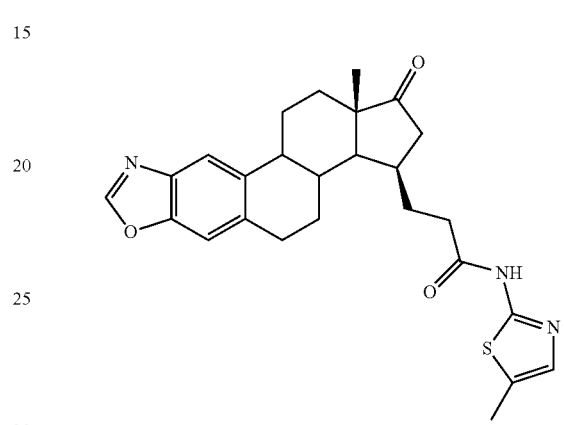

Prepared by the same method as the compound 12 using the compound 8 as starting material.
¹H-NMR (CDCl₃): 1.07 (s, 3H), 1.30-2.75 (m, 18H), 2.95-3.15 (m, 3H), 7.05 (s, 1H), 7.32 (s, 1H), 7.70 (s, 1H), 8.01 (s, 1H), 12.31 (s, 1H). MS m/z (TOF ES⁺): 486 (M+Na)

Compound 14

3-((3R,12aS)-8,12a-dimethyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

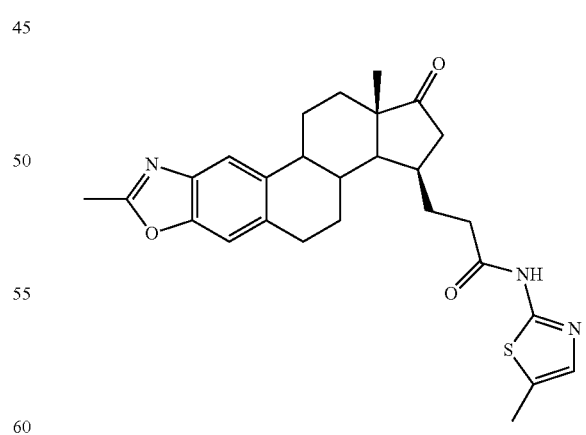

Prepared by the same method as the compound 12 using the compound 8 as starting material and ortoacetate instead of ortoformate as reagent.
¹H-NMR (CDCl₃): 1.07 (s, 3H), 1.35-2.75 (m, 22H), 2.90-3.10 (m, 2H), 7.05 (s, 1H), 7.19 (s, 1H), 7.55 (s, 1H), 12.22 (s, 1H). MS m/z (TOF ES⁺): 478 (M+H)

Halogenation of the Aromatic Ring

Compound 15

3-((13S,15R)-2-iodo-3-methoxy-13-methyl-17-oxo-7,8,9,11,12,13,14,15,16,17-decahydro-6H-cyclopenta[a]phenanthren-15-yl)-N-(5-methylthiazol-2-yl)propanamide

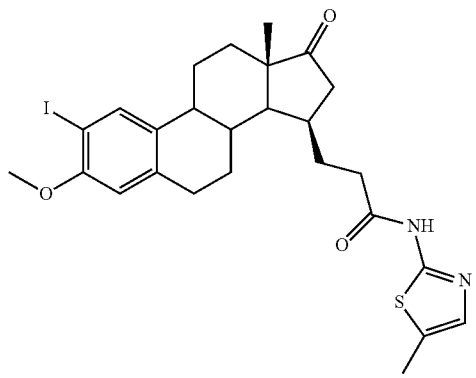 [SMILES: COc1cc2c(cc1I)C1CC[C@]3(C)C(=O)C[C@@H](CCC(=O)Nc4ncc(C)s4)C3C1CC2]

The compound 2 (100 mg, 100 mo-%) was dissolved in dry DCM (4 ml). Iodine, CF$_3$COOAg (73 mg, 150 mol-%) and NaHCO$_3$ (124 mg, 670 mol-%) were added and the reaction mixture was stirred for three hours at −30° C. The reaction mixture was filtered and the solid material was washed with DCM. The filtrate was evaporated followed by co-evaporation with toluene and heptane. The solid product was finally washed with heptane. The yield was 100 mg (78%).

$^1$H-NMR (CDCl$_3$): 1.06 (s, 3H, -Me), 1.20-3.00 (m, 21H), 3.85 (s, 3H), 6.56 (s, 1H), 7.11 (s, 1H), 7.64 (s, 1H). MS m/z (TOF ES+): 579 (M+1).

Compound 16

3-((13S,15R)-3-hydroxy-2,4-di iodo-13-methyl-17-oxo-7,8,9,11,12,13,14,15,16,17-decahydro-6H-cyclopenta[a]phenanthren-15-yl)-N-(5-methylthiazol-2-yl)propanamide

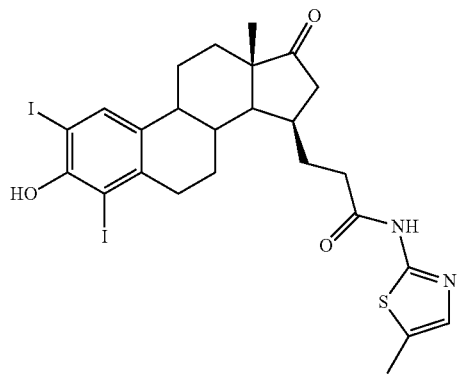 [SMILES: Cc1cnc(NC(=O)CC[C@@H]2CC(=O)[C@@]3(C)CCC4c5cc(I)c(O)c(I)c5CCC4C23)s1]

The compound VII (44 mg, 0.1 mmol) was dissolved into DCM and the mixture was stirred in ice bath. 45 mg (0.2 mmol) of N-iodosuccinimide (NIS) was added and reaction mixture was stirred for 10 min at 0° C. and then reaction was allowed to warm to rt. Water was added after 20 min, the precipitated product was filtered, washed first with water and finally with heptane. Trituration with DCM gave 40% of pure di-iododerivative 16.

MS m/z (TOF ES$^+$): 691 (M+1), 713 (M+Na).

Compound 17

3-((13S,15R)-3-hydroxy-4-iodo-13-methyl-17-oxo-7,8,9,11,12,13,14,15,16,17-decahydro-6H-cyclopenta[a]phenanthren-15-yl)-N-(5-methylthiazol-2-yl)propanamide

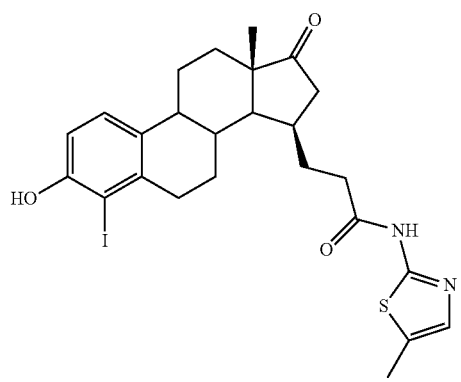 [SMILES: Cc1cnc(NC(=O)CC[C@@H]2CC(=O)[C@@]3(C)CCC4c5ccc(O)c(I)c5CCC4C23)s1]

The compound 9 (23 mg, 0.05 mmol) was dissolved into a mixture of 0.5 ml of THF and 0.5 ml of 2N HCl and the solution chilled to 0° C. An ice-cold solution of NaNO$_2$ (5 mg) was added and stirring continued 15 min. Then 30 mg of KI in 50 ul of water was added and the reaction mixture was stirred at 80° C. for 1 h. Water was added into cooled reaction mixture and product was extracted with ethyl acetate, organic phases were washed with water and dried. After evaporation the product was purified by preparative TLC giving 7 mg of pure 17.

$^1$H-NMR (CDCl$_3$): 1.04 (s, 3H), 1.30-2.95 (m, 21H), 6.84 (d, 1H), 7.06 (s, 1H), 7.19 (d, 1H). MS m/z (TOF ES$^+$): 565 (M+H)

Compound 18

3-((13S,15R)-3-hydroxy-2-iodo-13-methyl-17-oxo-7,8,9,11,12,13,14,15,16,17-decahydro-6H-cyclopenta[a]phenanthren-15-yl)-N-(5-methylthiazol-2-yl)propanamide

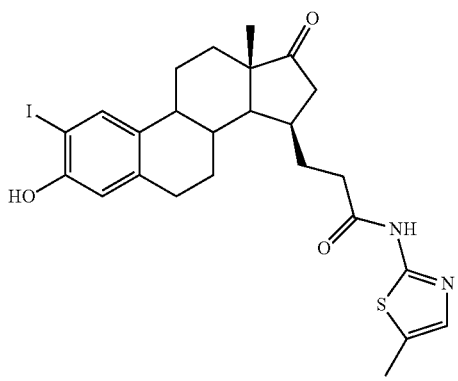 [SMILES: Cc1cnc(NC(=O)CC[C@@H]2CC(=O)[C@@]3(C)CCC4c5cc(I)c(O)cc5CCC4C23)s1]

Prepared using the same method as for the compound 17 using the compound 8 as a starting material $^1$H-NMR (CDCl$_3$): 1.05 (s, 3H), 1.28-2.75 (m, 19H), 2.75-2.90 (m, 2H), 6.74 (s, 1H), 7.05 (s, 1H), 7.51 (s, 1H). MS m/z (TOF ES$^+$): 587 (M+Na)

Compounds 19 to 21

The reaction vessel was charged with VII (2.97 g) in DCM (140 ml) and methanol (20 ml). This solution was added dropwise to the solution of tetrabutylammonium tribromide in DCM/MeOH (v/v 1:1, 10 ml) during 30 minutes by stirring at 0-5° C. After 60 minutes the HPLC analysis showed the formation of three products with traces of unreacted starting material; 41% the monobromide 19, 38% monobromide 20 and 16% dibromide 21.

Compound 19

3-((13S,15R)-2-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

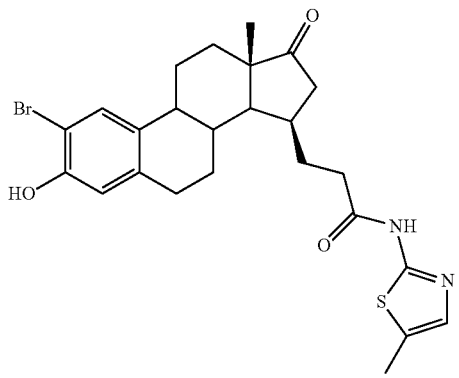 [SMILES: Cc1cnc(NC(=O)CC[C@@H]2CC(=O)[C@@]3(C)CCC4c5cc(Br)c(O)cc5CCC4C23)s1]

$^1$H-NMR (DMSO-d$_6$): 0.96 (s, 3H, -Me), 1.35-2.40 (m, 21H), 2.75 (m, 2H), 6.67 (s, 1H), 7.11 (s, 1H), 7.27 (s, 1H), 9.89 (s, 1H), 11.92 (s, 1H).

Compound 20

3-((13S,15R)-4-bromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

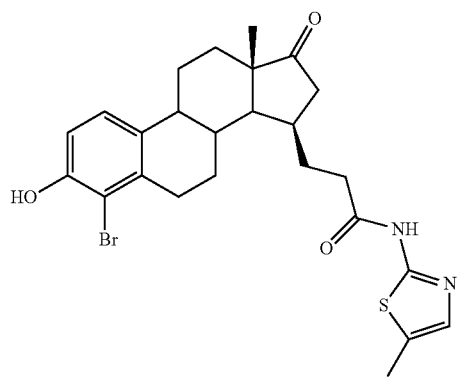 [SMILES: Cc1cnc(NC(=O)CC[C@@H]2CC(=O)[C@@]3(C)CCC4c5ccc(O)c(Br)c5CCC4C23)s1]

$^1$H-NMR (DMSO-d$_6$): 0.95 (s, 3H, -Me), 1.35-2.40 (m, 21H), 2.83 (m, 2H), 6.78 (d, 1H), 7.11 (m, 2H), 7.27 (s, 1H), 9.89 (s, 1H), 11.92 (s, 1H).

Compound 21

3-((13S,15R)-2,4-dibromo-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

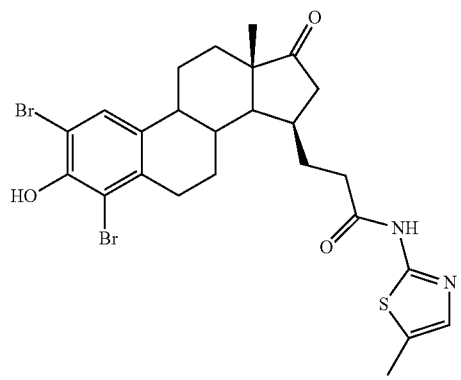 [SMILES: Cc1cnc(NC(=O)CC[C@@H]2CC(=O)[C@@]3(C)CCC4c5cc(Br)c(O)c(Br)c5CCC4C23)s1]

The compound VII (1.0 g, 2.3 mmol) was dissolved in DCM (13 ml), the mixture was cooled to 8° C. and N-bromosuccinimide (NBS) (1.0 g, 5.6 mmol) was added. Reaction mixture was warmed to rt and stirring was continued for 2.5 h. Water was added and precipitated product was filtered, yielding 1.2 g of crystalline dibromide 21.

$^1$H-NMR (DMSO-d$_6$): 0.95 (s, 3H), 1.22-2.32 (m, 19H), 2.79 (m, 2H), 7.12 (s, 1H), 7.40 (s, 1H), 9.55 (s, 1H), 11.92 (s, 1H). MS m/z (TOF ES$^+$): 617/619/621 (M+Na).

Compound 22

3-((13S,15R)-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

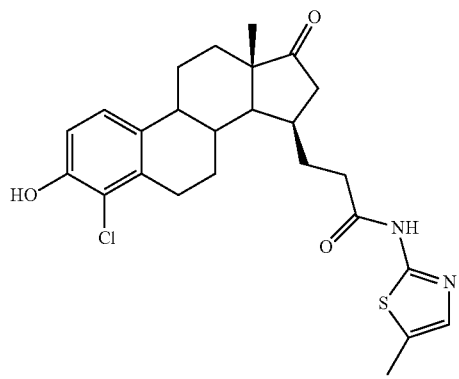 [SMILES: Cc1cnc(NC(=O)CC[C@@H]2CC(=O)[C@@]3(C)CCC4c5ccc(O)c(Cl)c5CCC4C23)s1]

0.5 mmol of the amine compound 9 in 3 ml 2N HCl and 1 ml THF was chilled stirring at 0° C. Solution of 50 mg of NaNO$_2$ in 0.5 ml of water was added dropwise and mixture was stirred for 15 min at this temperature. Then ice bath was removed and preheated solution of 250 mg of CuCl in 5 ml of 2N HCl was added at 80° C. and reaction mixture was kept 2 h at this temperature. After cooling water was added, pH was adjusted to pH 3 and extracted with ethyl acetate, washed with water and brine, dried with Na$_2$SO$_4$ and evaporated. After flash chromatography 85 mg (36%) of the 4-chloro compound 22 was obtained.

$^1$H-NMR (CDCl$_3$): 1.05 (s, 3H), 1.30-3.10 (m, 21H), 6.86 (d, 1H), 7.05 (s, 1H), 7.13 (d, 1H). MS m/z (TOF ES$^+$): 473/475 (M+H).

Compound 23

3-((13S,15R)-2-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

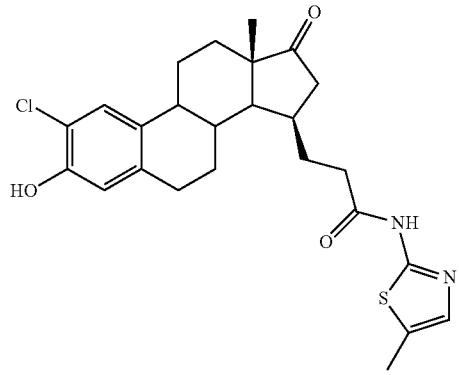

Prepared from the compound 8 by the same method as for the compound 22 in 0.4 mmol scale giving the desired product in 28% yield.

$^1$H-NMR (CDCl$_3$+MeOH-d$_4$): 1.06 (s, 3H), 1.20-2.65 (m, 19H), 2.75-3.05 (m, 2H), 6.70 (s, 1H), 7.03 (s, 1H), 7.18 (s, 1H). MS m/z (TOF ES+): 495/497 (M+Na).

Compound 24

3-((13S,15R)-2,4-dichloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

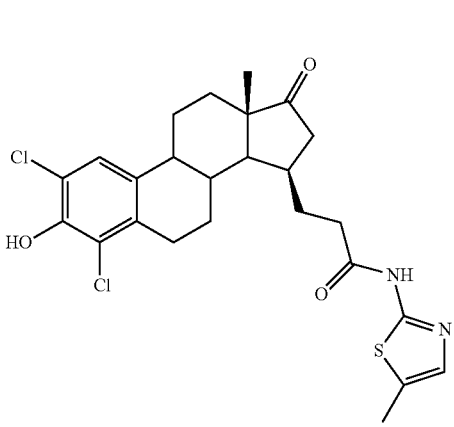

The reaction vessel was charged with the compound VII (4 g) and dry DCM (150 ml) at 0° C. under argon atmosphere. Diethylamine (1.4 ml, 150 mol-%) was added dropwise, followed by sulfuryl chloride (1.1 ml, 150 mol-%). After 30 minutes at 0° C. water was added to the reaction mixture. The organic phase was separated, dried over Na$_2$SO$_4$ and the solvent was evaporated. The residue was purified by column chromatography using DCM/acetone 98:2 as an eluent.

$^1$H-NMR (DMSO-d$_6$): 0.96 (s, 3H), 1.35-2.40 (m, 21H), 2.80 (m, 2H), 7.12 (s, 1H), 7.23 (s, 1H), 9.75 (s, 1H), 11.92 (s, 1H).

Fluorides were prepared from the corresponding amines via thermolysis of their diazonium fluoborate salts in 0.05-0.3 mmol scale.

Compound 25

3-((13S,15R)-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

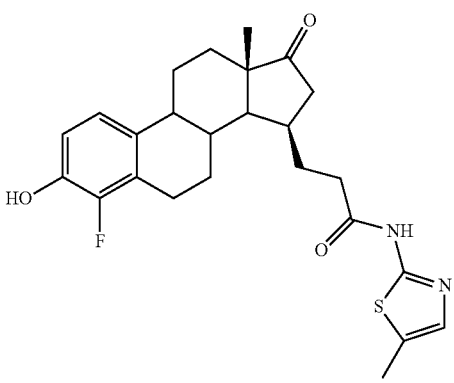 [SMILES: Cc1cnc(NC(=O)CC[C@@H]2CC(=O)[C@@]3(C)CCC4c5ccc(O)c(F)c5CCC4C23)s1]

A mixture of the compound 9 (91 mg, 0.2 mmol), ethanol (2 ml) and 48% tetrafluoroboric acid (0.5 ml) in water was chilled to 0° C. stirring in ice bath. A solution of NaNO$_2$ (20 mg) in 0.2 ml of water was added and stirring continued for 1 h at 0° C. Fluoroborate salt was precipitated by adding diethyl ether until there was no more salt coming out the solution. Ether was decanted and precipitated material was washed twice with diethyl ether and dried in vacuum. The dried fluoroborate salt was heated in a flask at 120-130° C. in a good hood for a couple of hours. The remaining material was treated with DCM and filtered. The solvent was evaporated and the product was purified by flash chromatography affording 22 mg of the 4-fluoride 25.

$^1$H-NMR (CDCl$_3$): 1.04 (s, 3H), 1.30-3.05 (m, 21H), 6.75-6.98 (m, 2H), 7.05 (br s, 1H). MS m/z (TOF ES+): 479 (M+Na).

Compound 26

3-((13S,15R)-2-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

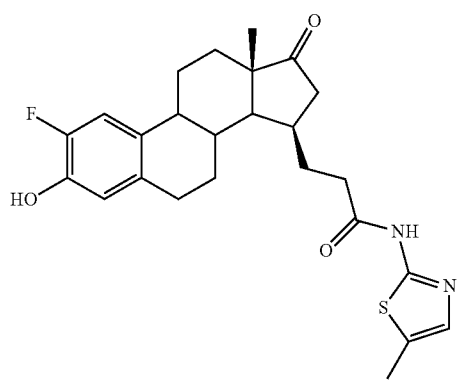 [SMILES: Cc1cnc(NC(=O)CC[C@@H]2CC(=O)[C@@]3(C)CCC4c5cc(F)c(O)cc5CCC4C23)s1]

Prepared from the compound 8 using the method used for the compound 25. The catechol 27 was isolated as a by-product.

$^1$H-NMR (CDCl$_3$): 1.05 (s, 3H), 1.30-2.70 (m, 19H), 2.75-2.90 (m, 2H), 6.73 (d, J=10 Hz, 1H), 6.97 (d, J=14 Hz, 1H), 7.05 (br s, 1H). MS m/z (TOF ES$^+$): 479 (M+Na).

Compound 27

3-((13S,15R)-2,3-dihydroxy-13-methyl-17-oxo-7,8,9,11,12,13,14,15,16,17-decahydro-6H-cyclopenta[a]phenanthren-15-yl)-N-(5-methylthiazol-2-yl)propanamide

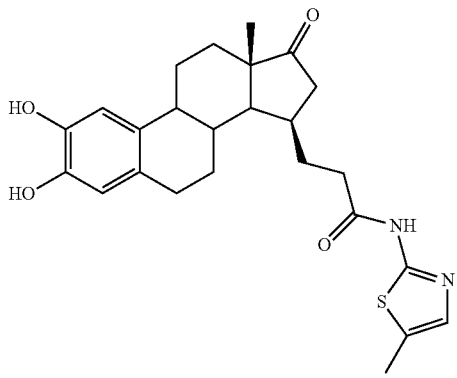

$^1$H-NMR (CDCl$_3$+MeOH-d$_4$): 1.07 (s, 3H), 1.20-2.70 (m, 21H), 7.07 (s, 1H), 7.16 (s, 1H), 7.31 (s, 1H). MS m/z (TOF ES$^+$): 477 (M+Na).

Compound 28

3-{(13S,15R)-2-Bromo-4-fluoro-3-hydroxy-13-methyl-17-oxo-7,8,9,11,12,13,14,15,16,17-decahydro-6H-cyclopenta[a]phenanthren-15-yl}-N-(5-methylthiazol-2-yl)propanamide

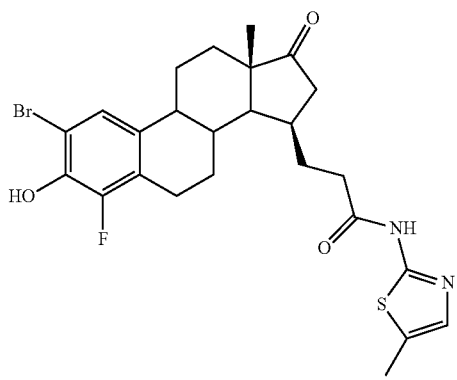 [SMILES: Cc1cnc(NC(=O)CC[C@@H]2CC(=O)[C@@]3(C)CCC4c5cc(Br)c(O)c(F)c5CCC4C23)s1]

The starting material, the compound 25 was brominated by using NBS (120 mol-%) in DCM at 0° C.

$^1$H-NMR (CDCl$_3$): 1.05 (s, 3H), 1.26-2.99 (m, 21H), 7.05 (s, 1H), 7.12 (s, 1H). MS m/z (TOF ES+): 557/559 (M+Na).

Compound 29

3-{(13S,15R)-4-Bromo-2-fluoro-3-hydroxy-13-methyl-17-oxo-7,8,9,11,12,13,14,15,16,17-decahydro-6H-cyclopenta[a]phenanthren-15-yl}-N-(5-methylthiazol-2-yl)propanamide

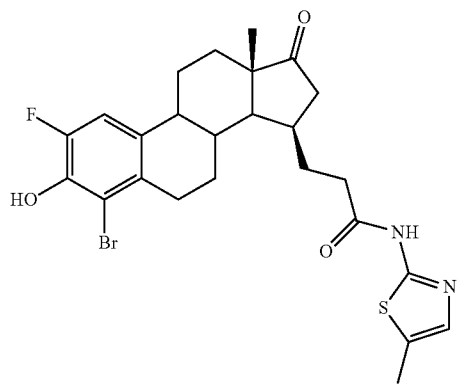 [SMILES: Cc1cnc(NC(=O)CC[C@@H]2CC(=O)[C@@]3(C)CCC4c5cc(F)c(O)c(Br)c5CCC4C23)s1]

The starting material, the compound 26 was brominated by using NBS (120 mol-%) in DCM at 0° C.

$^1$H-NMR (CDCl$_3$): 1.04 (s, 3H), 1.36-2.97 (m, 21H), 6.99 (d, 1H), 7.05 (br s, 1H). MS m/z (TOF ES$^+$): 535/537 (M+H).

Further Aromatic Modifications of Fluorides

Compound 30

3-((13S,15R)-4-fluoro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

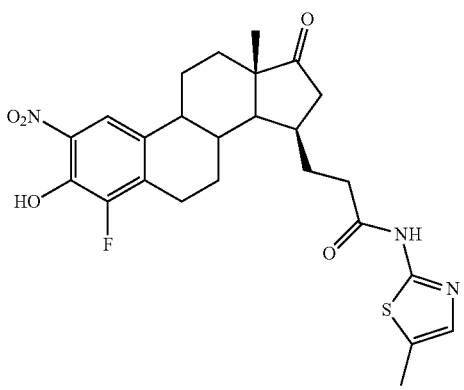

150 mg of the compound 25 was added into a suspension of 55 mg of silica and 55 μl water in a solution of 1.4 ml THF and 1.4 ml DCM and stirred at rt. 340 mg of Silica-sulfuric acid (prepared by adding dropwise 8.0 g of sulphuric acid to 10 g of silica gel, and stirred for 30 minutes at rt) was added, followed by 32 mg of sodium nitrite. Stirring was continued at rt and reaction was monitored by TLC and HPLC. After the reaction was completed silica was filtered off, washed with DCM and finally with DCM-methanol. Solvents were evaporated and the product was purified by flash chromatography giving 40 mg of the compound 30.

$^1$H-NMR (CDCl$_3$): 1.07 (s, 3H), 1.30-3.20 (m, 21H), 7.05 (s, 1H), 7.82 (s, 1H). MS m/z (TOF ES+): 502 (M+H).

Compound 31

3-((13S,15R)-2-amino-4-fluoro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

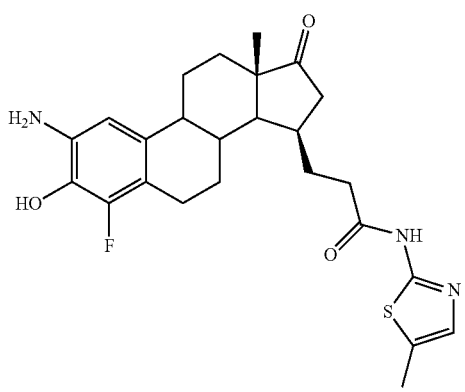 [SMILES: Cc1cnc(NC(=O)CC[C@@H]2CC(=O)[C@@]3(C)CCC4c5cc([N+](=O)[O-])c(O)c(F)c5CCC4C23)s1]

Prepared by hydrogenation of the compound 30 in ethanol containing 20% of THF with Pd/C at 25-30° C.

$^1$H-NMR (CDCl$_3$): 1.06 (s, 3H), 1.30-2.50 (m, 21H), 6.48 (s, 1H), 6.58 (s, 1H). MS m/z (TOF ES+): 494 (M+Na).

Compound 32

3-((13S,15R)-4-chloro-3-hydroxy-13-methyl-2-nitro-17-oxo-7,8,9,11,12,13,14,15,16,17-decahydro-6H-cyclopenta[a]phenanthren-15-yl)-N-(5-methylthiazol-2-yl)propanamide

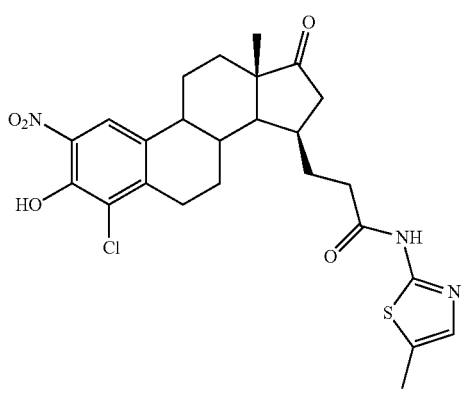 [SMILES: Cc1cnc(NC(=O)CC[C@@H]2CC(=O)[C@@]3(C)CCC4c5cc([N+](=O)[O-])c(O)c(Cl)c5CCC4C23)s1]

Prepared from the compound 22 as described for the compound 30 above.

$^1$H-NMR (CDCl$_3$): 1.07 (s, 3H), 1.35-3.20 (m, 21H), 7.05 (s, 1H), 7.99 (s, 1H). MS m/z (TOF ES+): 518/520 (M+H).

Compound 33

3-((13S,15R)-2-amino-4-chloro-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

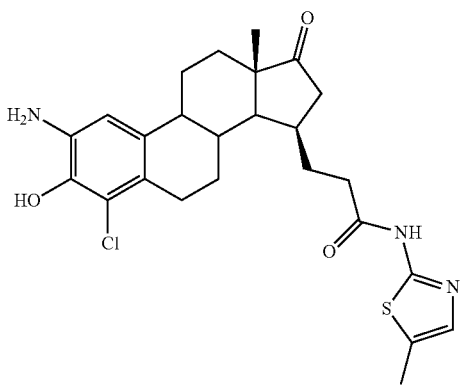 [SMILES: Cc1cnc(NC(=O)CC[C@@H]2CC(=O)[C@@]3(C)CCC4c5cc(N)c(O)c(Cl)c5CCC4C23)s1]

Prepared by hydrogenation of the compound 32 in ethanol containing 20% of THF with Pd/C catalyst at 25-30° C.

$^1$H-NMR (CDCl$_3$+MeOH-d$_4$): 1.05 (s, 3H), 1.35-3.00 (m, 21H), 6.64 (s, 1H), 7.04 (s, 1H). MS m/z (TOF ES+): 510/512 (M+Na).

Halogenated Heterocyclic Compounds

Compound 34

3-((3R,12aS)-6-chloro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

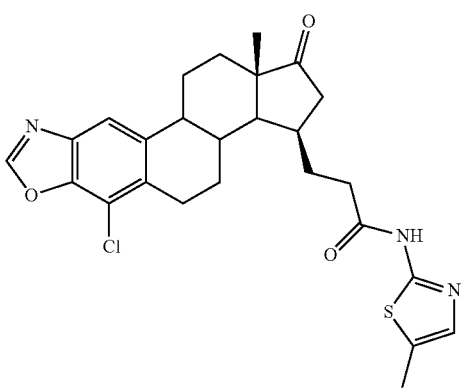 [SMILES: Cc1cnc(NC(=O)CC[C@@H]2CC(=O)[C@@]3(C)CCC4c5cc6ncoc6c(Cl)c5CCC4C23)s1]

The compound 34 was prepared from the compound 33 using trimethyl ortoformate as reagent as described for the compound 12.

$^1$H-NMR (CDCl$_3$): 1.07 (s, 3H), 1.40-3.45 (m, 21H), 7.06 (s, 1H), 7.66 (s, 1H), 8.06 (s, 1H), 11.89 (br s, 1H). MS m/z (TOF ES+): 498/500 (M+H).

Compound 35

3-((3R,12aS)-6-fluoro-12a-methyl-1-oxo-2,3,3a,3b,4,5,10b,11,12,12a-decahydro-1H-cyclopenta[7,8]phenanthro[3,2-d]oxazol-3-yl)-N-(5-methylthiazol-2-yl)propanamide

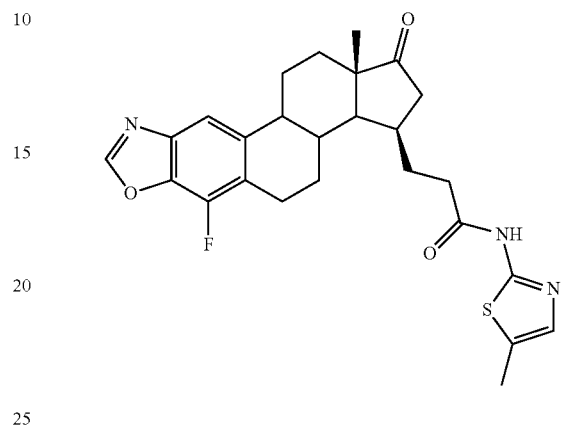

The compound 35 was prepared from the compound 31 with trimethyl ortoformate, by using the method described for the compound 12.

$^1$H-NMR (CDCl$_3$): 1.08 (s, 3H), 1.40-3.20 (m, 21H), 7.05 (s, 1H), 7.52 (s, 1H), 8.03 (s, 1H), 11.91 (br s, 1H). MS m/z (TOF ES+): 482 (M+H).

Synthesis of C3-Deoxo-Derivatives from Triflates

Compound 36

(13S,15R)-13-methyl-15-(3-((5-methylthiazol-2-yl)amino)-3-oxopropyl)-17-oxo-7,8,9,11,12,13,14,15,16,17-decahydro-6H-cyclopenta[a]phenanthrenanthren-3-yl trifluoromethanesulfonate

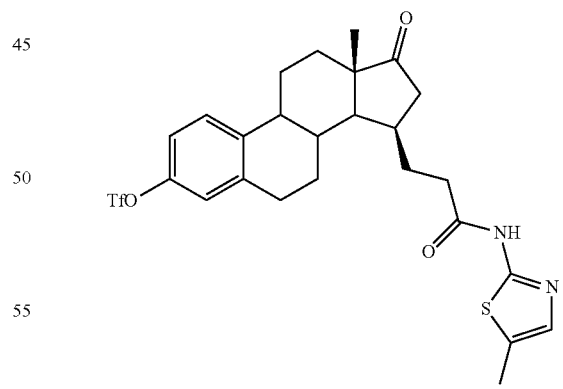

The compound VII (877 mg, 2 mmol) was dissolved into 16 ml of DCM under nitrogen atmosphere. Triethylamine (TEA) (1.0 g, 1 mmol) was added giving a clear solution. Into this solution at 0° C. was added triflic anhydride (512 µl, 3 mmol). Reaction mixture was then allowed to warm to rt and stirring was continued overnight. Reaction mixture was poured into ice-water. Phases were separated and aqueous phase was extracted twice with DCM. The combined extracts were washed twice with water, dried with Na₂SO₄ and evaporated giving after flash chromatography using DCM-MeOH (85:15) as an eluent 1.00 g (87%) of triflate 36.

¹H-NMR (DMSO-d₆): 0.98 (s, 3H), 1.25-2.50 (m, 19H), 2.85-3.00 (m, 2H), 7.11 (s, 1H), 7.22 (d+s, 2H), 7.46 (d, 1H), 11.91 (s, 1H). MS m/z (TOF ES⁺): 593 (M+Na).

Compound 37

3-((13S,15R)-13-methyl-17-oxo-7,8,9,11,12,13,14,15,16,17-decahydro-6H-cyclopenta[a]phenanthren-15-yl)-N-(5-methylthiazol-2-yl)propanamide

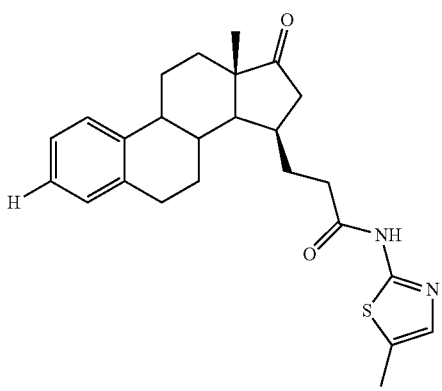 [SMILES: Cc1cnc(NC(=O)CC[C@@H]2CC(=O)[C@@]3(C)CCC4c5ccccc5CCC4C23)s1]

The triflate 36 (257 mg, 0.45 mmol, 100 mol-%), 1,1'-bis[(diphenylphosphino)ferrocene]dichloropalladium(II) (22 mg, 0.027 mmol, 6 mol-%), TEA (0.19 ml, 1.35 mmol, 300 mol-%) and 4 ml of toluene were charged into reaction vessel. The vessel was closed with a septum and flushed using vacuum/nitrogen, formic acid (33 µl, 0.9 mmol, 200 mol-%) was added and the mixture stirred at 90° C. for 3 h. The reaction mixture was filtered through celite washed several times with toluene. Combined toluene fractions were washed thrice with 1 N HCl and then with water, dried and evaporated giving 178 mg (92%) of raw product, after flash chromatography 133 mg (70%) of pure 37.

¹H-NMR (DMSO-d₆): 0.98 (s, 3H), 1.25-2.45 (m, 19H), 2.80-2.95 (m, 2H), 7.05-7.15 (m, 4H), 7.20-7.35 (m, 1H), 11.93 (s, 1H). MS m/z (TOF ES⁺): 445 (M+Na).

Compound 38

3-((13S,15R)-2-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

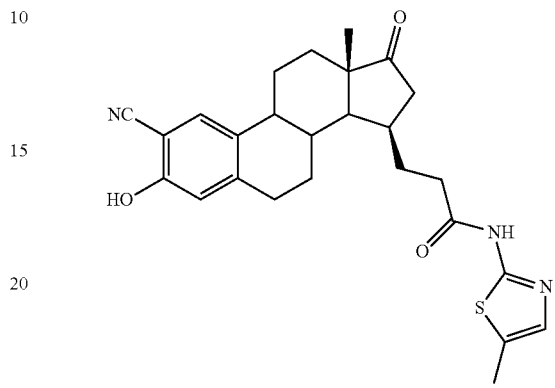

The C-2 bromide 19 (50 mg, 100 mol-%) and copper(I) cyanide (230 mol-%) were dissolved in dry DMF (5 ml) and refluxed under nitrogen for six hours. The reaction mixture was cooled and FeCl₃ (5000 mol-%) in conc. HCl (500 µl) was added, and stirred at 55-60° C. for 30 minutes. The reaction mixture was cooled, diluted with water. The product was extracted with EtOAc, washed with water, sat. NaHCO₃-solution until pH was 8, and finally with brine. Purification by chromatography.

¹H-NMR (CDCl3+MeOH-d₄): 1.05 (s, 3H), 1.40-2.65 (m, 19H), 2.89 (m, 2H), 6.70 (s, 1H), 7.06 (s, 1H), 7.36 (s, 1H).

Compound 39

3-((13S,15R)-4-cyano-3-hydroxy-13-methyl-17-oxo-7,8,9,11,12,13,14,15,16,17-decahydro-6H-cyclopenta[a]phenanthren-15-yl)-N-(5-methylthiazol-2-yl)propanamide

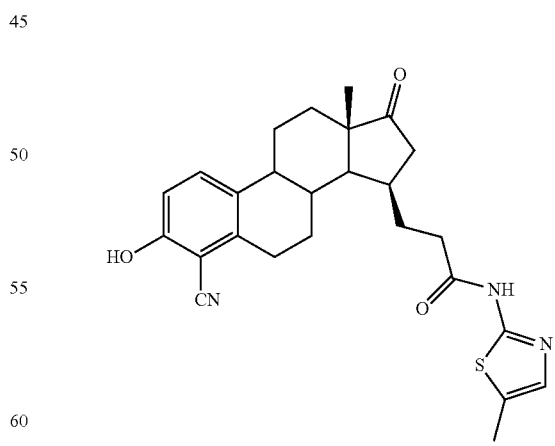

Prepared according to method used for the compound 38 using the C-4 bromide 20 as a starting material.

¹H-NMR (CDCl3+MeOH-d₄): 1.03 (s, 3H), 1.22-2.56 (m, 19H), 3.05 (m, 2H), 6.76 (d, 1H), 7.06 (s, 1H), 7.31 (s, 1H). MS m/z (TOF ES⁺): 464 (M+1).

Preparation of C-16,17-Pyrazole Derivatives

Pyrazoles were prepared via C-16-hydroxymethylene derivatives, which were prepared using the general method: C-17 ketone (1 mmol) was dissolved into THF (5 ml), toluene (20 ml) and ethylformate (5 ml) under nitrogen atmosphere. Sodium hydride (4 mmol) was added and stirring was continued at rt overnight. The heterocyclic ring formation was achieved by addition of hydrazine hydrate in methanol.

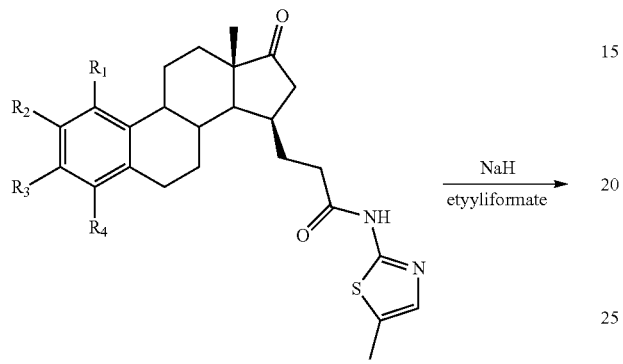

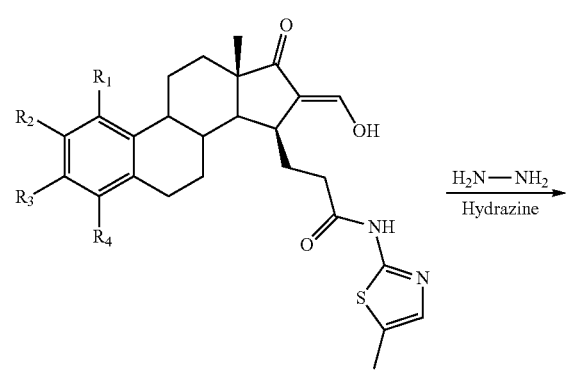

Compound 40

3-{(13S,15S)-3-Hydroxy-16-[1-hydroxy-methyl-idene]-13-methyl-17-oxo-7,8,9,11,12,13,14,15,16,17-decahydro-6H-cyclopenta[a]phenanthren-15-yl}-N-(5-methylthiazol-2-yl)propanamide

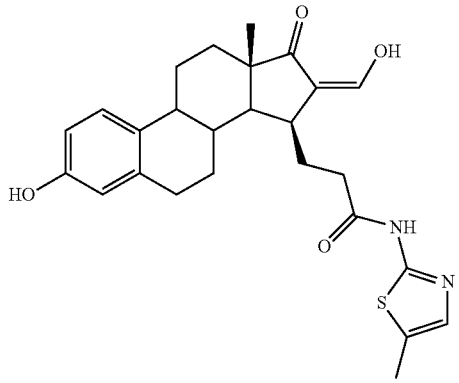 [SMILES: Cc1cnc(NC(=O)CC[C@@H]2/C(=C/O)C(=O)[C@@]3(C)CCC4c5ccc(O)cc5CCC4C23)s1]

The compound VII (100 mol-%) was dissolved into THF (1 ml) under nitrogen atmosphere. Toluene (4 ml) was added to the reaction mixture followed by addition of ethyl formate (6000 mol-%). Sodium hydride (50%) (450 mol-%) was added and the reaction mixture was stirred overnight at rt. Additional amount of ethyl formate (6000 mol-%) and sodium hydride (450 mol-%) was added to the reaction mixture and stirring was continued overnight at rt. pH was adjusted to neutral with 0.5 N HCl and the solvents were evaporated. Water was added to the residue and extracted with EtOAc (3×10 ml). The combined organic phases were washed with water (10 ml) and brine (3×10 ml), dried over Na$_2$SO$_4$, filtered and evaporated. The product 40 was obtained in quantitative yield.

$^1$H-NMR (DMSO-d$_6$): 0.96 (s, 3H), 1.20-2.95 (m, 19H), 6.45 (s, 1H), 6.48 (d, 1H), 7.02 (d, 1H), 7.08 (s, 1H), 7.72 (s, 1H), 9.01 (s, 1H) 12.43 (br s, 1H). MS m/z (TOF ES$^+$): 489 (M+Na)

Compound 41

3-{(13S,15S)-16-[1-Hydroxy-methyl idene]-13-methyl-17-oxo-7,8,9,11,12,13,14,15,16,17-deca-hydro-6H-cyclopenta[a]phenanthren-15-yl}-N-(5-methylthiazol-2-yl)propanamide

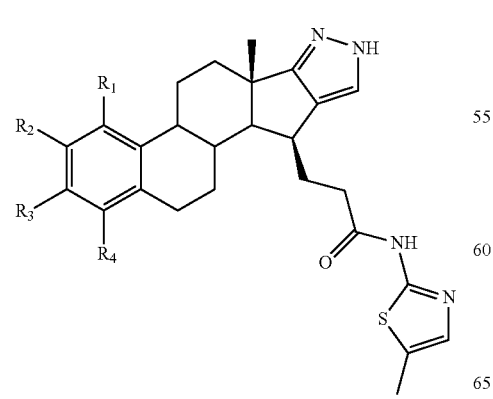

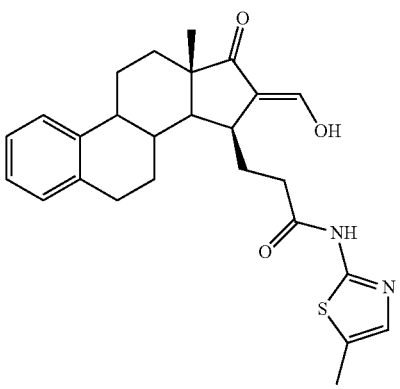 [SMILES: Cc1cnc(NC(=O)CC[C@@H]2/C(=C\O)C(=O)[C@@]3(C)CCC4c5ccccc5CCC4C23)s1]

Prepared by the method used for preparation of the compound 40 using the compound 37 as a starting material.
$^1$H-NMR (CDC3): 1.12 (s, 3H), 1.30-3.0 (m, 19H), 7.0-7.3 (m, 5H). MS m/z (TOF ES$^+$): 451 (M+H).

Compound 42

3-{(13S,15S)-16-[1-Hydroxy-methylidene]-3-methoxy-13-methyl-17-oxo-7,8,9,11,12,13,14,15,16,17-decahydro-6H-cyclopenta[a]phenanthren-15-yl}-N-(5-methylthiazol-2-yl)propanamide

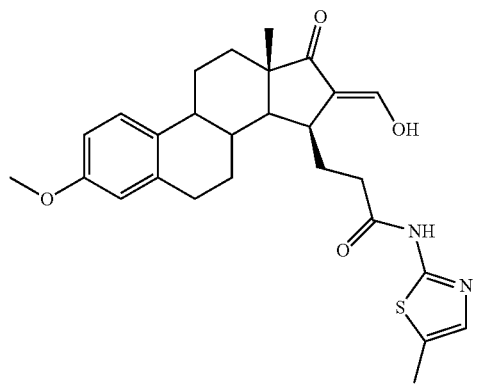 [SMILES: COc1ccc2c(c1)CCC1C2CC[C@]2(C)C(=O)/C(=C/O)[C@@H](CCC(=O)Nc3ncc(C)s3)C12]

Prepared by the method used for preparation of the compound 40 using the compound 2 as a starting material (quantitative yield).
$^1$H-NMR (CDCl$_3$+MeOH-d$_4$): 0.97 (t, 3H), 1.15-2.40 (m, 16H), 2.84 (m, 3H), 3.69 (s, 3H), 6.64 (s, 1H), 6.66 (d, 1H), 7.08 (s, 1H), 7.15 (d 1H), 8.13 (s, 1H). MS m/z (TOF ES$^+$): 503 (M+Na), 481 (M+1).

Compound 43

3-{(13S,15S)-2-tert-Butyl-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

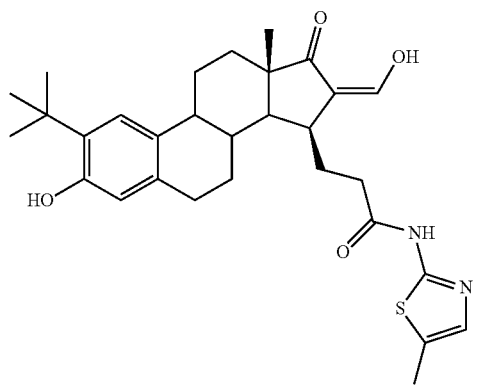 [SMILES: Cc1cnc(NC(=O)CC[C@@H]2/C(=C/O)C(=O)[C@@]3(C)CCC4c5cc(C(C)(C)C)c(O)cc5CCC4C23)s1]

Prepared by the method used for preparation of the compound 40 using the compound 3 as a starting material (74% yield).

$^1$H-NMR (DMSO-d$_6$): 0.99 (s, 3H), 1.05-3.00 (m, 32H), 6.46 (s, 1H), 7.00 (s, 1H), 7.09 (s, 1H), 7.58 (s, 1H), 8.95 (s, 1H), 12.01 (s, 1H). MS m/z (TOF ES$^+$): 523 (M+1), 545 (M+Na).

Compound 44

3-{(13S,15S)-2-Bromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

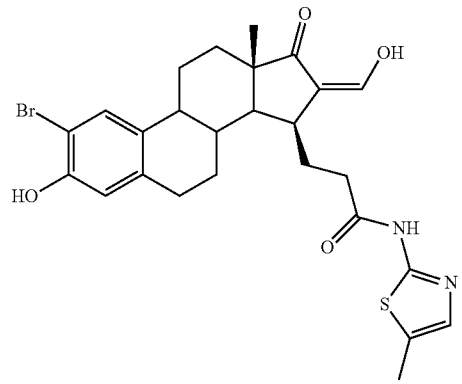 [SMILES: Cc1cnc(NC(=O)CC[C@@H]2/C(=C/O)C(=O)[C@@]3(C)CCC4c5cc(Br)c(O)cc5CCC4C23)s1]

Prepared by the method used for preparation of the compound 40 using the compound 19 as a starting material.
$^1$H-NMR (CDCl$_3$): 1.13 (s, 3H), 1.40-2.9 (m, 19H), 3.40 (s, 1H), 6.76 (d, 1H) 7.05 (s, 1H), 7.32 (d, 1H). MS m/z (TOF ES$^-$): 543/545

Compound 45

3-{(13S,15S)-4-Bromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

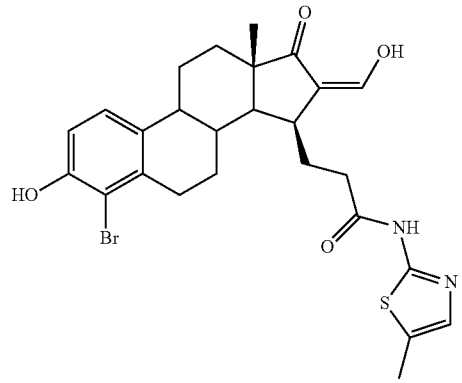 [SMILES: Cc1cnc(NC(=O)CC[C@@H]2/C(=C/O)C(=O)[C@@]3(C)CCC4c5ccc(O)c(Br)c5CCC4C23)s1]

Prepared by the method used for preparation of the compound 40 using the compound 20 as a starting material.
$^1$H-NMR (CDCl$_3$): 1.12 (s, 3H), 1.40-3.0 (m, 19H), 3.67 (s, 1H), 6.86 (d, 1H) 7.06 (s, 1H), 7.16 (d, 1H). MS m/z (TOF ES$^+$): 545/547

Compound 46

3-{(13S,15S)-2,4-Dibromo-3-hydroxy-16-[1-hydroxy-methylidene]-13-methyl-17-oxo-7,8,9,11,12,13,14,15,16,17-decahydro-6H-cyclopenta[a]phenanthren-15-yl}-N-(5-methylthiazol-2-yl)propanamide

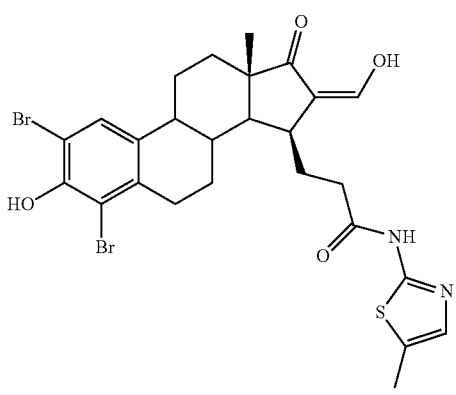 [SMILES: Cc1cnc(NC(=O)CC[C@@H]2/C(=C/O)C(=O)[C@@]3(C)CCC4c5cc(Br)c(O)c(Br)c5CCC4C23)s1]

Prepared by the method used for preparation of the compound 40 using the compound 21 as a starting material.

$^{1}$H-NMR (DMSO-d$_6$): 0.96 (s, 3H), 1.20-3.00 (m, 19H), 7.09 (s, 1H), 7.39 (s, 1H), 7.55 (s, 1H), 9.53 (br s, 1H), 11.95 (br s, 1H). MS m/z (TOF ES$^+$): 645/647/649 (M+Na)

Compound 47

3-{(13S,15S)-16-[1-hydroxy-methylidene]-2-iodo-3-methoxy-13-methyl-17-oxo-7,8,9,11,12,13,14,15,16,17-decahydro-6H-cyclopenta[a]phenanthren-15-yl}-N-5-methylthiazol-2-yl)propanamide

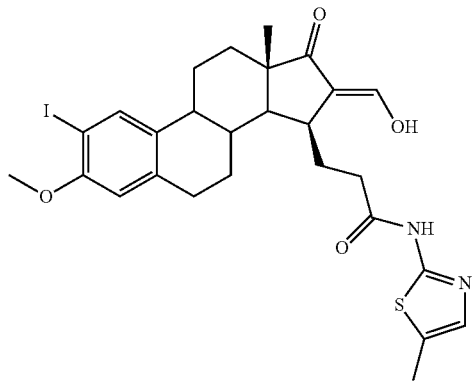 [SMILES: COc1cc2c(cc1I)C1CC[C@]3(C)C(=O)/C(=C/O)[C@@H](CCC(=O)Nc4ncc(C)s4)C3C1CC2]

Prepared by the method used for preparation of the compound 40 using the compound 15 as a starting material (yield 74%).

$^{1}$H-NMR (CDCl$_3$): 1.14 (s, 3H), 1.20-2.97 (m, 20H), 3.85 (s, 3H), 6.57 (s, 1H) 7.07 (s, 1H), 7.63 (s, 1H). MS m/z (TOF ES$^+$): 607 (M+1).

Compound 48

3-{(13S,15S)-3-hydroxy-16-[1-hydroxy-methylidene]-13-methyl-2-nitro-17-oxo-7,8,9,11,12,13,14,15,16,17-decahydro-6H-cyclopenta[a]phenanthren-15-yl}-N-(5-methylthiazol-2-yl)propanamide

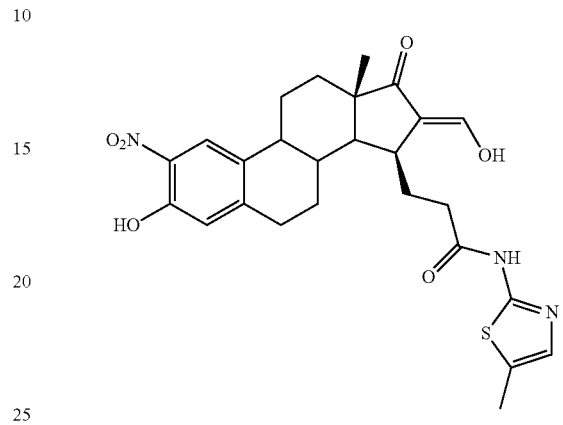

Prepared by the method used for preparation of the compound 40 using the compound 5 as a starting material.

$^{1}$H-NMR (CDCl$_3$): 1.14 (s, 3H), 1.20-3.05 (m, 19H), 6.88 (s, 1H), 7.04 (s, 1H), 7.23 (s, 1H), 7.97 (s, 1H). MS m/z (TOF ES$^+$): 534 (M+Na).

Compound 49

3-{(13S,15S)-3-hydroxy-16-[1-hydroxy-methylidene]-13-methyl-4-nitro-17-oxo-7,8,9,11,12,13,14,15,16,17-decahydro-6H-cyclopenta[a]phenanthren-15-yl}-N-(5-methylthiazol-2-yl)propanamide

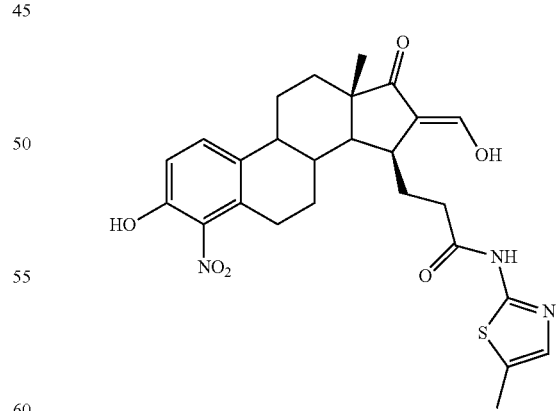

Prepared by the method used for preparation of the compound 40 using the compound 6 as a starting material.

$^{1}$H-NMR (CDCl$_3$): 1.14 (s, 3H), 1.30-3.35 (m, 19H), 6.97 (d, 1H), 7.06 (s, 1H), 7.44 (d, 1H). MS m/z (TOF ES$^+$): 534 (M+Na).

Synthesis of C-16,17-Pyrazoles

Compound 50

3-((6aS,10S)-2-Methoxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide

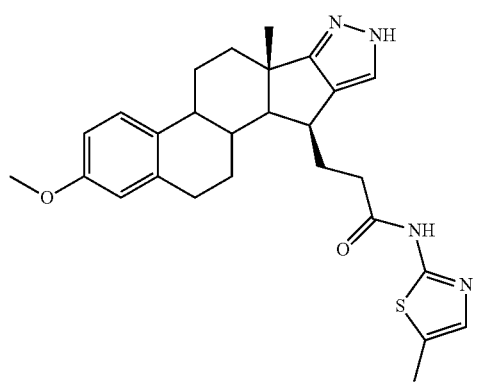 [SMILES: COc1ccc2c(c1)CCC1C2CC[C@]2(C)c3n[nH]cc3[C@@H](CCC(=O)Nc3ncc(C)s3)C12]

Hydrazine hydrate (0.1 ml) was added into a solution of 42 (440 mg, 0.91 mmol) in methanol (10 ml) and the reaction mixture was stirred at rt overnight. Additional amount of hydrazine hydrate (0.3 ml) was added and stirring was continued until all the starting material had disappeared. The reaction mixture was evaporated and the crude product was purified by flash chromatography using DCM-methanol 24:1 as an eluent giving 240 mg (0.50 mmol, 55%) of the product.

$^1$H-NMR (DMSO-d$_6$+CDCl$_3$): 1.11 (t, 3H), 1.25-2.40 (m, 16H), 2.86 (m, 3H), 3.70 (s, 3H), 6.60 (s, 1H), 6.62 (d, 1H), 7.02 (s, 1H), 7.11 (d, 1H), 7.30 (s, 1H), 11.86 (s, 1H), 12.00 (br s, 1H). MS m/z (TOF ES$^+$): 499 (M+Na), 477 (M+1).

Compound 51

3-((6aS,10S)-2-Hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide

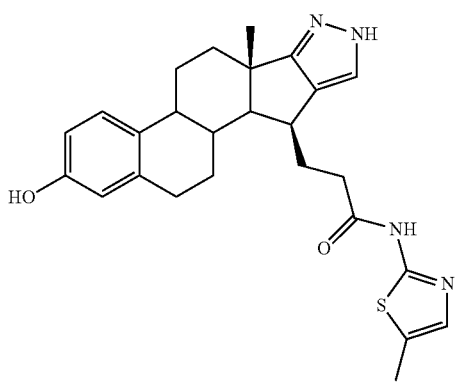 [SMILES: Cc1cnc(NC(=O)CC[C@@H]2c3c[nH]nc3[C@@]3(C)CCC4c5ccc(O)cc5CCC4C23)s1]

Prepared by the method used for preparation of the compound 50 using the compound 40 as a starting material $^1$H-NMR (DMSO-d$_6$): 1.08 (s, 3H), 1.22-2.32 (m, 16H), 2.65-2.90 (m, 3H), 6.47-6.52 (m, 2H), 7.03-7.10 (m, 2H), 7.35 (s, 1H), 9.05 (s, 1H), 11.94 (s, 1H), 12.12 (s, 1H). MS m/z (TOF ES$^+$): 485 (M+Na)

Compound 52

3-((6aS,10S)-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide

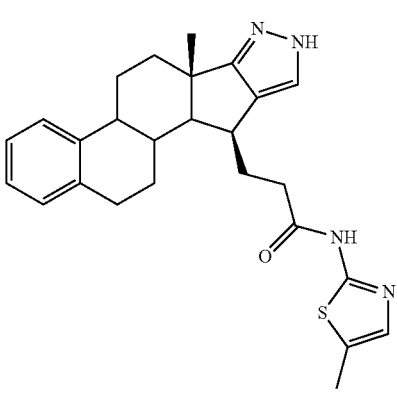 [SMILES: Cc1cnc(NC(=O)CC[C@@H]2c3c[nH]nc3[C@@]3(C)CCC4c5ccccc5CCC4C23)s1]

Prepared by the method used for preparation of the compound 50 using the compound 41 as a starting material.

$^1$H-NMR (CDCl$_3$): 1.11 (s, 3H), 1.30-3.10 (m, 19H), 5.74 (s, 1H), 6.56 (s, 1H), 7.0-7.30 (m, 5H), 12.39 (br s, 1H). MS m/z (TOF ES$^+$): 447 (M+H).

Compound 53

3-((6aS,10S)-3-tert-Butyl-2-hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide

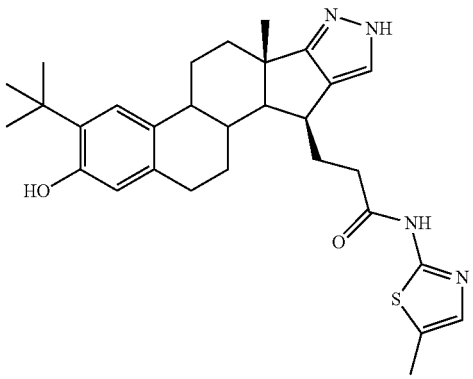 [SMILES: Cc1cnc(NC(=O)CC[C@@H]2c3c[nH]nc3[C@@]3(C)CCC4c5cc(C(C)(C)C)c(O)cc5CCC4C23)s1]

Prepared by the method used for preparation of the compound 50 using the compound 43 as a starting material (56% yield).

$^1$H-NMR (CDCl$_3$+MeOH-d$_4$): 1.20 (s, 3H), 1.32-3.15 (m, 28H), 6.48 (s, 1H), 6.98 (s, 1H), 7.18 (s, 1H), 7.22 (s, 1H). MS m/z (TOF ES$^+$): 519 (M+1).

Compound 54

3-{(6aS,10S)-1,3-dibromo-2-hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide

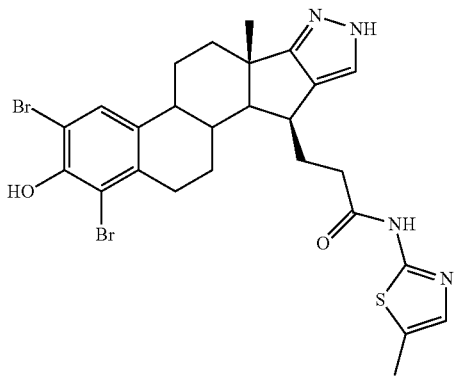 [SMILES: Cc1cnc(NC(=O)CC[C@@H]2c3c[nH]nc3[C@@]3(C)CCC4c5cc(Br)c(O)c(Br)c5CCC4C23)s1]

Prepared by the method used for preparation of the compound 50 using the compound 46 as a starting material $^1$H-NMR (DMSO-d$_6$): 1.08 (s, 3H), 1.10-2.40 (m, 19H), 2.65-2.90 (m, 3H), 7.12 (s, 1H), 7.37 (s, 1H), 7.41 (s, 1H), 9.54 (s, 1H), 11.95 (br s, 1H), 12.15 (brs, 1H).

Compound 55

3-{(6aS,10S)-2-Hydroxy-6a-methyl-2-nitro-4b,5,6,6a,8,10,10a,10b,11,12-decehydro-7,8-diaza-pentaleno[2,1-1]phenanthren-10-yl}-N-(5-methylthiazol-2-yl)propanamide

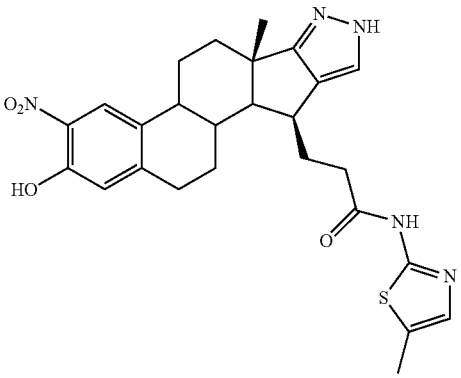 [SMILES: Cc1cnc(NC(=O)CC[C@@H]2c3c[nH]nc3[C@@]3(C)CCC4c5cc([N+](=O)[O-])c(O)cc5CCC4C23)s1]

Prepared by the method used for preparation of the compound 50 using the compound 48 as a starting material.

$^1$H-NMR (CDCl$_3$+MeOH-d$_4$): 1.24 (s, 3H), 1.45-2.70 (m, 16H), 2.90-3.10 (m, 3H), 6.91 (s, 1H), 7.04 (s, 1H), 7.36 (s, 1H), 8.00 (s, 1H). MS m/z (TOF ES$^+$): 530 (M+Na)

Compound 56

3-{(6aS,10S)-2-Hydroxy-6a-methyl-4-nitro-4b,5,6,6a,8,10,10a,10b,11,12-decehydro-7,8-diaza-pentaleno[2,1-1]phenanthren-10-yl}-N-(5-methylthiazol-2-yl)propanamide

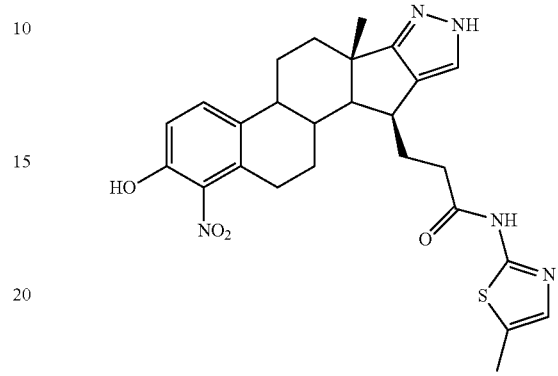

Prepared by the method used for preparation of the compound 50 using the compound 49 as a starting material.

$^1$H-NMR (CDCl$_3$+MeOH-d$_4$): 1.22 (s, 3H), 1.40-3.10 (m, 19H), 6.86 (d, 1H), 7.02 (s, 1H), 7.25-7.40 (m, 2H). MS m/z (TOF ES$^+$): 508 (M+H)

Synthesis of C-17 Oximes

C-17-Oximes were synthesized from C-17 ketones using the method described below:

Ketone (0.3 mmol) was dissolved in a mixture of ethanol (3 ml) and THF (2 ml) under nitrogen atmosphere. Pyridine (1.5 mmol) and hydroxylamine hydrochloride (0.9 mmol) were added to this solution. The reaction mixture was refluxed for 1-2 h. Solvents were evaporated. Water was added and the product was either filtered or extracted with ethyl acetate, washed with dilute hydrochloric acid and finally with water. Oximes were purified further by flash-chromatography if required.

Compound 57

3-{(13S,15R)-3-Hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

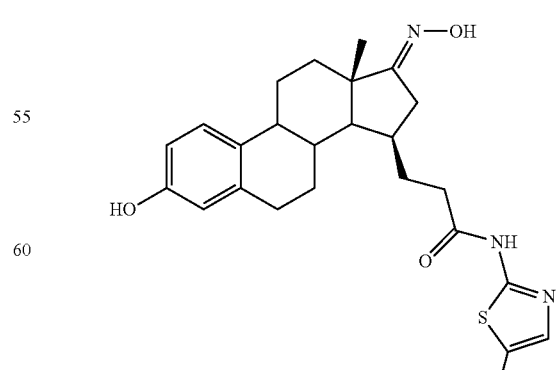

Prepared using the general method above using the compound VII as a starting material.

$^1$H-NMR (DMSO-d$_6$): 1.02 (s, 3H), 1.2-2.9 (m, 21H), 6.46 (s, 1H), 6.50 (d, 3H), 7.04 (d, 1H), 7.12 (s, 1H), 9.02 (s, 1H), 10.18 (s, 1H), 11.92 (s, 1H). MS m/z (TOF ES$^+$): 476 (M+Na).

Compound 58

3-{(13S,15R)-2-tert-Butyl-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazo-2-yl)propanamide

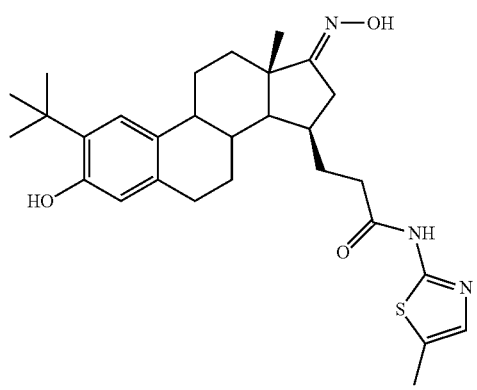 [SMILES: Cc1cnc(NC(=O)CC[C@@H]2C/C(=N\O)[C@@]3(C)CCC4c5cc(C(C)(C)C)c(O)cc5CCC4C23)s1]

Prepared using the general method above using the compound 3 as a starting material in 95% yield.

$^1$H-NMR (CDCl$_3$+MeOH-d$_4$): 1.11 (s, 3H), 1.3-3.1 (m, 34H), 6.46 (s, 1H), 7.05 (s, 1H), 7.15 (s, 1H). MS m/z (TOF ES$^+$): 532 (M+Na).

Compound 59

3-{(13S,15R)-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

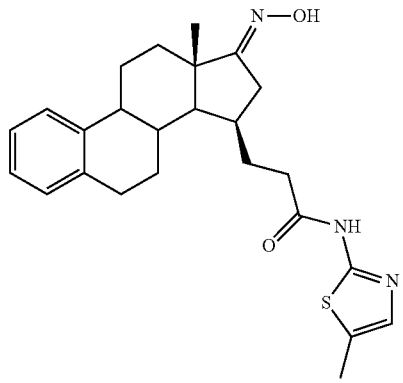 [SMILES: Cc1cnc(NC(=O)CC[C@@H]2C/C(=N\O)[C@@]3(C)CCC4c5ccccc5CCC4C23)s1]

Prepared using the general method above using the compound 37 as a starting material.

$^1$H-NMR (CDCl$_3$): 1.14 (s, 3H), 1.35-2.75 (m, 18H), 2.80-3.05 (m, 3H), 7.05-7.40 (m, 5H), 8.35 (s, 1H), 11.48 (s, 1H). MS m/z (TOF ES$^+$): 460 (M+Na).

Compound 60

3-{(13S,15R)-3-Hydroxy-2-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

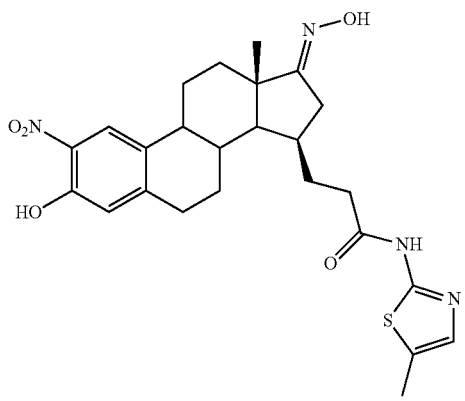 [SMILES: Cc1cnc(NC(=O)CC[C@@H]2C/C(=N\O)[C@@]3(C)CCC4c5cc([N+](=O)[O-])c(O)cc5CCC4C23)s1]

Prepared using the general method above using the compound 5 as a starting material.

$^1$H-NMR (CDCl$_3$): 1.15 (s, 3H), 1.30-2.75 (m, 18H), 2.85-3.05 (m, 3H), 6.87 (s, 1H), 7.06 (s, 1H), 7.97 (s, 1H) 8.50 (br s, 1H), 10.55 (br s, 1H). MS m/z (TOF ES$^+$): 499 (M+H).

Compound 61

3-{(13S,15R)-3-Hydroxy-4-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

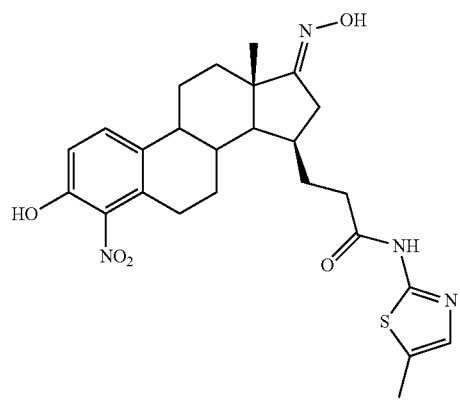 [SMILES: Cc1cnc(NC(=O)CC[C@@H]2C/C(=N\O)[C@@]3(C)CCC4c5ccc(O)c([N+](=O)[O-])c5CCC4C23)s1]

Prepared using the general method above using the compound 6 as a starting material.

1H-NMR (CDCl$_3$+MeOH-d$_4$): 1.13 (s, 3H), 1.30-3.30 (m, 21H), 6.91 (d, 1H), 7.04 (s, 1H), 7.39 (d, 1H). MS m/z (TOF ES$^+$): 521 (M+Na).

Compound 62

3-{(13S,15R)-2-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

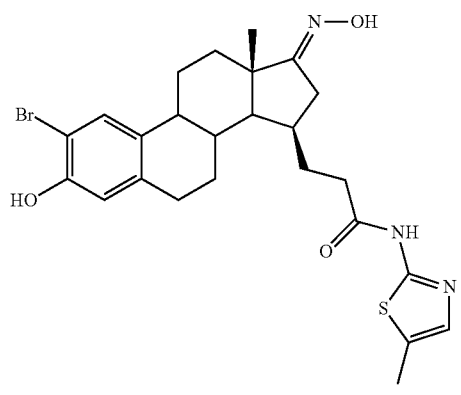 [SMILES: Cc1cnc(NC(=O)CC[C@@H]2C/C(=N\O)[C@@]3(C)CCC4c5cc(Br)c(O)cc5CCC4C23)s1]

Prepared using the general method above using the C-2 monobromide 19 as a starting material.

1H-NMR (CDCl$_3$+MeOH-d$_4$): 1.11 (s, 3H), 1.2-3.0 (m, 18H), 2.40 (s, 3H), 6.69 (s, 1H), 7.04 (s, 1H), 7.32 (d, 1H). MS m/z (TOF ES$^+$): 532/534.

Compound 63

3-{(13S,15R)-4-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

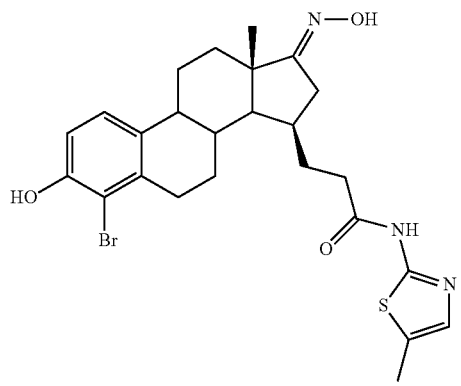 [SMILES: Cc1cnc(NC(=O)CC[C@@H]2C/C(=N\O)[C@@]3(C)CCC4c5ccc(O)c(Br)c5CCC4C23)s1]

Prepared using the general method above using the C-4 monobromide 20 as a starting material.

1H-NMR (CDCl$_3$+MeOH-d$_4$): 1.11 (s, 3H), 1.2-3.0 (m, 18H), 2.41 (s, 3H), 6.82 (d, 1H), 7.06 (s, 1H), 7.14 (d, 1H). MS m/z (TOF ES$^+$): 532/534.

Compound 64

3-{(13S,15R)-2,4-Dibromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

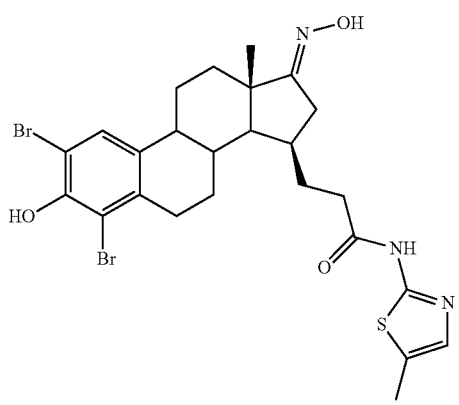 [SMILES: Cc1cnc(NC(=O)CC[C@@H]2C/C(=N\O)[C@@]3(C)CCC4c5cc(Br)c(O)c(Br)c5CCC4C23)s1]

Prepared using the general method above using the dibromide 21 as a starting material.

$^1$H-NMR (DMSO-d$_6$): 1.00 (s, 3H), 1.25-2.95 (m, 21H), 7.11 (s, 1H) 7.40 (s, 1H), 9.54 (s, 1H), 10.20 (s, 1H), 11.93 (s, 1H). MS m/z (TOF ES$^+$): 632/634/636 (M+Na).

Compound 65

3-{(13S,15R)-2-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide

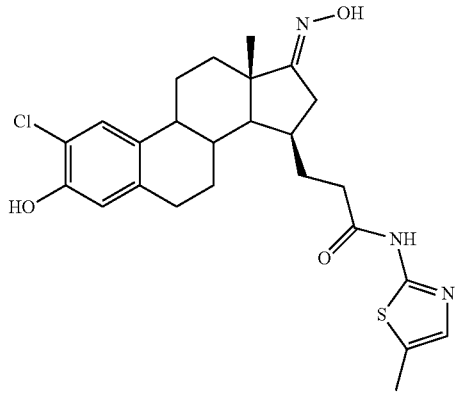 [SMILES: Cc1cnc(NC(=O)CC[C@@H]2C/C(=N\O)[C@@]3(C)CCC4c5cc(Cl)c(O)cc5CCC4C23)s1]

Prepared using the general method above using the C-2 chloride 23 as a starting material.

$^1$H-NMR (CDCl$_3$): 1.10 (s, 3H), 1.30-3.0 (m, 21H), 6.69 (s, 1H), 7.04 (s, 1H), 7.17 (s, 1H). MS m/z (TOF ES$^+$): 510/512 (M+Na).

Compound 66

3-{(13S,15R)-4-Chloro-3-hydroxy-17-[(E)-hydroxy-imino]-13-methyl-7,8,9,11,12,13,14,15,16,17-decahydro-6H-cyclopenta[a]phenanthren-15-yl}-N-(5-methylthiazol-2-yl)propanamide

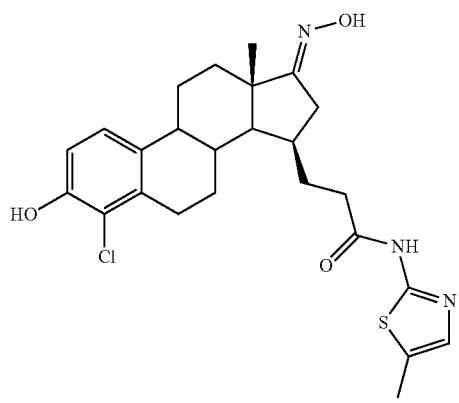 [SMILES: Cc1cnc(NC(=O)CC[C@@H]2C/C(=N\O)[C@@]3(C)CCC4c5ccc(O)c(Cl)c5CCC4C23)s1]

Prepared using the general method using the C-4 chloride 22 as a starting material.

$^1$H-NMR (CDCl$_3$): 1.10 (s, 3H), 1.30-3.05 (m, 21H), 6.80 (d, 1H), 7.05 (s, 1H), 7.08 (d, 1H). MS m/z (TOF ES$^+$): 510/512 (M+Na).

Compound 67

3-{(13S,15R)-2,4-Dichloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazo-2-yl)propanamide

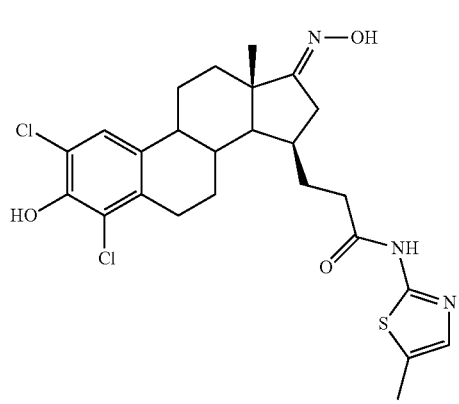 [SMILES: Cc1cnc(NC(=O)CC[C@@H]2C/C(=N\O)[C@@]3(C)CCC4c5cc(Cl)c(O)c(Cl)c5CCC4C23)s1]

Prepared using the general method above using C-2,4 dichloride 24 as a starting material.

1H-NMR (CDCl$_3$+MeOH-d$_4$): 1.11 (s, 3H), 1.4-3.0 (m, 18H), 2.39 (s, 3H), 7.03 (s, 1H), 7.19 (s, 1H). MS m/z (TOF ES$^+$): 522/524.

Compound 68

3-{(13S,15R)-2-Fluoro-3-hydroxy-17-[(E)-hydroxy-imino]-13-methyl-7,8,9,11,12,13,14,15,16,17-decahydro-6H-cyclopenta[a]phenanthren-15-yl}-N-(5-methylthiazol-2-yl)propanamide

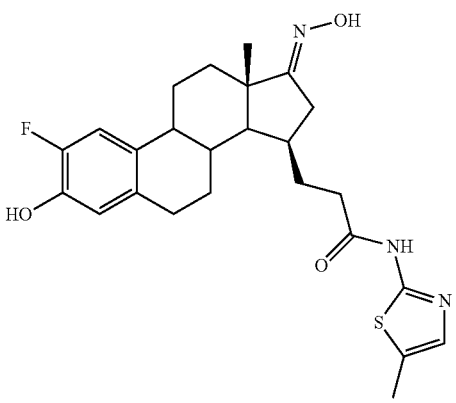 [SMILES: Cc1cnc(NC(=O)CC[C@@H]2C/C(=N\O)[C@@]3(C)CCC4c5cc(F)c(O)cc5CCC4C23)s1]

Prepared using the general method above using the C-2 fluoride 26 as a starting material.

$^1$H-NMR (CDCl$_3$+MeOH-d$_4$): 1.10 (s, 3H), 1.25-3.0 (m, 21H), 6.66 (d, J=10 Hz, 1H), 6.92 (d, J=12 Hz, 1H), 7.04 (br s, 1H). MS m/z (TOF ES$^+$): 472 (M+H).

Compound 69

3-{(13S,15S)-3-Hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide

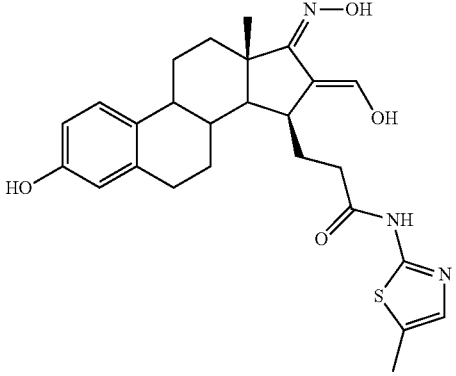 [SMILES: Cc1cnc(NC(=O)CC[C@@H]2C(=C\O)/C(=N\O)[C@@]3(C)CCC4c5ccc(O)cc5CCC4C23)s1]

Prepared using the general method above using the compound 40 as a starting material.

$^1$H-NMR (DMSO-d$_6$): 1.01 (s, 3H), 1.05-2.80 (m, 21H), 6.44 (s, 1H), 6.49 (d, 1H) 6.70 (s, 1H), 7.03 (d, 1H), 7.12 (s, 1H) 7.28 (s, 1H), 9.01 (s, 1H), 11.98 (s, 1H). MS m/z (TOF ES$^+$): 482 (M+H).

Compound 70

3-{(13S,15S)-2,4-Dibromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide

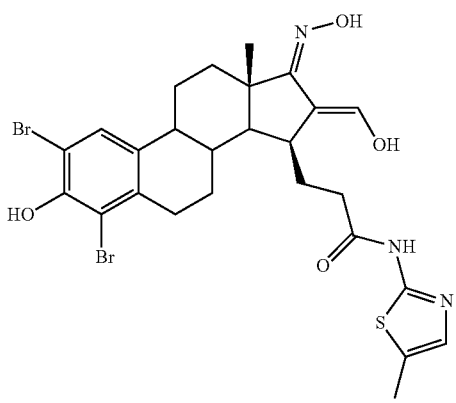 [SMILES: Cc1cnc(NC(=O)CC[C@@H]2C(=C\O)/C(=N\O)[C@@]3(C)CCC4c5cc(Br)c(O)c(Br)c5CCC4C23)s1]

Prepared using the general method above using the compound 46 as a starting material.

$^1$H-NMR (DMSO-d$_6$): 1.01 (s, 3H), 1.0-2.8 (m, 19H), 6.72 (s, 1H) 7.13 (s, 1H) 7.29 (s, 1H) 7.40 (s, 1H), 9.53 (s, 1H), 11.98 (br s, 1H). MS m/z (TOF ES$^+$): 660/662/664 (M+Na).

Compound 71

3-{(13S,15S)-4-Bromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide

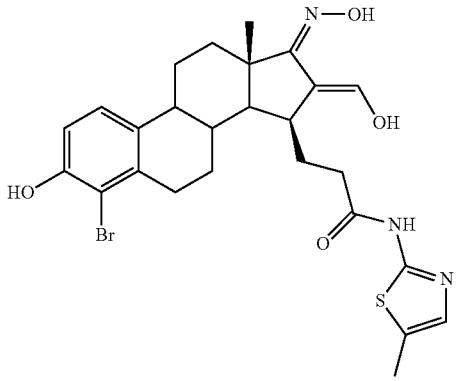 [SMILES: Cc1cnc(NC(=O)CC[C@@H]2C(=C\O)/C(=N\O)[C@@]3(C)CCC4c5ccc(O)c(Br)c5CCC4C23)s1]

Prepared using the general method above using C-4 monobromide 45 as a starting material.

1H-NMR (CDCl$_3$): 1.14 (s, 3H), 1.3-2.9 (m, 16H), 2.41 (s, 3H), 3.25 (s, 1H), 6.85 (d, 1H), 7.05 (s, 1H), 7.15 (d, 1H). MS m/z (TOF ES$^+$): 560/562.

Compound 72

3-{(13S,15R)-17-[(E)-hydroxyimino]-2-{1-[(E)-hydroxyimino]-ethyl}]-3-methoxy-13-methyl-7,8,9,11,12,13,14,15,16,17-decahydro-6H-cyclopenta[a]phenanthren-15-yl}-N-5methylthiazol-2-yl)propanamide

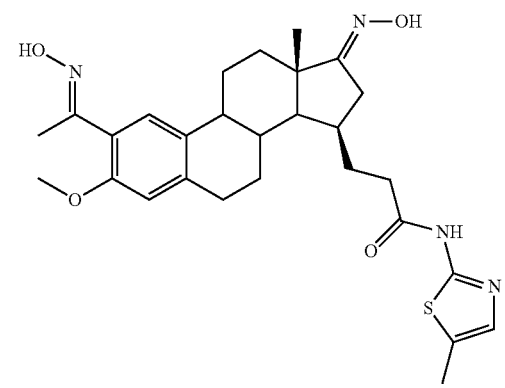 [SMILES: COc1cc2c(cc1/C(C)=N/O)C1CC[C@]3(C)/C(=N/O)C[C@@H](CCC(=O)Nc4ncc(C)s4)C3C1CC2]

Prepared using the general method above using the compound 4 as a starting material in 70% yield.

$^1$H-NMR (CDCl$_3$): 1.05 (s, 3H), 1.20-3.10 (m, 24H), 3.82 (s, 3H), 6.69 (s, 1H), 7.08 (s, 1H), 7.14 (s, 1H), 11.60 (br, 1H). MS m/z (TOF ES$^+$): 525 (M+1).

Synthesis of C-17 Methyloximes

General method for the preparation of C-17 methyl oximes: The corresponding methyl oximes were synthesized by the same method using methoxylamine instead of hydroxylamine. Carboxymethoximes 109, 110 and 111 were synthesized by the same method, but after solvent removal the reaction solution was made acidic (pH 3) with 2N HCl and the precipitated product either filtered or extracted with ethyl acetate.

Compound 73

3-{(13S,15R)-3-Hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

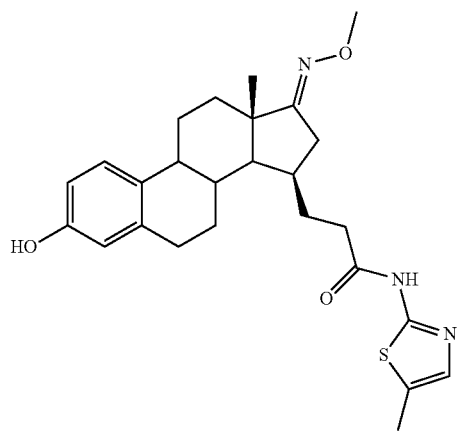 [SMILES: CO/N=C1\C[C@@H](CCC(=O)Nc2ncc(C)s2)C2C3CCc4cc(O)ccc4C3CC[C@]12C]

To a suspension of VII (700 mg, 100 mol-%) and EtOH (abs.) (30 ml) was added methoxyl amine hydrochloride (670 mg, 500 mol-%) followed by pyridine (1.52 g, 1200 mol-%). The resulting solution was refluxed 3 hours and the solvent was evaporated. Water was added to the residue. The aqueous layer was extracted with EtOAc. The combined organic layers were washed with water and brine, dried over $Na_2SO_4$, filtered and evaporated. The crude product was triturated with heptane. The yield of the product 73 was 700 mg (94%).

$^1$H-NMR (CDCl$_3$): 1.09 (s, 3H), 1.15-2.90 (m, 21H), 3.84 (s, 3H), 6.57-6.66 (m, 2H), 7.00-7.15 (m, 2H). MS m/z (TOF ES$^+$): 490 (M+Na).

Compound 74

3-{(13S,15R)-3-Methoxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

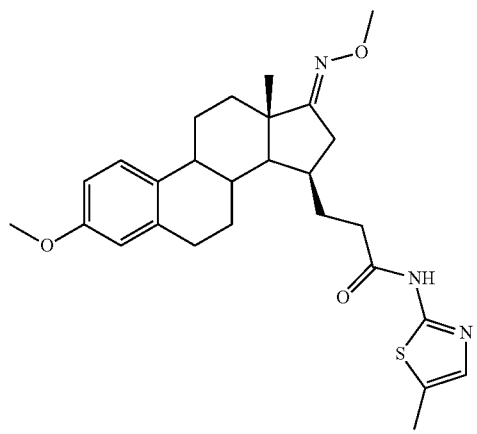 [SMILES: CO/N=C1\C[C@@H](CCC(=O)Nc2ncc(C)s2)C2C3CCc4cc(OC)ccc4C3CC[C@]12C]

Prepared by the method as described for the compound 73 using the compound 2 as a starting material.

$^1$H-NMR (CDCl$_3$): 1.10 (s, 3H), 1.20-3.00 (m, 21H), 3.78 (s, 3H), 3.84 (s, 3H), 6.63-6.74 (m, 2H), 7.07-7.22 (m, 2H). MS m/z (TOF ES$^+$): 504 (M+Na).

Compound 75

3-{(13S,15R)-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

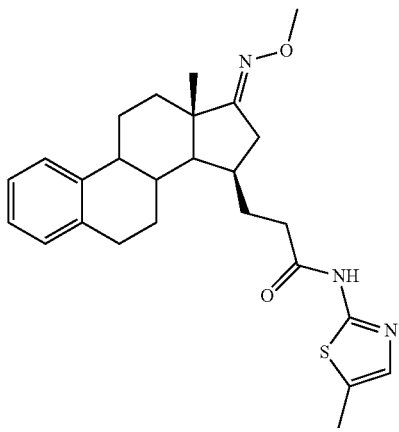 [SMILES: CO/N=C1\C[C@@H](CCC(=O)Nc2ncc(C)s2)C2C3CCc4ccccc4C3CC[C@]12C]

Prepared by the method as described for the compound 73 using the compound 37 as a starting material.

$^1$H-NMR (CDCl$_3$): 1.11 (s, 3H), 1.20-3.00 (m, 21H), 3.85 (s, 3H), 7.0-7.4 (m, 5H), 12.2 (s, 1H). MS m/z (TOF ES$^+$): 474 (M+Na).

Compound 76

3-{(13S,15R)-2-tert-Butyl-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

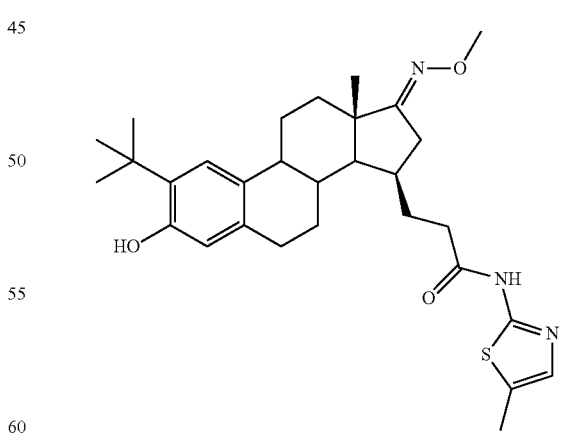

Prepared by the method as described for the compound 73 using compound 3 as a starting material in quantitative yield.

$^1$H-NMR (CDCl$_3$+MeOH-d$_4$): 1.09 (s, 3H), 1.3-2.9 (m, 33H), 3.85 (s, 3H), 6.43 (s, 1H) 7.07 (s, 1H), 7.17 (s, 1H), 12.34 (br, 1H). MS m/z (TOF ES$^+$): 546 (M+Na).

Compound 77

3-{(13S,15R)-3-Hydroxy-17-[(E)-methoxyimino]-13-methyl-2-nitro-7,8,9,11,12,13,14,15,16,17-decahydro-6H-cyclopenta[a]phenanthren-15-yl}-N-(5-methylthiazol-2-yl)propanamide

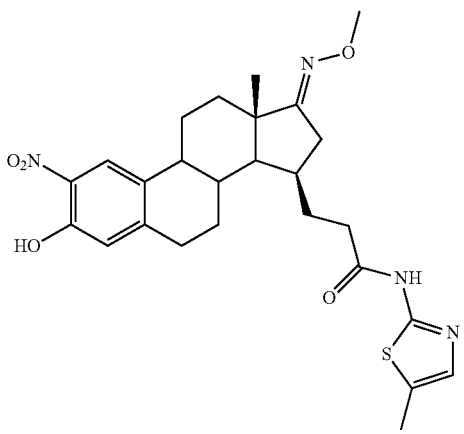 [SMILES: CO/N=C1\C[C@@H](CCC(=O)Nc2ncc(C)s2)C2C3CCc4cc(O)c(N)cc4C3CC[C@]12C]

Prepared by the method as described for the compound 73 using the compound 5 as a starting material.

$^1$H-NMR (CDCl$_3$): 1.11 (s, 3H), 1.40-3.05 (m, 21H), 3.85 (s, 3H), 6.87 (s, 1H), 7.07 (s, 1H), 7.98 (s, 1H) 10.57 (br s, 1H), 11.91 (br s, 1H). MS m/z (TOF ES$^+$): 513 (M+H).

Compound 78

3-{(13S,15R)-2-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

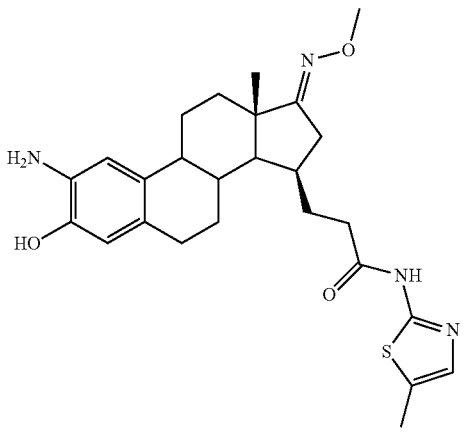

Prepared by the method as described for the compound 73 using the compound 8 as a starting material.

$^1$H-NMR (CDCl$_3$): 1.04 (s, 3H), 1.25-2.90 (m, 21H), 3.84 (s, 3H), 6.47 (s, 1H), 6.68 (s, 1H), 7.05 (s, 1H). MS m/z (TOF ES$^+$): 505 (M+Na).

Compound 79

3-{(13S,15R)-3-Hydroxy-17-[(E)-methoxyimino]-13-methyl-4-nitro-7,8,9,11,12,13,14,15,16,17-decahydro-6H-cyclopenta[a]phenanthren-15-yl}-N-(5-methylthiazol-2-yl)propanamide

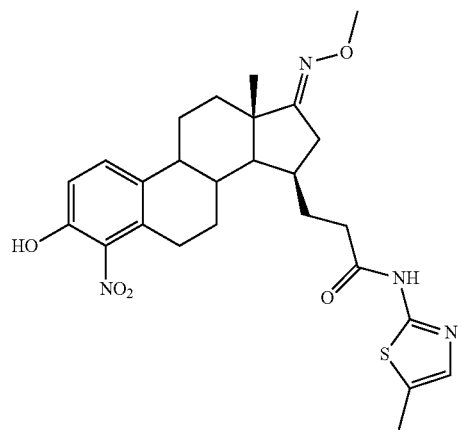 [SMILES: CO/N=C1\C[C@@H](CCC(=O)Nc2ncc(C)s2)C2C3CCc4c(ccc(O)c4[N+](=O)[O-])C3CC[C@]12C]

Prepared by the method as described for the compound 73 using the compound 6 as a starting material.

$^1$H-NMR (CDCl$_3$): 1.12 (s, 3H), 1.20-3.35 (m, 21H), 6.96 (d, 1H), 7.07 (s, 1H), 7.48 (d, 1H). MS m/z (TOF ES$^+$): 535 (M+Na).

Compound 80

3-{(13S,15R)-4-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

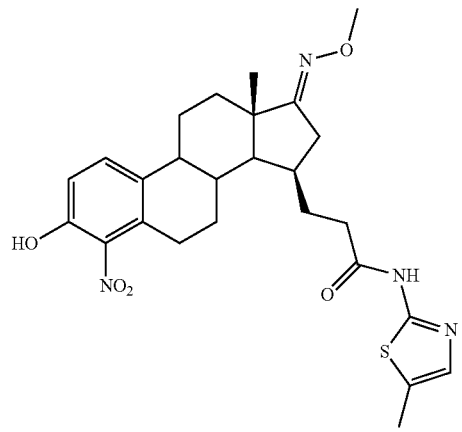 [SMILES: CO/N=C1\C[C@@H](CCC(=O)Nc2ncc(C)s2)C2C3CCc4c(ccc(O)c4[N+](=O)[O-])C3CC[C@]12C]

Prepared by the method as described for the compound 73 using the compound 9 as a starting material.

$^1$H-NMR (CDCl$_3$): 1.04 (s, 3H), 1.20-2.95 (m, 21H), 3.84 (s, 3H), 6.58 (AB, 2H), 7.08 (s, 1H). MS m/z (TOF ES$^+$): 505 (M+Na).

111

Compound 81

3-{(13S,15R)-3-Hydroxy-2-iodo-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

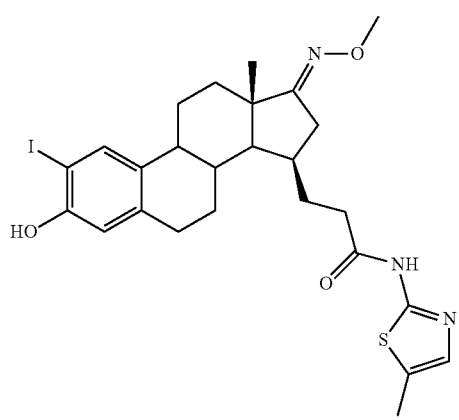 [SMILES: CO/N=C1\C[C@@H](CCC(=O)Nc2ncc(C)s2)C2C3CCc4cc(O)c(I)cc4C3CC[C@]12C]

Prepared by the method as described for the compound 73 using the compound 18 as a starting material.

$^1$H-NMR (CDCl$_3$): 1.09 (s, 3H), 1.20-2.90 (m, 21H), 3.84 (s, 3H), 6.72 (s, 1H), 7.07 (s, 1H), 7.51 (s, 1H). MS m/z (TOF ES$^+$): 616 (M+Na).

Compound 82

3-{(13S,15R)-3-Hydroxy-4-iodo-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

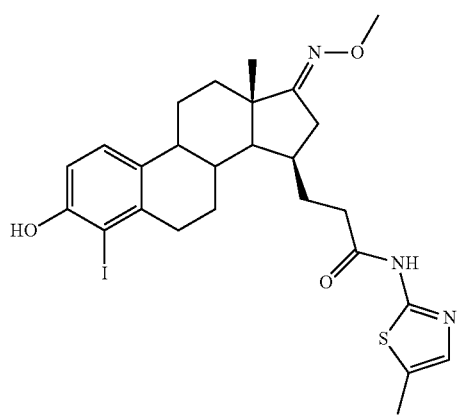 [SMILES: CO/N=C1\C[C@@H](CCC(=O)Nc2ncc(C)s2)C2C3CCc4c(ccc(O)c4I)C3CC[C@]12C]

Prepared by the method as described for the compound 73 using the compound 17 as a starting material.

$^1$H-NMR (CDCl$_3$): 1.09 (s, 3H), 1.30-2.95 (m, 21H), 3.85 (s, 3H), 6.83 (d, 1H), 7.08 (s, 1H), 7.19 (d, 1H). MS m/z (TOF ES$^+$): 616 (M+Na).

112

Compound 83

3-{(13S,15R)-3-Hydroxy-2,4-diiodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

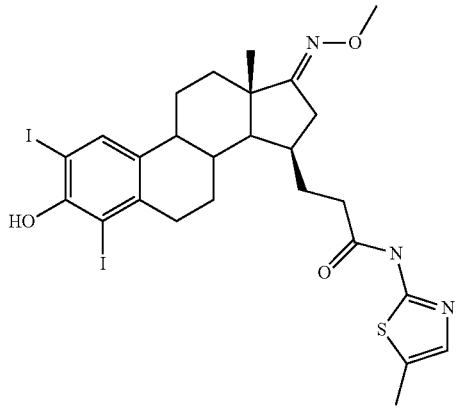 [SMILES: CO/N=C1\C[C@@H](CCC(=O)Nc2ncc(C)s2)C2C3CCc4c(cc(I)c(O)c4I)C3CC[C@]12C]

Prepared by the method as described for the compound 73 using the compound 16 as a starting material in 45% yield.

$^1$H-NMR (CDCl$_3$): 1.09 (s, 3H), 1.23-2.96 (m, 21H), 3.85 (s, 3H), 7.61 (s, 1H), 7.08 (s, 1H). MS m/z (TOF ES$^+$): 720 (M+1).

Compound 84

3-{(13S,15R)-2-iodo-3-methoxy-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

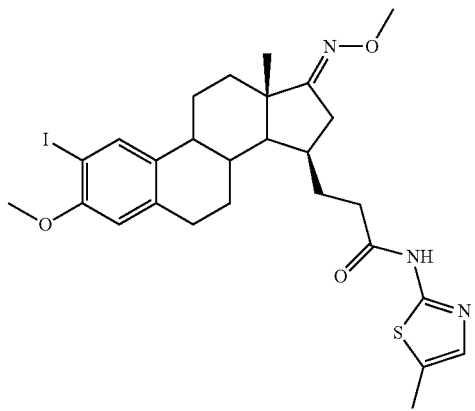 [SMILES: CO/N=C1\C[C@@H](CCC(=O)Nc2ncc(C)s2)C2C3CCc4cc(OC)c(I)cc4C3CC[C@]12C]

Prepared by the method as described for the compound 73 using the compound 15 as a starting material.

$^1$H-NMR (DMSO-d$_6$): 1.03 (s, 3H), 1.10-3.00 (m, 21H), 3.72 (s, 3H), 3.77 (s, 3H), 6.72 (s, 1H), 7.11 (s, 1H), 7.55 (s, 1H), 11.91 (s, 1H). MS m/z (TOF ES$^+$): 608 (M+1), 630 (M+Na).

Compound 85

3-{(13S,15R)-2-Bromo-3-hydroxy-17-[(E)-methoxy-imino]-13-methyl-7,8,9,11,12,13,14,15,16,17-decahydro-6H-cyclopenta[a]phenanthren-15-yl}-N-(5-methylthiazol-2-yl)-propanamide

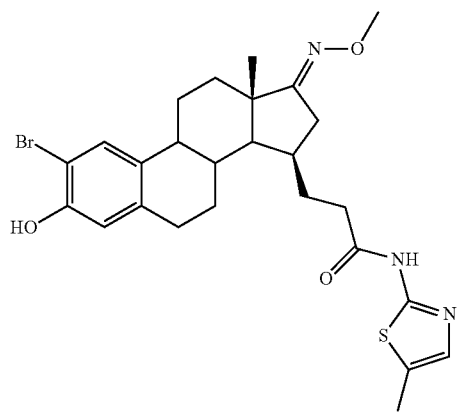

Prepared by the method as described for the compound 73 using the C-2 monobromide 19 as a starting material.

$^1$H-NMR (DMSO-d$_6$): 1.03 (s, 3H), 1.2-3.0 (m, 18H), 2.33 (s, 3H), 3.73 (s, 3H), 6.65 (s, 1H), 7.11 (s, 1H), 7.27 (d, 1H), 9.86 (s, 1H), 11.91 (s, 1H). MS m/z (TOF ES$^+$): 546/548.

Compound 86

3-{(13S,15R)-4-Bromo-3-hydroxy-17-[(E)-methoxy-imino]-13-methyl-7,8,9,11,12,13,14,15,16,17-decahydro-6H-cyclopenta[a]phenanthren-15-yl}-N-(5-methylthiazol-2-yl)propanamide

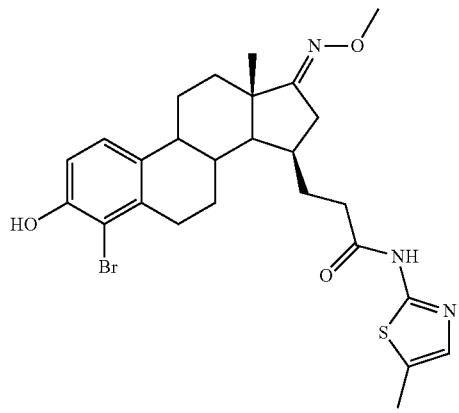 [SMILES: CO/N=C1\C[C@@H](CCC(=O)Nc2ncc(C)s2)C2C3CCc4c(ccc(O)c4Br)C3CC[C@]12C]

Prepared by the method as described for the compound 73 using the C-4 monobromide 20 as a starting material.

$^1$H-NMR (DMSO-d$_6$): 1.02 (s, 3H), 1.2-2.9 (m, 18H), 2.33 (s, 3H), 3.73 (s, 3H), 6.76 (m, 1H), 7.12 (m, 2H), 9.89 (s, 1H), 11.92 (s, 1H). MS m/z (TOF ES$^+$): 568/570 (M+Na).

Compound 87

3-{(13S,15R)-2,4-Dibromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

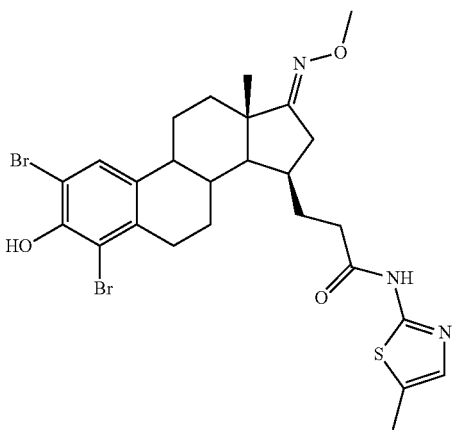 [SMILES: CO/N=C1\C[C@@H](CCC(=O)Nc2ncc(C)s2)C2C3CCc4c(cc(Br)c(O)c4Br)C3CC[C@]12C]

Prepared by the method as described for the compound 73 using the C-2,4-dibromide 21 as a starting material.

$^1$H-NMR (DMSO-d$_6$): 1.01 (s, 3H), 1.10-2.90 (m, 21H), 3.72 (s, 3H), 7.11 (s, 1H), 7.40 (s, 1H), 9.54 (s, 1H), 11.91 (s, 1H). MS m/z (TOF ES$^+$): 648 (M+Na).

Compound 88

3-{(13S,15R)-2-Chloro-3-hydroxy-17-[(E)-methoxy-imino]-13-methyl-7,8,9,11,12,13,14,15,16,17-decahydro-6H-cyclopenta[a]phenanthren-15-yl}-N-(5-methylthiazol-2-yl)propanamide

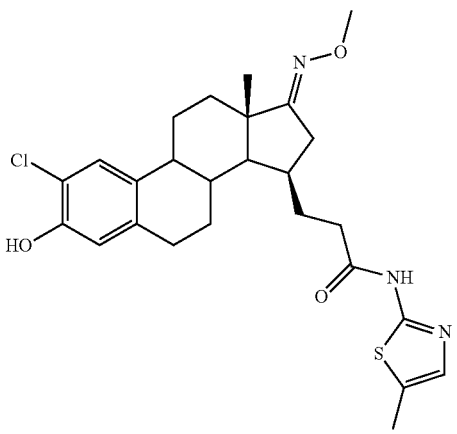 [SMILES: CO/N=C1\C[C@@H](CCC(=O)Nc2ncc(C)s2)C2C3CCc4cc(O)c(Cl)cc4C3CC[C@]12C]

Prepared by the method as described for the compound 73 using the compound 23 as a starting material.

$^1$H-NMR (CDCl$_3$): 1.09 (s, 3H), 1.25-2.92 (m, 21H), 3.84 (s, 3H), 6.73 (s, 1H), 7.07 (s, 1H), 7.19 (s, 1H). MS m/z (TOF ES$^+$): 524/526 (M+Na).

Compound 89

3-{(13S,15R)-4-Chloro-3-hydroxy-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

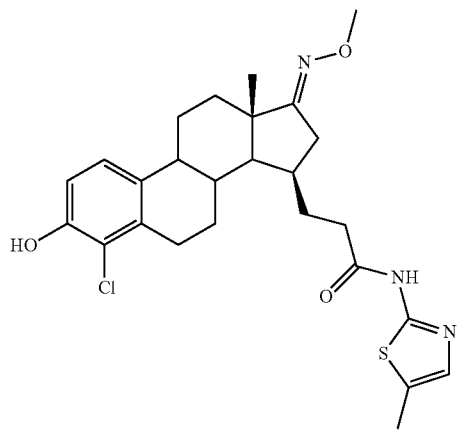

Prepared by the method as described for the compound 73 using the compound 22 as a starting material.

$^1$H-NMR (CDCl$_3$): 1.09 (s, 3H), 1.25-3.05 (m, 21H), 3.84 (s, 3H) 6.84 (d, 1H), 7.07 (s, 1H), 7.12 (d, 1H). MS m/z (TOF ES$^+$): 524/526 (M+Na).

Compound 90

3-{(13S,15R)-2,4-Dichloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

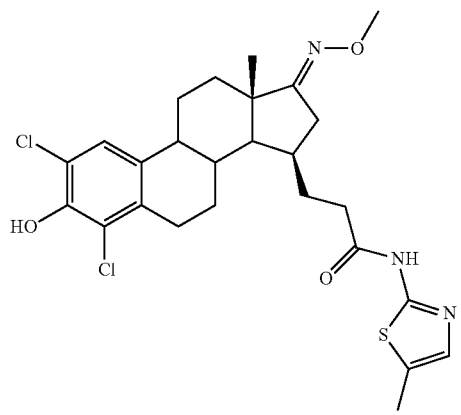 [SMILES: CO/N=C1\C[C@@H](CCC(=O)Nc2ncc(C)s2)C2C3CCc4c(cc(Cl)c(O)c4Cl)C3CC[C@]12C]

Prepared by the method as described for the compound 73 using the C-2,4 dichloride 24 as a starting material.

$^1$H-NMR (CDCl$_3$): 1.10 (s, 3H), 1.4-3.0 (m, 18H), 2.42 (s, 3H), 3.85 (s, 3H), 7.07 (s, 1H), 7.21 (s, 1H). MS m/z (TOF ES$^+$): 558/560 (M+Na).

Compound 91

3-{(13S,15R)-2-Fluoro-3-hydroxy-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

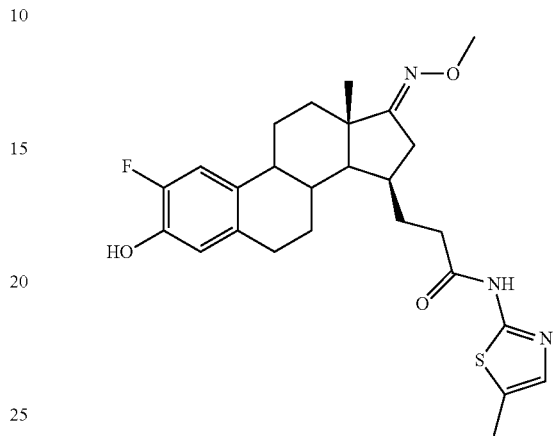

Prepared by the method as described for the compound 73 using the compound 26 as a starting material.

$^1$H-NMR (CDCl$_3$+MeOH-d$_4$): 1.10 (s, 3H), 1.25-3.0 (m, 21H), 3.84 (s, 3H), 6.66 (d, J=10 Hz, 1H), 6.94 (d, J=12 Hz, 1H), 7.03 (br s, 1H). MS m/z (TOF ES$^+$): 508 (M+Na).

Compound 92

3-{(13S,15R)-4-Fluoro-3-hydroxy-17-[(E)-methoxy-imino]-13-methyl-7,8,9,11,12,13,14,15,16,17-deca-hydro-6H-cyclopenta[a]phenanthren-15-yl}-N-(5-methylthiazol-2-yl)propanamide

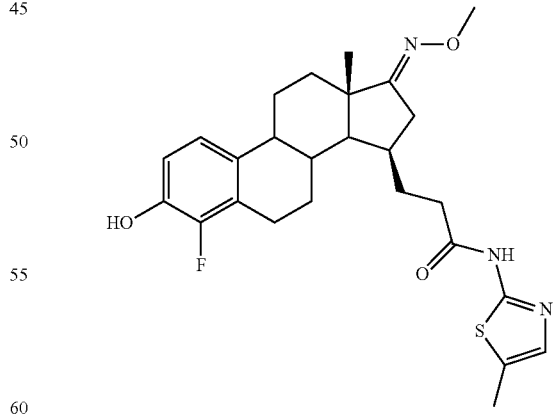

Prepared by the method as described for the compound 73 using the compound 25 as a starting material.

$^1$H-NMR (CDCl$_3$): 1.09 (s, 3H), 1.30-2.95 (m, 21H), 3.84 (s, 3H), 6.79 (t, J=4 Hz, 1H), 6.94 (d, J=4 Hz, 1H), 7.07 (br s, 1H). MS m/z (TOF ES$^+$): 508 (M+Na).

Compound 93

3-{(13S,15R)-2-Bromo-4-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

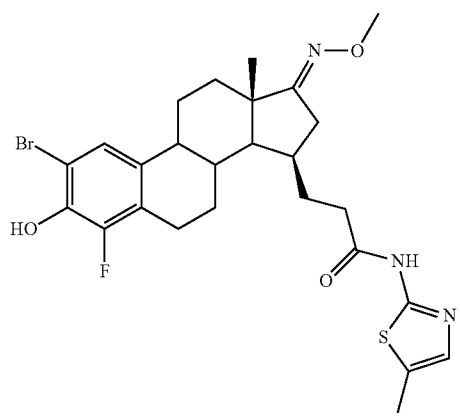 [SMILES: CO/N=C1\C[C@@H](CCC(=O)Nc2ncc(C)s2)C2C3CCc4c(cc(Br)c(O)c4F)C3CC[C@]12C]

Prepared by the method as described for the compound 73 using the compound 28 as a starting material.

$^1$H-NMR (CDCl$_3$): 1.10 (s, 3H), 1.53-2.90 (m, 21H), 3.84 (s, 3H), 7.06 (d, 1H), 7.17 (d, 1H). MS m/z (TOF ES$^+$): 564/566 (M$^+$).

Compound 94

3-{(13S,15R)-4-Bromo-2-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide

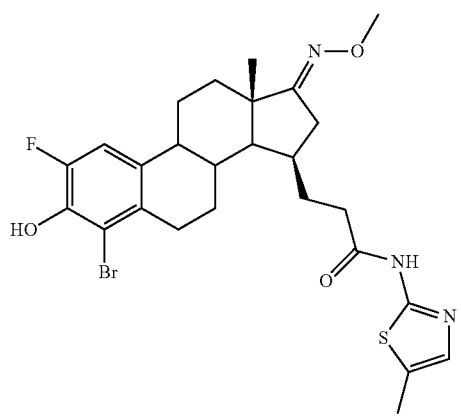 [SMILES: CO/N=C1\C[C@@H](CCC(=O)Nc2ncc(C)s2)C2C3CCc4c(cc(F)c(O)c4Br)C3CC[C@]12C]

Prepared by the method as described for the compound 73 using the compound 29 as a starting material.

$^1$H-NMR (CDCl$_3$): 1.09 (s, 3H), 1.25-2.91 (m, 21H), 3.85 (s, 3H), 7.01 (d, 1H), 7.07 (d, 1H). MS m/z (TOF ES$^+$): 564/566 (M$^+$).

Compound 95

3-{(13S,15R)-3-hydroxy-17-[(E)-methoxyimino]-13-methyl-2-nitrile-7,8,9,11,12,13,14,15,16,17-decahydro-6H-cyclopenta[a]phenanthren-15-yl}-N-(5-methylthiazol-2-yl)propanamide

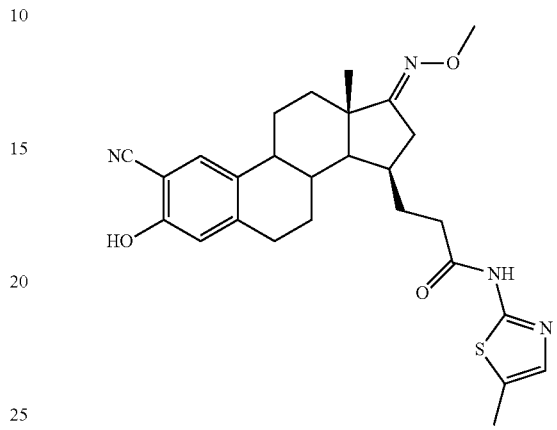

Prepared by the method as described for the compound 73 using the compound 38 as a starting material in quantitative yield.

$^1$H-NMR (CDCl$_3$): 1.09 (s, 3H), 1.2-2.43 (m, 19H), 2.87 (m, 2H), 3.85 (s, 3H), 6.70 (s, 1H), 7.37 (s, 1H). MS m/z (TOF ES$^+$): 493 (M+1).

Compound 96

3-{(13S,15R)-3-hydroxy-17-[(E)-methoxyimino]-13-methyl-4-nitrile-7,8,9,11,12,13,14,15,16,17-decahydro-6H-cyclopenta[a]phenanthren-15-yl}-N-(5-methylthiazol-2-yl)propanamide

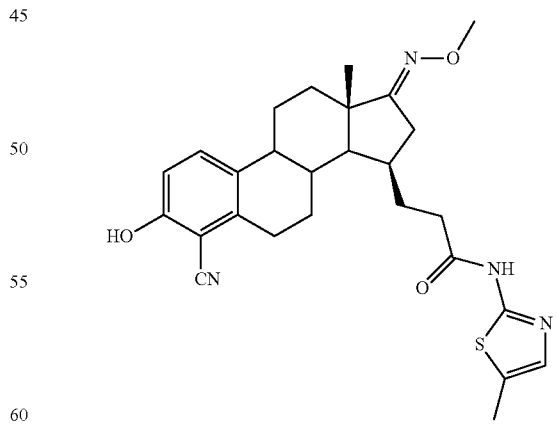

Prepared by the method as described for the compound 73 using the compound 39 as a starting material.

$^1$H-NMR (CDCl$_3$): 1.09 (s, 3H), 1.4-2.6 (m, 19H), 3.03 (m, 2H), 3.84 (s, 3H), 6.79 (d, 1H), 7.38 (d, 1H). MS m/z (TOF ES$^+$): 493 (M+1).

Compound 97

3-{(13S,15R)-3-Methoxy-17-[(E)-methoxyimino]-2-{1-[(E)-methoxyimino]-ethyl}-13-methyl-7,8,9,11,12,13,14,15,16,17-decahydro-6H-cyclopenta[a]phenanthreanthren-15-yl}-N-(5-methylthiazol-2-yl)propanamide

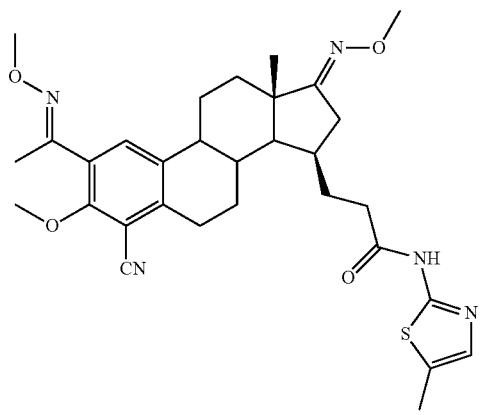 [SMILES: CO/N=C(\C)c1cc2c(c(C#N)c1OC)CCC1C2CC[C@]2(C)/C(=N/OC)C[C@@H](CCC(=O)Nc3ncc(C)s3)C12]

Prepared by the method as described for the compound 73 the compound 4 as a starting material (54% yield).

$^1$H-NMR (CDCl$_3$): 1.10 (s, 3H, H-18), 1.35-3.00 (m, 24H), 3.80 (s, 3H), 3.84 (s, 3H), 3.96 (s, 3H), 6.61 (s, 1H), 7.07 (s, 1H), 7.20 (s, 1H), 12.07 (s, 1H).

Compound 98

3-{(13S,15R)-3-Hydroxy-17-[(E)-methoxyimino]-13-methyl-2-morpholin-4-ylmethyl-7,8,9,11,12,13,14,15,16,17-decahydro-6H-cyclopenta[a]phenanthren-15-yl}-N-(5-methylthiazol-2-yl)propanamide

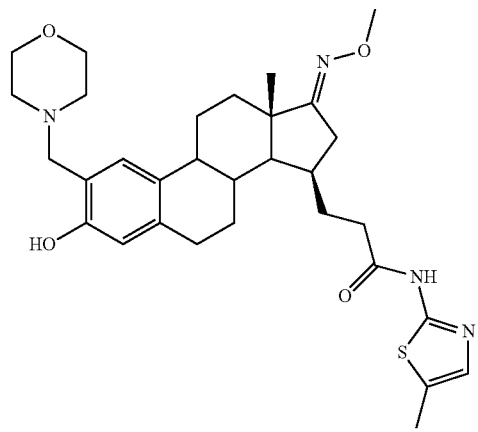 [SMILES: CO/N=C1\C[C@@H](CCC(=O)Nc2ncc(C)s2)C2C3CCc4cc(O)c(CN5CCOCC5)cc4C3CC[C@]12C]

Prepared by the method as described for the compound 73 using the compound 10 as a starting material.

$^1$H-NMR (CDCl$_3$): 1.11 (s, 3H), 1.35-2.95 (m, 21H), 3.55-3.90 (m, 6H), 6.58 (s, 1H), 6.90 (s, 1H), 7.07 (s, 1H), 11.95 (br s, 1H). MS m/z (TOF ES$^+$): 567 (M+H).

Compound 99

3-{(13S,15R)-3-Hydroxy-17-[(E)-methoxyimino]-13-methyl-2-morpholin-4-ylmethyl-4-nitro-7,8,9,11,12,13,14,15,16,17-decahydro-6H-cyclopenta[a]phenanthren-15-yl}-N-(5-methylthiazol-2-yl)propanamide

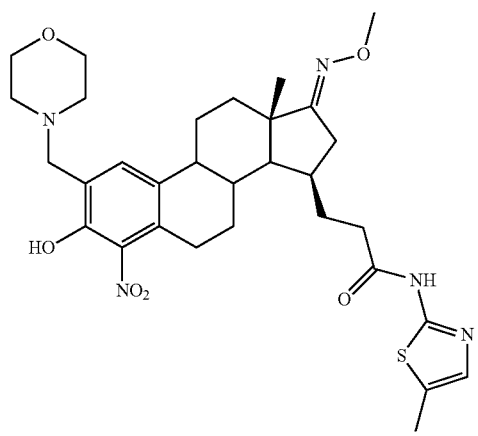 [SMILES: CO/N=C1\C[C@@H](CCC(=O)Nc2ncc(C)s2)C2C3CCc4c(cc(CN5CCOCC5)c(O)c4[N+](=O)[O-])C3CC[C@]12C]

Prepared by the method as described for the compound 73 using the compound 11 as a starting material.

$^1$H-NMR (CDCl$_3$): 1.11 (s, 3H), 1.30-2.95 (m, 21H), 3.65-3.85 (m, 6H), 3.84 (s, 3H), 7.02 (s, 1H), 7.05 (s, 1H), 11.36 (br s, 1H). MS m/z (TOF ES$^+$): 612 (M+H).

C3-Ester-C-17-Oximes

Compound 100

Acetic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester

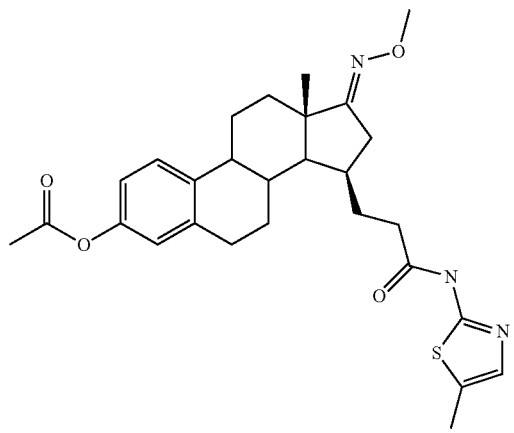 [SMILES: CO/N=C1\C[C@@H](CCC(=O)Nc2ncc(C)s2)C2C3CCc4cc(OC(C)=O)ccc4C3CC[C@]12C]

Acetylation of the Compound 73:

A mixture of intermediate 73 (290 mg, 0.62 mmol, 100 mol-%), acetic anhydride (320 mg, 3.1 mmol, 500 mol-%) and pyridine (590 mg, 7.44 mmol) in DCM (3 ml) was stirred for overnight at rt. DCM was added to reaction mixture and organic phase was washed with water, 1N HCl and water, dried over Na$_2$SO$_4$ and the solvents were removed under reduced pressure. The yield of the compound 100 was 311 mg (98%).

$^1$H-NMR (CDCl$_3$): 1.11 (s, 3H), 1.35-2.97 (m, 24H), 3.85 (s, 3H), 6.76-6.90 (m, 2H), 7.04 (s, 1H), 7.31 (s, 1H). MS m/z (TOF ES$^+$): 532 (M+Na).

Compound 101

Dimethylamino-acetic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester Compound 102

Sulphamic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester

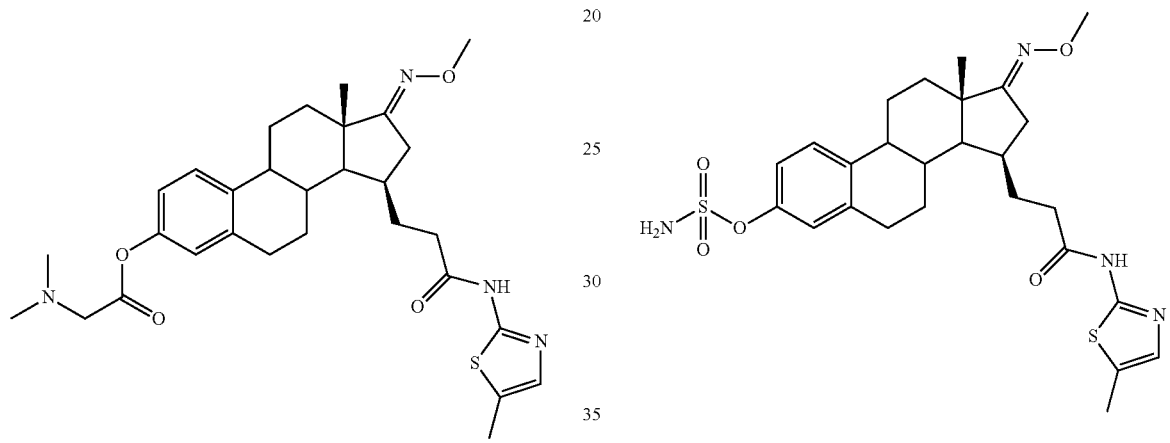

The preparation of the intermediate 101a: dimethylamino-acetic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester The compound VII (500 mg, 100 mol-%) and N,N-dimethylglycine (200 mol-%) were dissolved in dry DCM (20 ml). NMM (300 mol-%) and HOBT (170 mol-%) were added to the reaction mixture. After stirring for five minutes, the reaction mixture was cooled with ice-bath. EDCl (220 mol-%) was added. The reaction mixture was stirred overnight at rt. After dilution with DCM the reaction mixture was washed several times with 1H HCl-solution. The organic phase was washed with water and brine.

101a: $^1$H-NMR (DMSO-d$_6$): 0.98 (s, 3H), 1.40 (m), 1.6-2.4 (m), 2.31 (s, 3H), 2.39 (s, 6H), 2.87 (s, 2H), 6.86 (s, 2H), 7.11 (m, 1H), 7.30 (d, 1H), 11.92 (s, 1H). MS m/z (TOF ES$^+$): 524 (M+1).

The compound 101 was prepared using the general methyloxime-method as described for the compound 73 using dimethylglycine 101a as a starting material.

101: $^1$H-NMR (CDCl$_3$): 1.10 (s, 3H), 1.5-3.0 (m, 18H), 2.42 (s, 3H), 2.45 (s, 6H), 3.42 (s, 2H), 3.84 (s, 3H), 6.85 (m, 2H), 7.07 (s, 1H), 7.30 (s, 1H). MS m/z (TOF ES$^+$): 575 (M+Na), 553 (M+1).

The preparation of the intermediate 102a: sulphamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester The compound VII (100 mol-%) was dissolved in DCM (15 ml). Pyridine (1000 mol-%) and sulfamoyl chloride (500 mol-%) were added. The reaction was refluxed for 1-4 hours followed by TLC. DCM was added and reaction mixture washed with water, 1N HCl, water and brine. The reaction was dried with Na$_2$SO$_4$ and the solvent was evaporated. The crude product was purified by flash chromatography.

102a: $^1$H-NMR (DMSO-d$_6$): 0.97 (s, 3H), 1.30-2.40 (m, 19H), 2.86 (m, 2H), 7.00-7.37 (m, 4H), 7.92 (s, 2H), 11.92 (s, 1H). MS m/z (TOF ES$^+$): 540 (M+Na).

The compound 102 was prepared using the general methyloxime-method as described for the compound 73 using sulfamate 102a as a starting material.

$^1$H-NMR (CDCl$_3$): 1.10 (s, 3H), 1.3-2.8 (m, 18H), 2.39 (s, 3H), 3.85 (s, 3H), 6.97 (m, 3H), 7.17 (m, 1H). MS m/z (TOF ES$^+$): 569 (M+Na).

123

Compound 103

Dimethyl-sulfamic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester

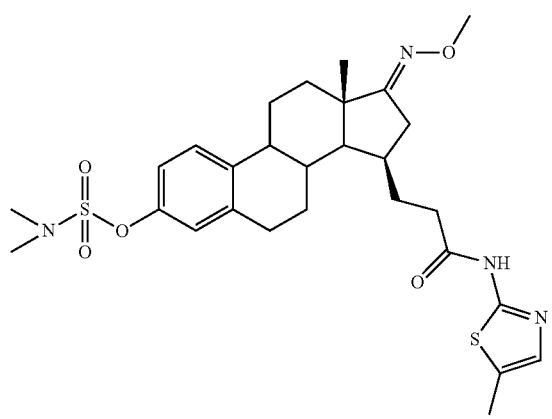 [SMILES: CO/N=C1\C[C@@H](CCC(=O)Nc2ncc(C)s2)C2C3CCc4cc(OS(=O)(=O)N(C)C)ccc4C3CC[C@]12C]

The preparation of the intermediate 103a: Dimethyl-sulphamic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester 103a: N,N-dimethylsulfamoyl chloride (300 mol-%) was added to the mixture of the compound VII (100 mg, 100 mol-%) and TEA (300 mol-%) in dry DCM at 0° C. Stirred at rt for two days, concentrated and purified by chromatography using DMC:EtOAc as an eluent (gradient from 100:0 to 75:25).

$^1$H-NMR (DMSO-d$_6$): 0.98 (s, 3H), 1.41 (m), 1.6-2.4 (m), 2.33 (s, 3H), 2.91 (s, 6H), 7.04 (s, 1H), 7.11 (m, 2H), 7.36 (d, 1H), 11.92 (s, 1H). MS m/z (TOF ES$^+$): 546 (M+1).

The compound 103 was prepared using the general methyloxime-method as described for the compound 73 using sulfamate 103a as a starting material. The yield was 94%.

103: $^1$H-NMR (CDCl$_3$): 1.11 (s, 3H), 1.3-1.85 (m, 7H), 1.9-2.55 (m, 10H), 2.55-2.91 (m, 4H), 2.98 (s, 6H), 3.84 (s, 3H), 6.95-7.1 (m, 3H), 7.3 (s, 1H), 12.26 (s, 1H). MS m/z (TOF ES$^+$): 597 (M+Na).

124

Compound 104

Methanesulphonic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester

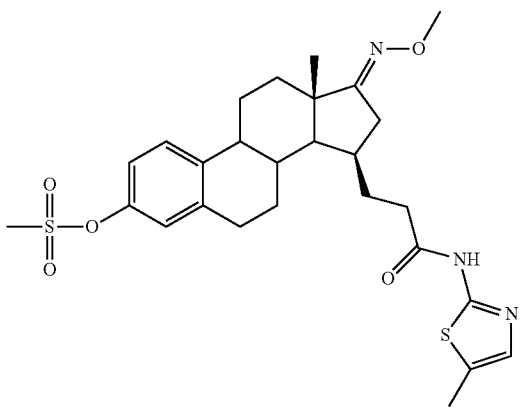 [SMILES: CO/N=C1\C[C@@H](CCC(=O)Nc2ncc(C)s2)C2C3CCc4cc(OS(C)(=O)=O)ccc4C3CC[C@]12C]

The preparation of the intermediate 104a: Methanesulphonic acid (13S,15R)-13-methyl-15-[2-(5-methylthiazol-2-ylcarbamoyl)-ethyl]-17-oxo-7,8,9,11,12,13,14,15,16,17-decahydro-6H-cyclopenta[a]phenanthren-3-yl ester The intermediate 104a was prepared according to the method described for the compound 103a starting from the compound VII using mesyl chloride as a reagent in 65% yield.

104a: $^1$H-NMR (DMSO-d$_6$): 0.97 (s, 3H), 1.36-2.40 (m, 22H), 2.91 (m, 2H), 6.82-6.86 (m, 2H), 7.09 (s+d, 3H), 7.37 (d, 1H), 11.91 (s, 1H). MS m/z (TOF ES$^+$): 539 (M+Na), 517 (M+1).

The compound 104 was prepared using the general methyloxime-method as described for the compound 73 using 104a as a starting material.

104: $^1$H-NMR (CDCl$_3$): 1.11 (s, 3H), 1.20-3.00 (m, 21H), 3.13 (s, 3H), 3.85 (s, 3H), 7.02-7.07 (m, 2H), 7.26-7.33 (m, 2H). MS m/z (TOF ES$^+$): 568 (M+Na).

Other Oxime Derivatives

Compound 105

3-{(13S,15R)-17-[(E)-Ethoxyimino]-3-hydroxy-13-methyl-7,8,9,11,12,13,14,15,16,17-decahydro-6H-cyclopenta[a]phenanthren-15-yl}-N-(5-methylthiazol-2-yl)propanamide

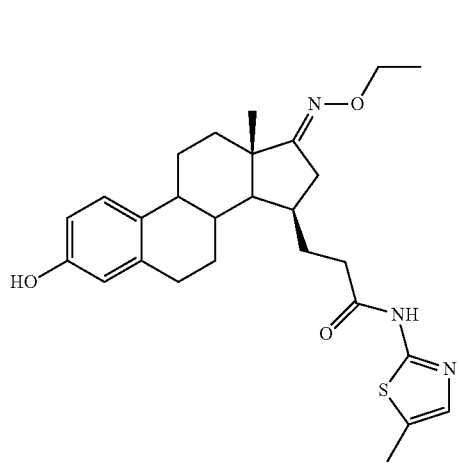 [SMILES: CCO/N=C1\C[C@@H](CCC(=O)Nc2ncc(C)s2)C2C3CCc4cc(O)ccc4C3CC[C@]12C]

Prepared by the method as described for the compound 73 using the compound VII as a starting material and ethyl hydroxylamine hydrochloride as a reagent, yield 82%.

$^1$H-NMR (DMSO-$d_6$): 1.03 (s, 3H), 1.17 (t, 3H), 1.2-2.9 (m, 18H), 2.33 (s, 3H), 3.98 (q, 2H), 6.50 (m, 2H), 7.04 (d, 1H), 7.11 (s, 1H), 9.04 (s, 1H), 11.91 (s, 1H). MS m/z (TOF ES$^+$): 504 (M+Na), 482 (M+1).

Compound 106

3-{(13S,15R)-2-tert-Butyl-17-[(E)-ethoxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide

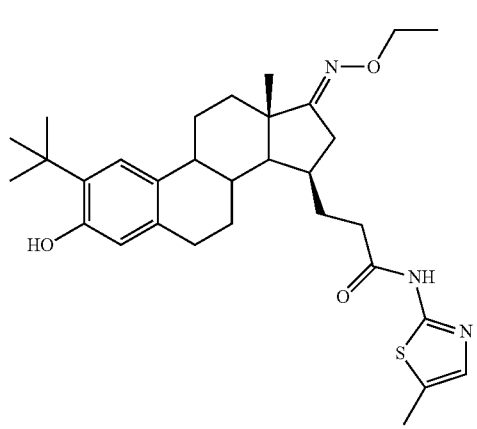 [SMILES: CCO/N=C1\C[C@@H](CCC(=O)Nc2ncc(C)s2)C2C3CCc4cc(O)c(C(C)(C)C)cc4C3CC[C@]12C]

Prepared by the method as described for the compound 73 using the compound 3 as a starting material and ethyl hydroxylamine hydrochloride as a reagent, yield 87%.

$^1$H-NMR (DMSO-$d_6$): 1.03 (s, 3H), 1.17 (t, 3H), 1.31 (s, 9H), 1.2-2.8 (m, 18H), 2.33 (s, 3H), 3.99 (q, 2H), 6.46 (s, 1H), 7.00 (s, 1H), 7.11 (s, 1H), 8.97 (s, 1H), 11.91 (s, 1H). MS m/z (TOF ES$^+$): 560 (M+Na), 538 (M+1).

Compound 107

3-{(13S,15R)-17-[(E)-Allyloxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide

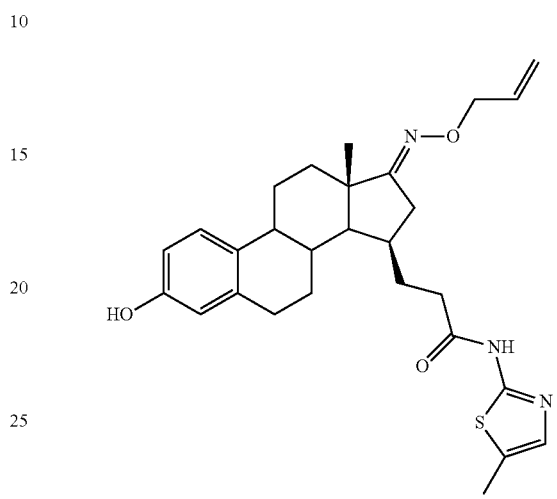

Prepared by the method as described for the compound 73 using the compound VII as a starting material and o-allylhydroxylamine hydrochloride as a reagent.

$^1$H-NMR (CDCl$_3$): 1.10 (s, 3H), 1.40-3.00 (m, 21H), 4.55 (d, 2H), 5.10-5.35 (m, 2H), 5.90-6.10 (m, 1H), 6.58 (s, 1H), 6.63 (d, 1H), 7.08 (s, 1H), 7.13 (d, 1H). MS m/z (TOF ES$^+$): 516 (M+Na).

Compound 108

3-{(13S,15R)-17-[(E)-Allyloxyimino]-3-hydroxyl-13-methyl-2-nitro-7,8,9,11,12,13,14,15,16,17-decahydro-6H-cyclopenta[a]phenanthren-15-yl}-N-(5-methylthiazol-2-yl)propanamide

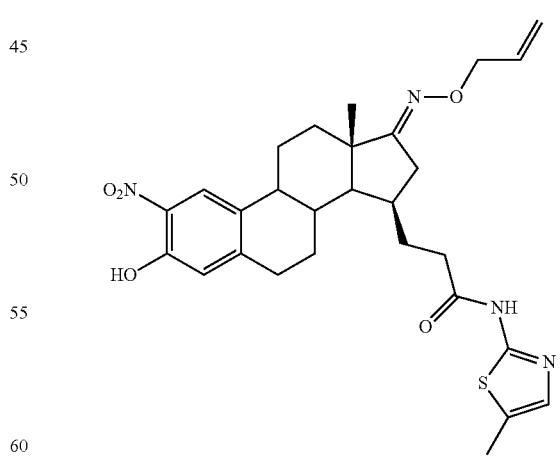

Prepared by the method as described for the compound 73 using the compound 5 as a starting material and o-allylhydroxylamine hydrochloride as a reagent.

$^1$H-NMR (CDCl$_3$): 1.12 (s, 3H), 1.35-3.00 (m, 21H), 4.56 (d, 2H), 5.10-5.35 (m, 2H), 5.90-6.10 (m, 1H), 6.86 (s, 1H), 7.07 (s, 1H), 7.97 (s, 1H). MS m/z (TOF ES$^+$): 539 (M+H).

The carboxymethoximes 109, 110 and 111 were synthesized by the general method, but after solvent removal the reaction solution was made acidic (pH 3) with 2N HCl and the precipitated product either filtered or extracted with ethyl acetate.

Compound 109

[(13S,15R)-3-Hydroxy-13-methyl-15-[2-(5-methyl-thiazol-2-ylcarbamoyl)-ethyl]-6,7,8,9,11,12,13,14,15,16-decahydro-cyclopenta[a]phenanthren-(17E)-ylideneaminooxy]-acetic acid

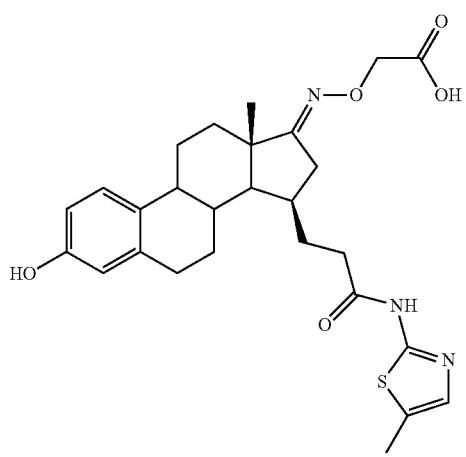 [SMILES: Cc1cnc(NC(=O)CC[C@@H]2C/C(=N\OCC(=O)O)[C@@]3(C)CCC4c5ccc(O)cc5CCC4C23)s1]

Prepared by the method as described for the compound 73 using the compound VII as a starting material and o-carboxymethylhydroxylamine×0.5 HCl as a reagent.

$^1$H-NMR (DMSO-d$_6$): 1.03 (s, 3H), 1.20-3.0 (m, 21H), 4.47 (br s, 2H), 6.47 (m, 2H), 7.04 (d, 1H), 7.11 (s, 1H), 9.04 (s, 1H), 11.93 (s, 1H). MS m/z (TOF ES$^+$): 534 (M+Na).

Compound 110

[(13S,15R)-2-tert-Butyl-3-hydroxy-13-methyl-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid

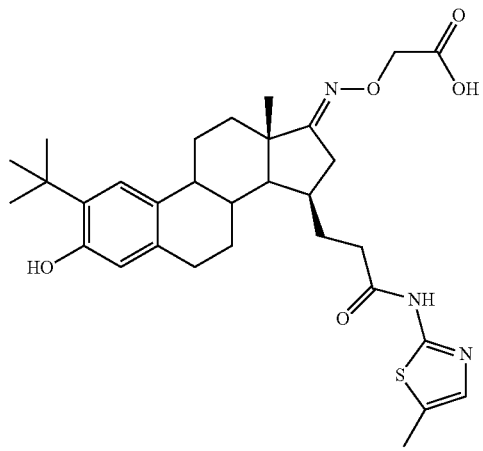 [SMILES: Cc1cnc(NC(=O)CC[C@@H]2C/C(=N\OCC(=O)O)[C@@]3(C)CCC4c5cc(C(C)(C)C)c(O)cc5CCC4C23)s1]

Prepared by the method as described for the compound 73 using the compound 3 as a starting material and o-carboxymethylhydroxylamine×0.5 HCl as a reagent.

$^1$H-NMR (CDCl$_3$+MeOH-d$_4$): 1.12 (s, 3H), 1.30-3.15 (m, 30H), 4.66 (s, 2H), 6.44 (s, 1H) 7.01 (s, 1H), 7.15 (s, 1H). MS m/z (TOF ES$^+$): 568 (M+H).

Compound 111

[(13S,15R)-3-Hydroxy-13-methyl-2-nitro-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid

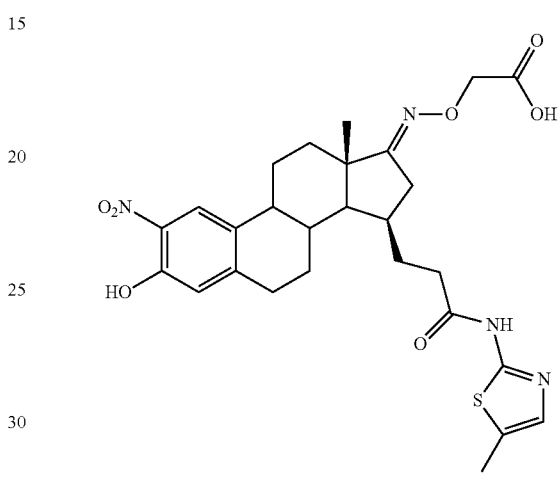

Prepared by the method as described for the compound 73 using the compound 5 as a starting material and o-carboxymethylhydroxylamine×0.5 HCl as the reagent.

$^1$H-NMR (CDCl$_3$+MeOH-d$_4$): 1.09 (s, 3H), 1.35-3.10 (m, 21H), 4.61 (s, 2H), 6.87 (s, 1H), 7.01 (s, 1H), 7.94 (s, 1H). MS m/z (TOF ES$^+$): 557 (M+H).

Compound 112

3-{(13S,15R)-3-Hydroxy-17-[(E)-N-urea-imino]-13-methyl-7,8,9,11,12,13,14,15,16,17-decahydro-6H-cyclopenta[a]phenanthren-15-yl}-N-(5-methylthiazol-2-yl)propanamide

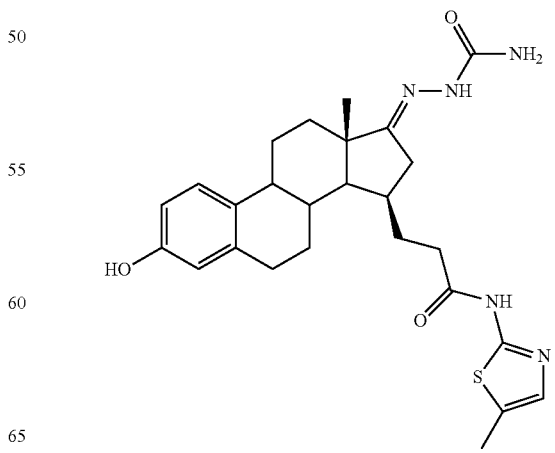

The compound VII (0.2 mmol) was dissolved in a solution of ethanol/THF (v/v 3 ml/1 ml) and warmed at 70° C. for 4 hours. Semicarbazide hydrochloride (0.4 mmol) and sodium acetate (0.5 mmol) were added. Stirring was continued for 1 hour. The solvents were evaporated. Water was added and the reaction mixture was stirred at rt. The produced precipitate was filtered, washed with water and heptane. The yield of the semicarbazone 112 was quantitative.

$^1$H-NMR (DMSO-$d_6$): 0.99 (s, 3H), 1.20-2.90 (m, 21H), 2.33 (s, 3H), 6.15 (br s, 2H), 6.46 (s, 1H), 6.50 (d, 1H), 7.05 (d, 1H), 7.11 (s, 1H), 8.73 (s, 1H), 9.02 (s, 1H), 11.94 (br s, 1H). MS m/z (TOF ES$^+$): 518 (M+Na).

Compound 113

3-{(13S,15R)-2,4-Dibromo-3-hydroxy-17-[(E)-N-urea-imino]-13-methyl-7,8,9,11,12,13,14,15,16,17-decahydro-6H-cyclopenta[a]phenanthren-15-yl}-N-(5-methylthiazol-2-yl)propanamide

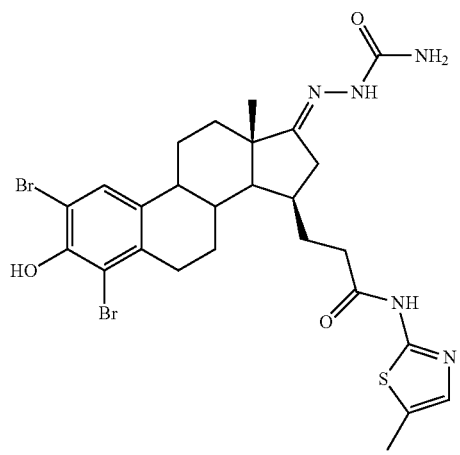 [SMILES: Cc1cnc(NC(=O)CC[C@@H]2C/C(=N\NC(N)=O)[C@@]3(C)CCC4c5cc(Br)c(O)c(Br)c5CCC4C23)s1]

Prepared by the same method as used for the compound 112 using the compound 21 as a starting material.

$^1$H-NMR (DMSO-$d_6$): 0.97 (s, 3H), 1.20-2.95 (m, 21H), 2.33 (s, 3H), 6.16 (s, 2H), 7.11 (s, 1H), 7.41 (s, 1H), 8.74 (s, 1H), 9.49 (s, 1H), 11.94 (br s, 1H). MS m/z (TOF ES$^+$): 674/676/678 (M+Na).

Heterocyclic R2, R3 and R3, R4 Oximes and Methyl Oximes

Compound 114

3-{(7aS,1OR)-8-[(E)-Hydroxyimino]-7a-methyl-6,7,7a,8,9,10,10a,10b,11,12-decahydro-5bH-3-oxa-1-aza-dicyclopenta[a,i]phenathenn-10-yl}-N-(5-methylthiazol-2-yl)propanamide

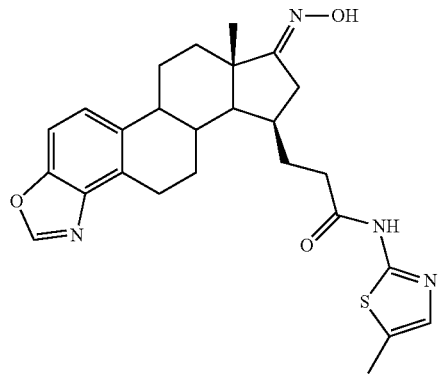 [SMILES: Cc1cnc(NC(=O)CC[C@@H]2C/C(=N\O)[C@@]3(C)CCC4c5ccc6ocnc6c5CCC4C23)s1]

Prepared by the general oxime preparation method with hydroxylamine hydrochloride as a reagent using the compound 12 as a starting material.

$^1$H-NMR (CDCl$_3$+MeOH-$d_4$): 1.15 (s, 3H), 1.45-3.35 (m, 21H), 7.03 (s, 1H), 7.37 (s, 2H), 8.09 (s, 1H). MS m/z (TOF ES$^+$): 501 (M+Na).

Compound 115

3-{(7aS,10R)-8-[(E)-Methoxyimino]-7a-methyl-6,7,7a,8,9,10,10a,10b,11,12-decahydro-5bH-3-oxa-1-aza-dicyclopenta[a,i]phenathren-10-yl}-N-(5-methylthiazol-2-yl)propanamide

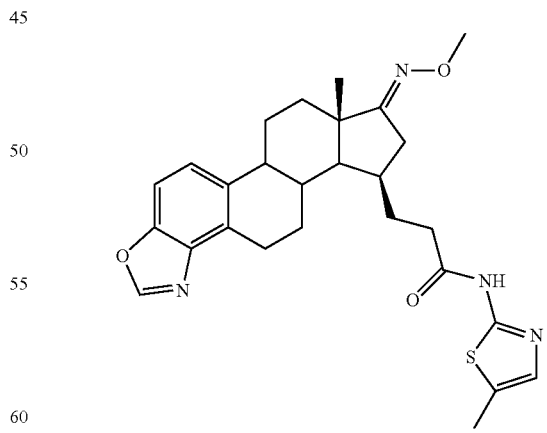

Prepared by the general method described for the compound 73 using the compound 12 as a starting material.

$^1$H-NMR (CDCl$_3$): 1.13 (s, 3H), 1.40-3.45 (m, 21H), 3.85 (s, 3H), 7.08 (s, 1H), 7.36 (s, 2H), 8.05 (s, 1H), 12.26 (br s, 1H). MS m/z (TOF ES$^+$): 515 (M+Na).

Compound 116

3-{(3R,12aS)-1-[(E)-Methoxyimino]-1a-methyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide

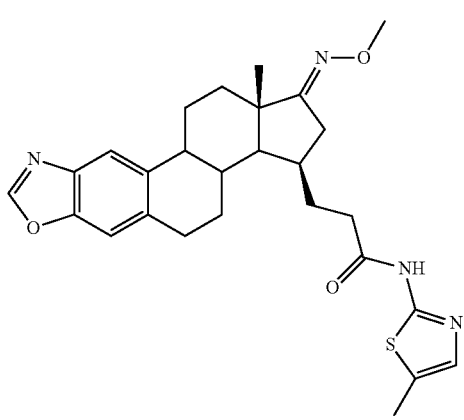 [SMILES: CO/N=C1\C[C@@H](CCC(=O)Nc2ncc(C)s2)C2C3CCc4cc5ocnc5cc4C3CC[C@]12C]

Prepared by the method as described for the compound 73 using the compound 13 as a starting material.

$^1$H-NMR (CDCl$_3$): 1.12 (s, 3H), 1.40-3.10 (m, 21H), 3.85 (s, 3H), 7.06 (s, 1H), 7.30 (s, 1H), 7.70 (s, 1H), 8.01 (s, 1H), 12.36 (br s, 1H). MS m/z (TOF ES$^+$): 515 (M+Na).

Compound 117

3-{(3R,12aS)-6-Chloro-1-[(E)-methoxyimino]-12a-methyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide

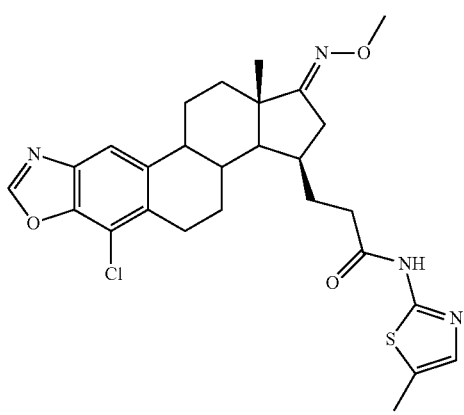 [SMILES: CO/N=C1\C[C@@H](CCC(=O)Nc2ncc(C)s2)C2C3CCc4c(cc5ncoc5c4Cl)C3CC[C@]12C]

Prepared by the method as described for the compound 73 using the compound 34 as a starting material.

$^1$H-NMR (CDCl$_3$): 1.11 (s, 3H), 1.40-3.20 (m, 21H), 3.85 (s, 3H), 7.08 (s, 1H), 7.66 (s, 1H), 8.05 (s, 1H), 12.00 (br s, 1H). MS m/z (TOF ES+): 527/529 (M+H).

Compound 118

3-{(3R,12aS)-1-[(E)-Methoxyimino]-8,12a-dimethyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide

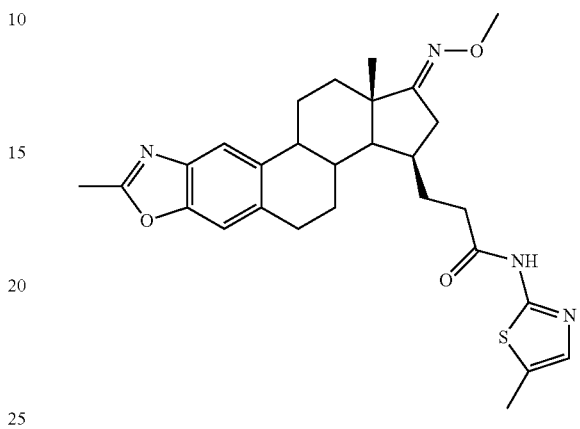

Prepared by the method as described for the compound 73 using the compound 14 as a starting material.

$^1$H-NMR (CDCl$_3$): 1.11 (s, 3H), 1.40-3.10 (m, 21H), 2.60 (s, 3H), 3.85 (s, 3H), 7.07 (s, 1H), 7.17 (s, 1H), 7.55 (s, 1H), 12.36 (br s, 1H). MS m/z (TOF ES$^+$): 507 (M+H).

Isoxazoles

Compound 119

3-((6aS,10S)-1,3-Dibromo-2-hydroxy-6a-methyl-4-nitro-4b,6,6a,10,10a,10b,11,12-octahydro-5H-8-oxa-7-aza-pentaleno[2,1-a]phenanthren-10-yl}-N-(5-methylthiazol-2-yl)propanamide

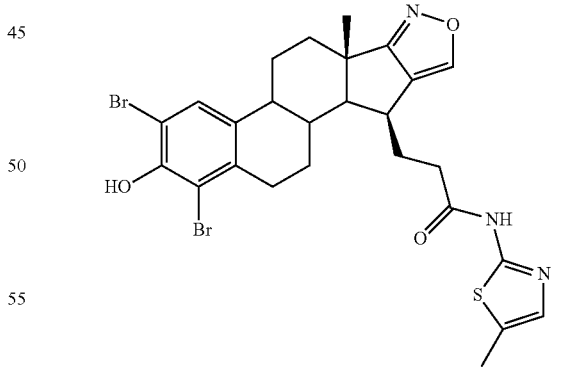

1 ml of Eaton's reagent (7.7% w/w phosphorus pentoxide in methanesulfonic acid) was added into 90 mg of the compound 70 under nitrogen and stirred for 2.5 h at rt. Reaction mixture was poured into ice water and neutralized with 2N NaOH. Product was extracted with ethyl acetate, washed twice with water and once with brine, dried with sodium sulfate and solvent evaporated. The residue was triturated with DCM giving 10 mg of isoxazole 119.

¹H-NMR (CDCl₃+MeOH-d₄): 1.27 (s, 3H), 1.40-3.05 (m, 19H), 7.03 (s, 1H), 7.38 (s, 1H), 8.18 (s, 1H). MS m/z (TOF ES⁺): 620/622/624 (M+H).

Compound 120

Methanesulphonic acid (6aS,10S)-6a-methyl-10-[2-(5-methylthiazol-2-ylcarbamoyl)-ethyl]-4b,6,6a,10,10a,10b,11,12-octahydro-5H-8-oxa-7-aza-pentaleno[2,1-a]phenanthren-2-yl ester

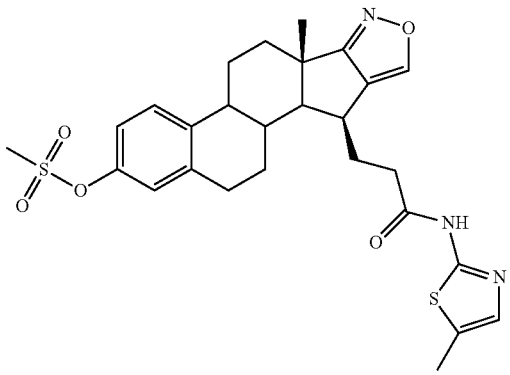 [SMILES: Cc1cnc(NC(=O)CC[C@@H]2c3conc3[C@@]3(C)CCC4c5ccc(OS(C)(=O)=O)cc5CCC4C23)s1]

The compound 120 was isolated as a main product prepared from the compound 69 by the same method as used for the compound 119.

¹H-NMR (CDCl₃): 1.26 (s, 3H), 1.40-3.10 (m, 19H), 3.15 (s, 3H), 7.01 (s, 1H), 7.04 s, 1H) 7.06 (d, 1H), 7.30 (d, 1H), 8.07 (s, 1H). MS m/z (TOF ES⁺): 564 (M+Na).

Compound 121

3-{(13S,15R)-3-Hydroxy-17-[(E)-isobutylimino]-13-methyl-7,8,9,11,12,13,14,15,16,17-decahydro-6H-cyclopenta[a]phenanthren-15-yl}-N-(5-methylthiazol-2-yl)propionamide

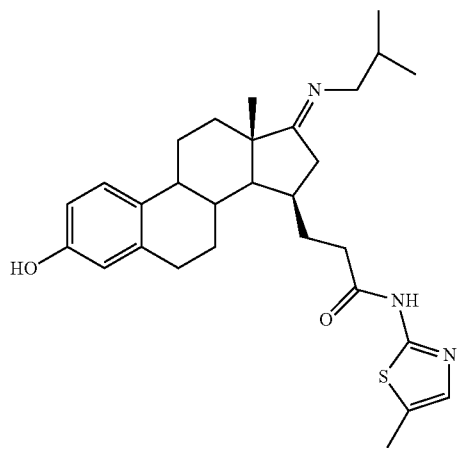 [SMILES: Cc1cnc(NC(=O)CC[C@@H]2C/C(=N\CC(C)C)[C@@]3(C)CCC4c5ccc(O)cc5CCC4C23)s1]

The compound VII (50 mg, 0.11 mmol, 100 mol-%) was dissolved in THF (2 ml) and DCM (2 ml) under nitrogen atmosphere. Isobutylamine (120 μl, 1.36 mmol, 1200 mol-%), Zn (45 mg, 0.68 mmol, 600 mol-%) and acetic acid (40 μl, 0.68 mmol, 600 mol-%) were added. Molecular sieves (4 Å) were added. Reaction was refluxed for 6.5 hours and stirred at rt overnight. Reaction was poured in to ice-water (10 ml) and pH adjusted to pH=8-9 with 2N NaOH. Ethyl acetate (10 ml) was added and mixture was filtered through celite. Reaction was extracted with EtOAc (3×5 ml). Combined organic layers were washed with water (3×10 ml) and brine (1×10 ml) and dried with Na₂SO₄. Crude product was triturated with heptane. Amount of the compound 121 was 15.6 mg.

¹H NMR (200 MHz, CDCl₃) δ ppm 0.77-1.07 (m, 6H), 1.05 (s, 3H), 1.43 (s, 3H), 1.5-2.9 (m, 21H), 3.07 (d, 2H), 6.54-6.7 (m, 2H), 7.07 (br, 2H).

The Compound 122

3-{(13S,15R)-3-Hydroxy-17-[(E)-2-methoxy-ethylimino]-13-methyl-7,8,9,11,12,13,14,15,16,17-decahydro-6H-cyclopenta[a]phenanthren-15-yl}-N-(5-methylthiazol-2-yl)propionamide

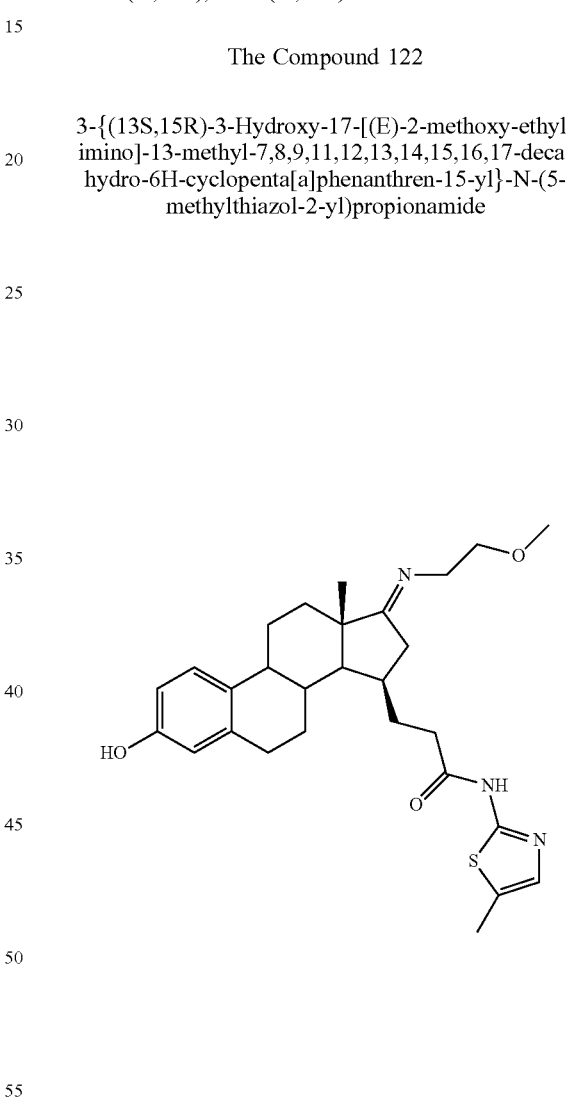

The synthesis of the compound 122 was done from the compound VII (100 mg) by the same method used for the compound 121 using 2-methoxyethylamine (1200 mol-%) as reagent. Reaction refluxed for several days affording 40 mg of the compound 122.

¹H NMR (200 MHz, CDCl₃) δ ppm 0.99 (s, 3H), 1.43-1.69 (m, 6H), 2.00-2.88 (m, 16H), 3.35 (d, 3H), 3.40 (m, 2H), 3.64 (m, 2H), 6.54-6.61 (m, 2H), 6.98 (m, 1H), 7.07 (br, 1H).

The Compound 123

3-{(13S,15R)-2-tert-Butyl-3-hydroxy-17-[(E)-2-methoxy-ethylimino]-13-methyl-7,8,9,11,12,13,14,15,16,17-decahydro-6H-cyclopenta[a]phenanthren-15-yl}-N-(5-methylthiazol-2-yl)propionamide

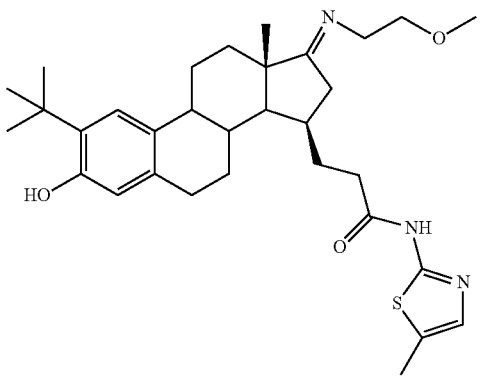 [SMILES: COCC/N=C1\C[C@@H](CCC(=O)Nc2ncc(C)s2)C2C3CCc4cc(O)c(C(C)(C)C)cc4C3CC[C@]12C]

The synthesis of the compound 123 was done by the same method as for the compound 121 using 2-methoxyethylamine (600 mol-%) as reagent and the compound 3 as a starting material. Reaction was refluxed for 10 hours and stirred overnight at rt.

$^1$H NMR (200 MHz, CDCl$_3$) δ ppm 1.04 (s, 3H), 1.39-1.85 (m, 16H), 1.89-2.75 (m, 15H), 3.35 (s, 3H), 3.45 (m, 2H), 3.65 (m, 2H), 6.45 (m, 1H), 7.07 (br s, 1H), 7.16 (br s, 1H).

Compound 124

3-((13S,15R,E)-2-(tert-butyl)-3-hydroxy-4-iodo-17-(methoxyimino)-13-methyl-7,8,9,11,12,13,14,15,16,17-decahydro-6H-cyclopenta[a]phenanthren-15-yl)-N-(5-methylthiazol-2-yl)propanamide

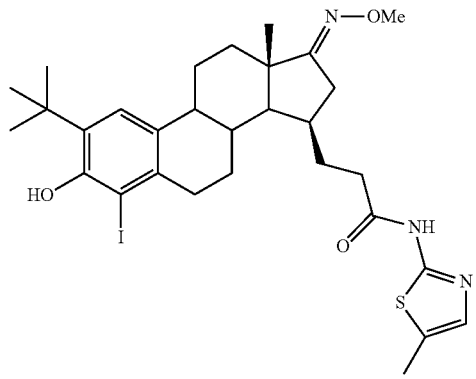 [SMILES: CO/N=C1\C[C@@H](CCC(=O)Nc2ncc(C)s2)C2C3CCc4c(cc(C(C)(C)C)c(O)c4I)C3CC[C@]12C]

The compound 76 (100 mg, 0.191 mmol, 100 mol-%) and p-TsOH (33 mg, 100 mol-%) were dissolved in dry ACN (2 ml) and stirred for 15 min at rt. N-iodosuccinimide (52 mg, 0.229 mmol, 120 mol-%) was added in portions. Reaction was stirred at rt for 2.5 hours and additional amount of N-iodosuccinimide (24 mol-%) was added. Stirring was continued overnight at rt. Water was added (5 ml) and 10% Na$_2$CO$_3$ was added until pH 8. Product was extracted in EtOAc (3×10 ml). Combined organic layers were washed with 10% Na$_2$SO$_3$, water and brine and dried with Na$_2$SO$_4$. Solvent was evaporated. Crude product (123 mg) was purified with flash chromatography. The amount of the compound 124 was 80 mg.

$^1$H-NMR (DMSO-d$_6$): 1.02 (s, 3H), 1.33 (s, 9H), 1.20-2.80 (m, 21H), 3.73 (s, 3H), 7.11 (s, 1H), 7.14 (s, 1H), 7.97 (s, 1H), 11.90 (br s, 1H).

Pharmacological Tests

The following tests are provided to demonstrate the present invention in illustrative way and should not be considered as limiting in the scope of invention. Further, the concentrations of the compound in the assays are exemplary and should not be taken as limiting. A person skilled in the art may define pharmaceutically relevant concentrations with method known in the art.

Inhibition of 17-Hydroxysteroid Dehydrogenase Type 1 Enzyme

17β-HSD1 Production and Isolation:

Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested; the microsomal fraction was isolated as described by Puranen, T. J., Poutanen, M. H., Peltoketo, H. E., Vihko, P. T. and Vihko, R. K. (1994) Site-directed mutagenesis of the putative active site of human 17 β-hydroxysteroid dehydrogenase type 1. Biochem. J. 304: 289-293. Aliquots were stored frozen until determination of enzymatic activity.

Assay—Inhibition of Recombinant Human 17β-HSD1:

Recombinant protein (1 μg/ml) was incubated in 20 mM KH2PO4 pH 7.4 with 30 nM estrone (including 800 000 cpm/ml of $^3$H-estrone) and 1 mM NADPH for 30 min at RT, in the presence of the potential inhibitor at concentrations 1 μM or 0.1 μM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estrone to estradiol was calculated according to the following formula:

$$\% \text{ conversion} = 100 \times \frac{\{(cpm \text{ estradiol in sample with inhibitor})/[(cpm \text{ estrone in sample with inhibitor}) + (cpm \text{ estradiol in sample with inhibitor})]\}}{[(cpm \text{ estradiol in sample without inhibitor})/[(cpm \text{ estrone in sample without inhibitor}) + (cpm \text{ estradiol in sample without inhibitor})]\}}$$

Percent inhibition was calculated flowingly: % inhibition=100−% conversion

The values % inhibition were determined for exemplified compounds and the results are summarized in Table 2.

Inhibition of the 17β-Hydroxysteroid Dehydrogenase Type 2 Enzyme

17β-HSD2 Production and Isolation:

Similarly to 17β-HSD1 the Recombinant baculovirus was generated by the "Bac to Bac Expression System" (Invitrogen). Recombinant bacmid was transfected to Sd9 insect cells using "Cellfectin Reagent" (Invitrogen). 60 h later cells were harvested and supernatant were fractionated by the following protocol:

cells were dissolved into 40 ml of A-buffer (40 mM TRIS, pH8.0, 20% glycerol, 2 µM NAD, 0.4 mM PMSF, 150 mM NaCl, 0.5% dodecyl-3-maltoside+protease inhibitor cocktail)

cells were sonicated lysate was incubated on ice for 15 min lysate was centrifuged 5000 rpm 15 min, +4° C.

centrifugation of the supernatant 180 000 g 30 min, +4° C.

pellet was dissolved into 8 ml of A-buffer not resuspended material was removed by centrifugation 5000 rpm 15 min, +4° C.

the clear supernatant was divided into 100 µl aliquots and were stored frozen until determination of enzymatic activity.

The amount of 17β-HSD2 was analysed by immunoblotting and total protein concentration of each extract batch was determined.

Assay—Inhibition of Recombinant Human 17β-HSD2:

Recombinant protein (4 µg/ml) was incubated in 20 mM KH2PO4 pH 8.5 with 50 nM estradiol (including 800 000 cpm/ml of $^3$H-estradiol) and 1 mM NADH for 30 min at RT, in the presence of the potential inhibitor at concentrations 1 µM or 0.1 µM. Inhibitor stock solutions were prepared in DMSO. Final concentration of DMSO was adjusted to 1% in all samples. The enzyme reaction was stopped by addition of 10% trichloroacetic acid (final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min in acetonitrile:water 48:52 as running solvent. Radioactivity was monitored in the eluate by a Packard Flow Scintillation Analyzer. Total radioactivity for estrone and estradiol were determined in each sample and percent conversion of estradiol to estrone was calculated according to the following formula:

$$\% \text{ conversion} = 100 \times \frac{\{(cpm \text{ estrone in sample with inhibitor})/[(cpm \text{ estradiol in sample with inhibitor}) + (cpm \text{ estrone in sample with inhibitor})]\}}{[(cpm \text{ estrone in sample without inhibitor})/[(cpm \text{ estradiol in sample without inhibitor}) + (cpm \text{ estrone in sample without inhibitor})]\}}$$

Percent inhibition was calculated flowingly: % inhibition=100−% conversion

The values % inhibition were determined for exemplified compounds and the results are summarized in Table 2.

Estrogen Receptor Binding Assay

The binding affinity of the compounds of the invention to the estrogen receptor a (ERα) may be determined according to the in vitro ER binding assay described by Koffmann et al REF. Alternatively, an estrogen receptor binding assay may be performed according to international patent application WO2000/07996.

Estrogen Receptor Transactivation Assays

Compound of the invention showing binding affinity towards the estrogen receptor may be further tested with regard to their individual estrogenic or anti-estrogenic potential (Agonistic or antagonistic binding to the ERα or ERβ). The determination of the estrogen receptor antagonistic activity may be performed according to an in vitro assay system using the MMTV-ERE-LUC reporter system for example described in US patent application US2003/0170292.

Metabolic Stability Assay

The in vitro metabolic stability of the compounds of the invention was determined for exemplified compounds using human liver microsome and homogenate incubations. The incubation time points used with or without appropriate cofactors were 0 min and 60 min. Samples were collected at both time points and substrates were detected using LC/PDA/TOF-MS. In vitro metabolic stability (% remaining after 60 min in human liver homogenate or microsomes) of the compounds were calculated and the results are summarized in Table 3.

Pharmacological Test Results

TABLE 2

| # | 17β-HDS1 Inhibition % at 1 µM | 17β-HSD2 Inhibition % at 1 µM |
|---|---|---|
| 50 | 78 | 0 |
| 51 | 82 | 15 |
| 52 | 94 | 0 |
| 53 | 76 | 13 |
| 54 | 90 | 13 |
| 55 | 69 | 7 |
| 56 | 97 | 39 |
| 57 | 81 | 4 |
| 58 | 95 | 41 |
| 59 | 93 | 2 |
| 60 | 95 | 6 |
| 61 | 96 | 33 |
| 62 | 77 | 25 |
| 63 | 89 | 15 |
| 64 | 98 | 28 |
| 65 | 98 | 21 |
| 66 | 98 | 21 |
| 67 | 87 | 23 |
| 68 | 97 | 14 |
| 69 | 98 | 2 |
| 70 | 94 | 8 |
| 71 | 82 | 7 |
| 72 | 77 | 3 |
| 73 | 95 | 4 |
| 74 | 59 | 2 |
| 76 | 86 | 14 |
| 77 | 64 | 3 |
| 79 | 90 | 16 |
| 81 | 90 | 0 |
| 82 | 81 | 0 |
| 83 | 61 | 2 |
| 84 | 62 | 1 |
| 85 | 81 | 1 |
| 86 | 78 | 6 |
| 87 | 78 | 3 |
| 88 | 95 | 3 |
| 89 | 86 | 5 |
| 91 | 94 | 5 |
| 92 | 90 | 7 |
| 93 | 83 | 2 |
| 94 | 55 | 1 |
| 95 | 93 | 2 |
| 96 | 73 | 0 |
| 98 | 57 | 0 |
| 100 | 84 | 1 |
| 101 | 88 | 3 |
| 105 | 94 | 3 |
| 106 | 89 | 8 |
| 107 | 70 | 3 |
| 108 | 80 | 1 |
| 109 | 56 | 0 |
| 110 | 70 | 7 |
| 111 | 55 | 0 |

TABLE 2-continued

| # | 17β-HDS1 Inhibition % at 1 μM | 17β-HSD2 Inhibition % at 1 μM |
|---|---|---|
| 112 | 83 | 5 |
| 113 | 58 | 1 |
| 114 | 70 | 5 |
| 119 | 79 | 28 |
| 121 | 94 | 7 |
| 122 | 94 | 5 |
| 123 | 94 | 30 |

TABLE 3

| # | In vitro metabolic stability, % remaining after 60 min |
|---|---|
| VII | 13 |
| 50 | 88 |
| 51 | 46 |
| 53 | 100 |
| 55 | 86 |
| 58 | 100 |
| 59 | 100 |
| 60 | 84 |
| 63 | 64 |
| 64 | 95 |
| 70 | 97 |
| 73 | 73 |
| 76 | 100 |
| 85 | 34 |
| 88 | 94 |
| 91 | 92 |
| 92 | 68 |

Utility of the Invention

Compounds of the invention show selective inhibitory potential of the 17β-HSD1 enzyme and little or no inhibitory activity to the 17β-HSD2 enzyme and therefor, and may be useful for the treatment of a steroid hormone dependent malign or benign disease or disorder, in particular for treatment and prevention of several estrogen dependent diseases and disorders. Further, compounds of the present invention may be useful for the treatment of diseases and disorders associated with increased levels of estradiol and which may be prevented, treated, and/or ameliorated by an inhibitor of 17β-HSD1 enzyme.

Examples of inflammatory diseases and conditions include, but are not limited to, breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

"Treatment or prevention" as used herein includes prophylaxis, or prevention of, as well as lowering the individual's risk of falling ill with the named disorder or condition, or alleviation, amelioration, elimination, or cure of the said disorder once it has been established.

Compounds of the present invention may be administered in an effective amount within the dosage range of about 0.1 μg/kg to about 300 mg/kg, preferably between 1.0 μg/kg to 10 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the invention are most preferably used alone or in combination i.e. administered simultaneously, separately or sequentially with other active ingredients. Compounds of the invention may be administered by various routes, for example, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant.

Compounds may be formulated into a suitable composition; suitable administration forms include, for example, solutions, dispersions, suspensions, powders, capsules, tablet, pills, controlled release capsules, controlled release tablets and controlled release pills. In addition to the pharmacologically active compounds, the pharmaceutical compositions of the compounds can contain suitable pharmaceutically acceptable carriers comprising excipients and auxiliaries that facilitate processing of the active compounds into preparations that can be used pharmaceutically.

Furthermore, compounds of formula (I) can be used as synthesis intermediates for the preparation of other compounds, in particular of other pharmaceutically active ingredients, which are obtainable from compounds of formula (I), for example by introduction of substituents or modification of functional groups.

It will be obvious to a person skilled in the art that, as the technology advances, the inventive concept can be implemented in various ways. The invention and its embodiments are not limited to the examples described above but may vary within the scope of the claims.

The invention claimed is:
1. A compound of formula (I)

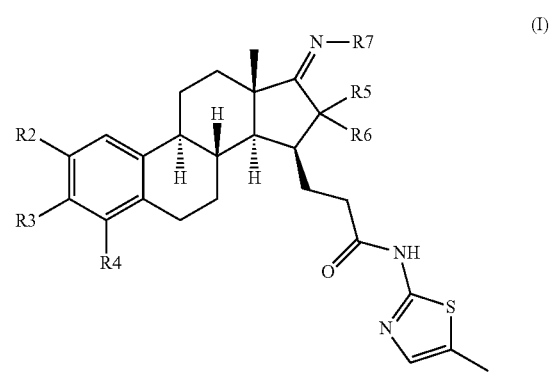

wherein
(i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_n N(R')_2$, OR', $(CH_2)_n OR'$, $CO_2R'$, CONHR', NHCOR", C(=NH)R", C(=N—OH)R" and COR";

R3 is selected from the group consisting of H, $C_{1-6}$-alkyl, $C_{1-3}$-haloalkyl, $C_{1-3}$-perhaloalkyl, $N(R')_2$, $N_3$, and $OR_3'$, wherein $R_3'$ is selected from the group consisting of R', benzyl, succinyl, optionally acylated glucuronyl, $(CH_2)_nOH$, $SO_2OH$, $SO_2R''$, tosyl, $SO_2N(R')_2$, $PO(OR')_2$, $COOR'''$, $C(O)N(R')_2$, $C(O)(CH_2)_nN(R')_2$, $C(O)CH_2NHC(O)R'$, $C(O)CH_2NHC(O)OR''$ and $C(O)R'''$;

wherein

R' is H or $C_{1-6}$-alkyl, $C_{1-3}$-haloalkyl, or $C_{1-3}$-perhaloalkyl, or when part of any $N(R')_2$ both R's together with the nitrogen they are attached to may form an 5 to 6 membered aliphatic or aromatic heterocyclic ring comprising 1 or 2 heteroatoms each independently selected from N and O;

R" is $C_{1-6}$-alkyl, $C_{1-3}$-haloalkyl, or $C_{1-3}$-perhaloalkyl;

R''' is $C_{1-18}$-alkyl, $C_{2-18}$-alkenyl, $-(CH_2)_n-C_{3-6}$-cycloalkyl, or optionally substituted phenyl; and n is 1 or 2; or (i-b) R2 and R3 or R3 and R4, together with the ring carbon atoms to which they are attached, form an unsaturated or aromatic 5-membered heterocyclic ring comprising 1 or 2 heteroatoms each independently selected from N and O, optionally substituted with methyl or oxo; and R4 or R2, respectively, is H and halogen;

(ii-a) R5 and R6 are each H or R5 and R6 form together =CH—OH; and

R7 is selected from the group consisting of ureido, R'O—$C_{1-3}$-alkylenyl, R'S—$C_{1-3}$-alkylenyl, R'$_2$N—$C_{1-3}$-alkylenyl, and OR7', wherein R7' is selected from the group consisting of H, $C_{1-6}$-alkyl, $C_{3-6}$-alkenyl, and carboxy-$C_{1-3}$-alkylenyl; or (ii-b) R5 and R6 and =NR7 form together with the carbons they are attached to a structure

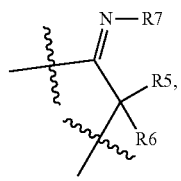

which is selected from

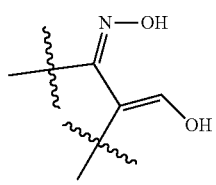 and 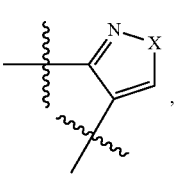

wherein X is O or NH;

or a pharmaceutically acceptable salt thereof.

2. A compound as claimed in claim 1, having formula (Ia)

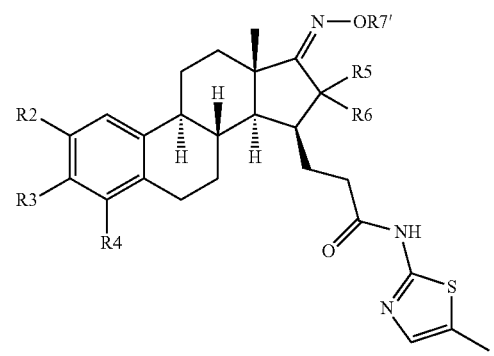

(Ia)

wherein R2, R3, R4, R5, R6 and R7' are as defined in claim 1.

3. A compound as claimed in claim 2, wherein R7' is selected from the group consisting of H, methyl, ethyl, allyl, and carboxymethylenyl.

4. A compound as claimed in claim 1, wherein R5 and R6 are both H.

5. A compound of claimed in claim 1 having formula (Ib)

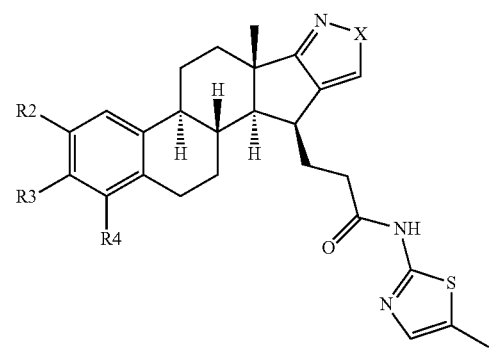

(Ib)

wherein

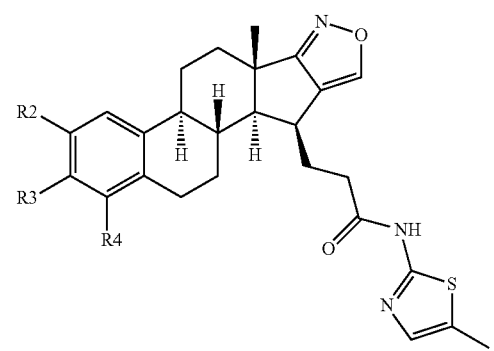

(Ic)

X is NH or O, and R2, R3 and R4 are as defined in claim 1.

6. A compound as claimed in claim 5 having formula (Ic) wherein R2, R3 and R4 are as defined in claim 1.

7. A compound as claimed in claim 5 having formula (Id)

(Id)

wherein R2, R3 and R4 are as defined in claim 1.

8. A compound as claimed in claim 1, wherein (i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_n (R')_2$, $C(=N-OH)R''$, and $C(=N-OMe)R''$.

9. A compound as claimed in claim 1, wherein

R3 is selected from a group consisting of H, $C_{1-6}$-alkyl, $C_{1-3}$-perhaloalkyl, $N(R')_2$, $N_3$, and OR'.

10. A compound as claimed in claim 9, wherein R3 is H or OR'.

11. A compound as claimed in claim 1, wherein R2 and R3 or R3 and R4, together with the ring carbon atoms to which they are attached, form an oxazolone or 1,3-oxazole ring, optionally substituted with methyl.

12. A compound as claimed in claim 11, wherein R4 or R2, respectively, is selected from the group consisting of H, F, Cl, Br, and I.

13. A compound as claimed in claim 1, wherein (i-a) R2 and R4 are each independently selected from the group consisting of H, halogen, $C_{1-6}$-alkyl, $C_{1-3}$-haloalkyl, $C_{1-3}$-perhaloalkyl, CN, $NO_2$, $N_3$, $N(R')_2$, $(CH_2)_n(R')_2$, $C(=N-OH)R''$, and $C(=N-OMe)R''$; and R3 is selected from a group consisting of H, $C_{1-6}$-alkyl, $C_{1-3}$-perhaloalkyl, $N(R')_2$, $N_3$, and OR';

wherein n, R' and R" are as defined in claim 1; or (i-b) R2 and R3 or R3 and R4, together with the ring carbon atoms to which they are attached, form an oxazolone or 1,3-oxazole ring, optionally substituted with methyl; and R4 or R2, respectively, is selected from the group consisting of H, F, Cl, Br, and I.

14. A compound as claimed in claim 1, having the formula (Ie)

(Ie)

wherein R2, R5 to R7 are as defined in claim 1, and R is H or methyl.

15. A compound as claimed in claim 14, wherein R4 is selected from the group consisting of H, F, Cl, Br, and I.

16. A compound as claimed in claim 1, having the formula (If)

(If)

wherein R4 to R7 are as defined in claim 1, and R is H or methyl.

17. The compound as claimed in claim 16, wherein R4 is selected from the group consisting of H, F, Cl, Br, and I.

18. The compound as claimed in claim 1 selected from the group consisting of:

Compound 50 3-((6aS,10S)-2-Methoxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 51 3-((6aS,10S)-2-Hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 52 3-((6aS,10S)-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 53 3-((6aS,10S)-3-tert-Butyl-2-hydroxy-6a-methyl-4b,5,6,6a,8,10,10a,10b,11,12-decehydro-7,8-diaza-pentaleno[2,1-1]phenanthren-10-yl}-N-(5-methylthiazol-2-yl)propanamide;

Compound 54 3-((6aS,10S)-1,3-dibromo-2-hydroxy-6a-methyl-4b,5,6,6a,8,10,10a,10b,11,12-decehydro-7,8- diaza-pentaleno[2,1-1]phenanthren-10-yl}-N-(5-methylthiazol-2-yl)propanamide;

Compound 55 3-((6aS,10S)-2-Hydroxy-6a-methyl-2-nitro-4b,5,6,6a,8,10,10a,10b, 11,12-decehydro-7,8-diaza-pentaleno[2,1-1]phenanthren-10-yl}-N-(5-methylthiazol-2-yl)propanamide;

Compound 56 3-((6aS,10S)-2-Hydroxy-6a-methyl-4-nitro-4b,5,6,6a,8,10,10a,10b,11,12-decehydro-7,8-diazapentaleno[2,1-1]phenanthren-10-yl}-N-(5-methylthiazol-2-yl)propanamide;

Compound 57 3-{(13S,15R)-3-Hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 58 3-{(13S,15R)-2-tert-Butyl-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 59 3-{(13S,15R)-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 60 3-{(13S,15R)-3-Hydroxy-2-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 61 3-{(13S,15R)-3-Hydroxy-4-nitro-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 62 3-{(13S,15R)-2-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 63 3-{(13S,15R)-4-Bromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 64 3-{(13S,15R)-2,4-Dibromo-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 65 3-{(13S,15R)-2-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 66 3-{(13S,15R)-4-Chloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 67 3-{(13S,15R)-2,4-Dichloro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 68 3-{(13S,15R)-2-Fluoro-3-hydroxy-17-[(E)-hydroxyimino]-13-methyl-7,8,9,11,12,13,14,15,16,17-decahydro-6H-cyclopenta[a]phenanthren-15-yl}-N-(5-methylthiazol-2-yl)propanamide;

Compound 69 3-{(13S,15S)-3-Hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 70 3-{(13S,15S)-2,4-Dibromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 71 3-{(13S,15S)-4-Bromo-3-hydroxy-17-[(Z)-hydroxyimino]-16-[1-hydroxy-meth-(E)-ylidene]-13-methyl-7,8,9,11,12,13,14,15,16,17-decahydro-6H-cyclopenta[a]phenanthren-15-yl}-N-(5-methylthiazol-2-yl)propanamide;

Compound 72 3-{(13S,15R)-17-[(E)-hydroxyimino]-2-{1-[(E)-hydroxyimino]-ethyl}]-3-methoxy-13-methyl-7,8,9,11,12,13,14,15,16,17-decahydro-6H-cyclopenta[a]phenanthren-15-yl}-N-(5-methylthiazol-2-yl)propanamide;

Compound 73 3-{(13S,15R)-3-Hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 74 3-{(13S,15R)-3-Methoxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 75 3-{(13S,15R)-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 76 3-{(13S,15R)-2-tert-Butyl-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 77 3-{(13S,15R)-3-Hydroxy-17-[(E)-methoxyimino]-13-methyl-2-nitro-7,8,9,11,12,13,14,15,16,17-decahydro-6H-cyclopenta[a]phenanthren-15-yl}-N-(5-methylthiazol-2-yl)propanamide;

Compound 78 3-{(13S,15R)-2-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 79 3-{(13S,15R)-3-Hydroxy-17-[(E)-methoxyimino]-13-methyl-4-nitro-7,8,9,11,12,13,14,15,16,17-decahydro-6H-cyclopenta[a]phenanthren-15-yl}-N-(5-methylthiazol-2-yl)propanamide;

Compound 80 3-{(13S,15R)-4-Amino-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 81 3-{(13S,15R)-3-Hydroxy-2-iodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 82 3-{(13S,15R)-3-Hydroxy-4-iodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 83 3-{(13S,15R)-3-Hydroxy-2,4-diiodo-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 84 3-{(13S,15R)-2-iodo-3-methoxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 85 3-{(13S,15R)-2-Bromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 86 3-{(13S,15R)-4-Bromo-3-hydroxy-17-[(E)-methoxyimino]-13-methyl-7,8,9,11,12,13,14,15, 16,17-decahydro-6H-cyclopenta[a]phenanthren-15-yl}-N-(5-methylthiazol-2-yl)propanamide;

Compound 87 3-{(13S,15R)-2,4-Dibromo-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 88 3-{(13S,15R)-2-Chloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 89 3-{(13S,15R)-4-Chloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 90 3-{(13S,15R)-2,4-Dichloro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 91 3-{(13S,15R)-2-Fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 92 3-{(13S,15R)-4-Fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 93 3-{(13S,15R)-2-Bromo-4-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 94 3-{(13S,15R)-4-Bromo-2-fluoro-3-hydroxy-17-[(E)-methoxyimino]-13-methyl-7,8,9,11,12,13,14,15,16,17-decahydro-6H-cyclopenta[a]phenanthren-15-yl}-N-(5-methylthiazol-2-yl)propanamide;

Compound 95 3-{(13S,15R)-3-hydroxy-17-[(E)-methoxyimino]-13-methyl-2-nitrile-7,8,9,11,12,13,14,15,16,17-decahydro-6H-cyclopenta[a]phenanthren-15-yl}-N-(5-methylthiazol-2-yl)propanamide;

Compound 96 3-{(13S,15R)-3-hydroxy-17-[(E)-methoxyimino]-13-methyl-4-nitrile-7,8,9,11,12,13,14,15,16,17-decahydro-6H-cyclopenta[a]phenanthren-15-yl}-N-(5-methylthiazol-2-yl)propanamide;

Compound 97 3-{(13S,15R)-3-Methoxy-17-[(E)-methoxyimino]-2-{1-[(E)-methoxyimino]-ethyl}-13-methyl-7,8,9,11,12,13,14,15,16,17-decahydro-6H-cyclopenta[a]phenanthren-15-yl}-N-(5-methylthiazol-2-yl)propanamide;

Compound 98 3-{(13S,15R)-3-Hydroxy-17-[(E)-methoxyimino]-13-methyl-2-morpholin-4-ylmethyl-7,8,9,11,12,13,14,15,16,17-decahydro-6H-cyclopenta[a]phenanthren-15-yl}-N-(5-methylthiazol-2-yl)propanamide;

Compound 99 3-{(13S,15R)-3-Hydroxy-17-[(E)-methoxyimino]-13-methyl-2-morpholin-4-ylmethyl-4-nitro-7,8,9,11,12,13,14,15,16,17-decahydro-6H-cyclopenta[a]phenanthren-15-yl}-N-(5-methylthiazol-2-yl)propanamide;

Compound 100 Acetic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 101 Dimethylamino-acetic acid (13S,15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 102 Sulphamic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 103 Dimethyl-sulfamic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 104 Methanesulphonic acid (13S, 15R)-17[(E)-methoxyimino]-13-methyl-15-[2-(5-methylthiazol-2-ylcarbamoyl)-ethyl]-7,8,9,11,12,13,14,15,16,17-decahydro-6H-cyclopenta[a]phenanthren-3-yl ester;

Compound 105 3-{(13S,15R)-17-[(E)-Ethoxyimino]-3-hydroxy-13-methyl-7,8,9,11,12,13,14,15,16,17-decahydro-6H-cyclopenta[a]phenanthren-15-yl}-N-(5-methylthiazol-2-yl)propanamide;

Compound 106 3-{(13S,15R)-2-tert-Butyl-17-[(E)-ethoxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide;

Compound 107 3-{(13S,15R)-17-[(E)-Allyloxyimino]-3-hydroxyl-13-methyl-7,8,9,11,12,13,14,15,16,17-decahydro-6H-cyclopenta[a]phenanthren-15-yl}-N-(5-methylthiazol-2-yl)propanamide;

Compound 108 3-{(13S,15R)-17-[(E)-Allyloxyimino]-3-hydroxyl-13-methyl-2-nitro-7,8,9,11,12,13,14,15,16,17-decahydro-6H-cyclopenta[a]phenanthren-15-yl}-N-(5-methylthiazol-2-yl)propanamide;

Compound 109 [(13S,15R)-3-Hydroxy-13-methyl-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid;

Compound 110 [(13S,15R)-2-tert-Butyl-3-hydroxy-13-methyl-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid;

Compound 111 [(13S,15R)-3-Hydroxy-13-methyl-2-nitro-15-[2-(5-methylthiazol-2-ylcarbamoyl)-ethyl]-6,7,8,9,11,12,13,14,15,16-decahydro-cyclopenta[a]phenanthren-(17E)-ylideneaminooxy]-acetic acid;

Compound 112 3-{(13S,15R)-3-Hydroxy-17-[(E)-N-urea-imino]-13-methyl-7,8,9,11,12,13,14,15,16,17-decahydro-6H-cyclopenta[a]phenanthren-15-yl}-N-(5-methylthiazol-2-yl)propanamide;

Compound 113 3-{(13S,15R)-2,4-Dibromo-3-hydroxy-17-[(E)-N-urea-imino]-13-methyl-7,8,9,11,12,13,14,15,16,17-decahydro-6H-cyclopenta[a]phenanthren-15-yl}-N-(5-methylthiazol-2-yl)propanamide;

Compound 114 3-{(7aS,10OR)-8-[(E)-Hydroxyimino]-7a-methyl-6,7,7a,8,9,10,10a,10b,11,12-decahydro-5bH-3-oxa-1-aza-dicyclopenta[a,i]phenathren-10-yl}-N-(5-methylthiazol-2-yl)propanamide;

Compound 115 3-{(7aS,10R)-8-[(E)-Methoxyimino]-7a-methyl-6,7,7a,8,9,10,10a,10b,11,12-decahydro-5bH-3-oxa-1-aza-dicyclopenta[a,i]phenathren-10-yl}-N-(5-methylthiazol-2-yl)propanamide;

Compound 116 3-{(3R,12aS)-1-[(E)-Methoxyimino]-1a-methyl-2,3,3a,3b,4,5,10b,11,12,12a-decahydro-1H-7-oxa-9-aza-dicyclopenta[a,h]phenathren-3-yl}-N-(5-methylthiazol-2-yl)propanamide;

Compound 117 3-{(3R,12aS)-6-Chloro-1-[(E)-methoxyimino]-12a-methyl-2,3,3a,3b,4,5,10b,11,12,12a-decahydro-1H-7-oxa-9-aza-dicyclopenta[a,h]phenathren-3-yl}-N-(5-methylthiazol-2-yl)propanamide;

Compound 118 3-{(3R,12aS)-1-[(E)-Methoxyimino]-8,12a-dimethyl-2,3,3a,3b,4,5,10b,11,12,12a-decahydro-1H-7-oxa-9-aza-dicyclopenta[a,h]phenanthren-3-yl}-N-(5-methylthiazol-2-yl)propanamide;

Compound 119 3-((6aS,10S)-1,3-Dibromo-2-hydroxy-6a-methyl-4-nitro-4b,6,6a,10,10a,10b,11,12-octahydro-5H-8-oxa-7-aza-pentaleno[2,1-a]phenanthren-10-yl}-N-(5-methylthiazol-2-yl)propanamide;

Compound 120 Methanesulphonic acid (6aS,10S)-6a-methyl-10-[2-(5-methylthiazol-2-ylcarbamoyl)-ethyl]-4b,6,6a,10,10a,10b,11,12-octahydro-5H-8-oxa-7-aza-pentaleno[2,1-a]phenanthren-2-yl ester;

Compound 121 3-{(13S,15R)-3-Hydroxy-17-[(E)-isobutylimino]-13-methyl-7,8,9,11,12,13,14,15,16,17-decahydro-6H-cyclopenta[a]phenanthren-15-yl}-N-(5-methylthiazol-2-yl)propionamide;

Compound 122 3-{(13S,15R)-3-Hydroxy-17-[(E)-2-methoxy-ethylimino]-13-methyl-7,8,9,11,12,13,14,15,16,17-decahydro-6H-cyclopenta[a]phenanthren-15-yl}-N-(5-methylthiazol-2-yl)propionamide;

Compound 123 3-{(13S,15R)-2-tert-Butyl-3-hydroxy-17-[(E)-2-methoxy-ethylimino]-13-methyl-7,8,9,11,12,13,14,15,16,17-decahydro-6H-cyclopenta[a]phenanthren-15-yl}-N-(5-methylthiazol-2-yl)propionamide; and Compound 124 3-((13S,15R,E)-2-(tert-butyl)-3-hydroxy-4-iodo-17-(methoxyimino)-13-methyl-7,8,9,11,12,13,14,15,16,17-decahydro-6H-cyclopenta[a]phenanthren-15-yl)-N-(5-methylthiazol-2-yl)propanamide;

or a pharmaceutically acceptable salt thereof.

19. A pharmaceutical composition comprising an effective amount of one or more compounds as claimed in claim 1, together with one or more pharmaceutically acceptable excipient(s).

20. The pharmaceutical composition as claimed in claim 19, further comprising one or more other active ingredients.

21. A method of treating a steroid hormone dependent malign or benign disease or disorder, comprising administering a compound as claimed in claim 1, to a patient in need thereof.

22. The method as claimed in claim 21, wherein the steroid hormone dependent malign or benign disease or disorder is selected from the group consisting of breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, urinary dysfunction, polycystic ovarian syndrome, lower urinary tract syndrome, multiple sclerosis, obesity, rheumatoid arthritis, colon cancer, tissue wounds, skin wrinkles and cataracts.

23. The method as claimed in claim 21, wherein the steroid hormone dependent malign or benign disease or disorder is a disease or disorder requiring the inhibition of 17β-HSD enzyme.

24. The method as claimed in claim 21, wherein the steroid hormone dependent malign or benign disease or disorder is an estradiol dependent disease or disorder.

* * * * *